United States Patent
Fu et al.

(10) Patent No.: US 12,366,570 B2
(45) Date of Patent: Jul. 22, 2025

(54) CELL-BASED ZNT8 ASSAY

(71) Applicant: THE JOHNS HOPKINS UNIVERSITY, Baltimore, MD (US)

(72) Inventors: Dax Fu, Short Hills, NJ (US); Chengfeng Merriman, Essex, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1268 days.

(21) Appl. No.: 17/108,441

(22) Filed: Dec. 1, 2020

(65) Prior Publication Data

US 2021/0302413 A1    Sep. 30, 2021

Related U.S. Application Data

(60) Provisional application No. 62/908,761, filed on Oct. 1, 2019.

(51) Int. Cl.
  *G01N 33/50* (2006.01)
  *C07K 16/28* (2006.01)
  *G01N 33/68* (2006.01)

(52) U.S. Cl.
  CPC ........... *G01N 33/507* (2013.01); *C07K 16/28* (2013.01); *G01N 33/6854* (2013.01); *C07K 2317/55* (2013.01)

(58) Field of Classification Search
  CPC ............. G01N 33/507; G01N 33/6854; G01N 33/5023; G01N 33/6872; C07K 16/28; C07K 2317/55; C07K 16/18
  See application file for complete search history.

(56) References Cited

U.S. PATENT DOCUMENTS

| | | |
|---|---|---|
| 4,399,216 A | 8/1983 | Axel et al. |
| 4,634,665 A | 1/1987 | Axel et al. |
| 4,880,935 A | 11/1989 | Thorpe |
| 5,122,368 A | 6/1992 | Greenfield et al. |
| 5,179,017 A | 1/1993 | Axel et al. |
| 5,225,539 A | 7/1993 | Winter |
| 5,399,363 A | 3/1995 | Liversidge et al. |
| 5,466,468 A | 11/1995 | Schneider et al. |
| 5,530,101 A | 6/1996 | Queen et al. |
| 5,543,158 A | 8/1996 | Greg et al. |
| 5,580,579 A | 12/1996 | Ruddy et al. |
| 5,585,089 A | 12/1996 | Queen et al. |
| 5,613,308 A | 3/1997 | Little |
| 5,622,929 A | 4/1997 | Willner et al. |
| 5,624,821 A | 4/1997 | Winter et al. |
| 5,629,001 A | 5/1997 | Michael et al. |
| 5,641,515 A | 6/1997 | Ramtoola |
| 5,641,640 A | 6/1997 | Hanning |
| 5,725,871 A | 3/1998 | Illum |
| 5,731,168 A | 3/1998 | Carter et al. |
| 5,756,353 A | 5/1998 | Debs |
| 5,780,045 A | 7/1998 | McQuinn et al. |
| 5,792,451 A | 8/1998 | Sarubbi et al. |
| 5,804,212 A | 9/1998 | Illum |
| 5,824,805 A | 10/1998 | King et al. |
| 5,834,597 A | 11/1998 | Tso et al. |
| 5,859,205 A | 1/1999 | Adair et al. |
| 5,869,046 A | 2/1999 | Presta et al. |
| 5,892,019 A | 4/1999 | Schlom et al. |
| 6,165,710 A | 12/2000 | Robinson |
| 6,214,345 B1 | 4/2001 | Firestone et al. |
| 6,407,213 B1 | 6/2002 | Carter et al. |
| 6,613,308 B2 | 9/2003 | Bartus et al. |
| 6,737,514 B1 | 5/2004 | Wang |
| 6,881,557 B2 | 4/2005 | Foote |
| 8,563,291 B2 | 10/2013 | Yoshimura et al. |
| 8,563,327 B2 | 10/2013 | Park et al. |
| 9,023,984 B2 | 5/2015 | Hutton et al. |
| 9,568,482 B2 | 2/2017 | Seve et al. |
| 9,810,697 B2 | 11/2017 | McKenna et al. |
| 11,016,085 B2 | 5/2021 | Fu |
| 11,078,251 B2 | 8/2021 | Mallone et al. |

(Continued)

FOREIGN PATENT DOCUMENTS

| | | |
|---|---|---|
| CN | 101646781 | 2/2010 |
| CN | 106084043 | 11/2016 |

(Continued)

OTHER PUBLICATIONS

Rudikoff et al., Proc Natl Acad Sci USA vol. 79 p. 1979 (Year: 1982).*
MacCallum et al., J. Mol. Biol. 262:732-745, (Year: 1996).*
Busch et al., Increased fatty acid desaturation and enhanced expression of stearoyl coenzyme A desaturase protects pancreatic beta-cells from lipoapoptosis, Diabetes, (2005), pp. 2917-2924, 54 (10).
Rojas et al., Pancreatic Beta Cell Death: Novel Potential Mechanisms in Diabetes Therapy, J Diabetes Res, (2018), 9601801, 2018.
Fabregat et al., The Reactome Pathway Knowledgebase, Nucleic Acids Res, (2018), pp. D649-D655, 46 (D1).
Murata et al., The immunoproteasome and thymoproteasome: functions, evolution and human disease, Nat Immunol, (2018), pp. 923-931, 19 (9).

(Continued)

*Primary Examiner* — Kimberly Ballard
*Assistant Examiner* — Stacey N MacFarlane
(74) *Attorney, Agent, or Firm* — Casimir Jones, S.C.; Robert A. Goetz

(57) ABSTRACT

The present invention relates to the fields of immunology and diabetes. More specifically, the present invention provides methods and compositions directed to the use of antibodies to quantify cellular pancreatic zinc transporter 8. In certain embodiment, the present invention provides methods and compositions directed to the use of antibodies to screen for modulators of the pancreatic zinc transporter, ZnT8. In one embodiment, a method comprises the steps of (a) permeabilizing human beta cells present in a substrate; (b) contacting the cells with a test agent; and (c) measuring the amount of zinc transporter 8 (ZnT8) using at least one anti-ZnT8 antibody or antigen-binding fragment thereof.

19 Claims, 15 Drawing Sheets

Specification includes a Sequence Listing.

(56) References Cited

U.S. PATENT DOCUMENTS

| | | |
|---|---|---|
| 11,510,996 B2 | 11/2022 | Pearson et al. |
| 11,841,363 B2 | 12/2023 | Fu |
| 11,892,457 B2 | 2/2024 | Fu et al. |
| 2009/0186364 A1 | 7/2009 | Yoshimura et al. |
| 2009/0191574 A1 | 7/2009 | Halperin |
| 2010/0068199 A1 | 3/2010 | Liang |
| 2010/0158909 A1 | 6/2010 | McDonagh et al. |
| 2012/0238572 A1 | 9/2012 | Su et al. |
| 2016/0025744 A1 | 1/2016 | Feldman et al. |
| 2017/0096497 A1 | 4/2017 | Weisbart |
| 2018/0243408 A1 | 8/2018 | Fanger et al. |
| 2019/0137485 A1 | 5/2019 | Fu |
| 2020/0132698 A1 | 4/2020 | Fu et al. |
| 2021/0154247 A1 | 5/2021 | Rottiers et al. |
| 2021/0238279 A1 | 8/2021 | Fu et al. |
| 2021/0263021 A1 | 8/2021 | Fu |
| 2022/0308052 A1 | 9/2022 | Fu et al. |

FOREIGN PATENT DOCUMENTS

| | | |
|---|---|---|
| CN | 106084051 | 11/2016 |
| CN | 106771233 | 5/2017 |
| EP | 404097 | 12/1990 |
| WO | WO 198705330 | 9/1987 |
| WO | WO 198912624 | 12/1989 |
| WO | WO 199311161 | 6/1993 |
| WO | WO 2008083331 | 7/2008 |
| WO | WO 2008131224 | 10/2008 |
| WO | WO 2009064901 | 5/2009 |
| WO | WO 2012062697 | 5/2012 |
| WO | WO 2012173184 | 12/2012 |
| WO | WO 2013071055 | 5/2013 |
| WO | WO 2014142517 | 9/2014 |
| WO | WO 2014160175 | 10/2014 |
| WO | WO 2017189483 | 11/2017 |
| WO | WO 2019014044 | 1/2019 |
| WO | WO 2020037174 | 2/2020 |
| WO | WO 2020247920 | 12/2020 |

OTHER PUBLICATIONS

Arvan et al., Islet autoantigens: structure, function, localization, and regulation, Cold Spring Harb Perspect Med, (2012), a007658, 2 (8).
Dudek et al., Constitutive and inflammatory immunopeptidome of pancreatic beta-cells, Diabetes, (2012), pp. 3018-3025, 61 (11).
Jarchum et al., In vivo cytotoxicity of insulin-specific CD8+ Tcells in HLA-A*0201 transgenic NOD mice, Diabetes, (2007), pp. 2551-2560, 56 (10).
Scotto et al., Zinc transporter (ZnT)8(186-194) is an immunodominant CD8+ T cell epitope in HLA-A2+ type 1 diabetic patients, Diabetologia, (2012), pp. 2026-2031, 55 (7).
Meng et al., Epoxomicin, a potent and selective proteasome inhibitor, exhibits in vivo antiinflammatory activity, Proc Natl Acad Sci USA, (1999), pp. 10403-10408, 96 (18).
Huang et al., Coupling of Insulin Secretion and Display of a Granule-resident Zinc Transporter ZnT8 on the Surface of Pancreatic Beta Cells, J Biol Chem, (2017), pp. 4034-4043, 292 (10).
Wan et al., Proteoliposome-based full-length ZnT8 self-antigen for type 1 diabetes diagnosis on a plasmonic platform, Proc Natl Acad Sci USA, (2017), pp. 10196-10201, 114 (38).
El Muayed et al., Acute cytokine-mediated downregulation of the zinc transporter ZnT8 alters pancreatic beta-cell function, J Endocrinol, (2010), pp. 159-169, 206 (2).
Egefjord et al., Zinc transporter gene expression is regulated by pro-inflammatory cytokines: a potential role for zinc transporters in beta-cell apoptosis?, BMC Endocr Disord, (2009), 7, 9.
Cheng et al., Tumor necrosis factor alpha-induced protein-3 protects zinc transporter 8 against proinflammatory cytokine-induced downregulation, Exp Ther Med, (2016), pp. 1509-1514, 12 (3).
Wong et al., Exploring the Association Between Demographics, SLC30A8 Genotype, and Human Islet Content of Zinc, Cadmium, Copper, Iron, Manganese and Nickel, Sci Rep, (2017), 473, 7 (1).
Parsons et al., The C-terminal cytosolic domain of the human zinc transporter ZnT8 and its diabetes risk variant, Febs J, (2018), pp. 1237-1250, 285 (7).
Flannick et al., Exome sequencing of 20,791 cases of type 2 diabetes and 24,440 controls, Nature, (2019), pp. 71-76, 570 (7759).
Chabosseau et al., Mitochondrial and ER-targeted eCALWY probes reveal high levels of free Zn2+, ACS Chem Biol, (2014), pp. 2111-2120, 9 (9).
Liu et al., Characterization of Zinc Influx Transporters (ZIPs) in Pancreatic beta Cells: Roles in Regulating Cytosolic Zinc Homeostasis and Insulin Secretion, J Biol Chem, (2015), pp. 18757-18769, 290 (30).
Taylor et al., Protein kinase CK2 triggers cytosolic zinc signaling pathways by phosphorylation of zinc channel ZIP7, Sci Signal, (2012), ra11, 5 (210).
Woodruff et al., The Zinc Transporter SLC39A7 (ZIP7) Is Essential for Regulation of Cytosolic Zinc Levels, Mol Pharmacol, (2018), pp. 1092-1100, 94 (3).
Ohashi et al., Zinc Transporter SLC39A7/ZIP7 Promotes Intestinal Epithelial Self-Renewal by Resolving ER Stress, PLoS Genet, (2016), e1006349, 12 (10).
Tuncay et al., Hyperglycemia-Induced Changes in ZIP7 and ZnT7 Expression Cause Zn(2+) Release From the Sarco(endo)plasmic Reticulum and Mediate ER Stress in the Heart, Diabetes, (2017), pp. 1346-1358, 66 (5).
Liu et al., Proinsulin maturation, misfolding, and proteotoxicity, Proc Natl Acad Sci USA, (2007), pp. 15841-15846, 104 (40).
Wenzlau et al., Novel diabetes autoantibodies and prediction of type 1 diabetes, Curr Diab Rep, (2013), pp. 608-615, 13 (5).
Li et al., Identification of novel HLA-A 0201-restricted cytotoxic T lymphocyte epitopes from Zinc Transporter 8, Vaccine, (2013), pp. 1610-1615, 31 (12).
Yu et al., Identification of Candidate Tolerogenic CD8(+) T Cell Epitopes for Therapy of Type 1 Diabetes in the NOD Mouse Model, J Diabetes Res, (2016), 9083103, 2016.
Ravassard et al., A genetically engineered human pancreatic beta cell line exhibiting glucose-inducible insulin secretion, J Clin Invest, (2011), pp. 3589-3597, 121 (9).
Barlow et al., Novel insights into pancreatic beta-cell glucolipotoxicity from real-time functional analysis of mitochondrial energy metabolism in INS-1E insulinoma cells, Biochem J, (2013), pp. 417-426, 456 (3).
Li et al., A syntaxin 1, Galpha(o), and N-type calcium channel complex at a presynaptic nerve terminal: analysis by quantitative immunocolocalization, J Neurosci, (2004), pp. 4070-4081, 24 (16).
Szoka et al., Comparative properties and methods of preparation of lipid vesicles (liposomes), Annu Rev Biophys Bioeng, (1980), pp. 467-508, 9.
Fred et al., Role of the AMP kinase in cytokine-induced human EndoC-betaH1 cell death, Mol Cell Endocrinol, (2015), pp. 53-63, 414.
Abdiche et al., "Determining Kinetics and Affinities of Protein Interactions Using a Parallel Real-time Label-free Biosensor, the Octet" Analytical Biochemistry, 2008, 377:209-217.
Aplin et al., "Preparation, Properties, and Applications of Carbohydrate Conjugates of Proteins and Lipids," CRC Crit. Rev. Biochem., May 1981, 22:259-306.
Barelle et al., "VNARs: An Ancient and Unique Repertoire of Molecules That Deliver Small, Soluble, Stable and High Affinity Binders of Proteins," Antibodies, 2015, 4(3):240-258.
Berge et al., "Pharmaceutical salts," J. Pharm. Sci., Jan. 1977, 66:1-19.
Better et al., "*Escherichia coli* secretion of an active chimeric antibody fragment," Science, May 1988, 240(4855):1041-1043.
Better et al., "Expression of Engineered Antibodies and Antibody Fragments in Microorganisms," Methods in Enzymology, 1989, 178:476-496.
Bindels et al., "mScarlet: a bright monomeric red fluorescent protein for cellular imaging," Nat Methods, 2017, 14:53-56.
Bird et al., "Single chain antibody variable regions," TIBTECH, 1991, 9:132-137.
Bird et al., "Single-Chain Antigen-Binding Proteins," Science, 1988, 242(4877):423-426.

(56) References Cited

OTHER PUBLICATIONS

Bloem et al., "The elusive role of B lymphocytes and islet autoantibodies in (human) type 1 diabetes, " Diabetologia, 2017, 60:1185-1189.
Bonner-Weir et al., "New perspectives on the microvasculature of the islets of Langerhans in the rat," Diabetes, 1982, 31:883-889.
Brenner et al., "Encoded combinatorial chemistry," Proc. Natl. Acad. Sci. USA. Jun. 1992, 89(12):5381-5383.
Carell et al., "New promise in combinatorial chemistry: synthesis, characterization, and screening of small-molecule libraries in solution," Chem. Biol. 1995, 2(3):171-183.
Carter et al., "High level *Escherichia coli* expression and production of a bivalent humanized antibody fragment," Biotechnology, 1992, 10(2):163-167.
Chabosseau et al., "Mitochondrial and ER-targeted eCALWY probes reveal high levels of free Zn2+," ACS Chem Biol, 2014, 9:2111-2120.
Chimienti, "Zinc, pancreatic islet cell function and diabetes: new insights into an old story," Nutr Res Rev, 2013, 26:1-11.
Cieslak et al., "Role of proinflammatory cytokines of pancreatic islets and prospects of elaboration of new methods for the diabetes treatment," Acta Biochim Pol, 2015, 62:15-21.
Co et al., "A humanized antibody specific for the platelet integrin gpIIb/IIIa," J Immunol, 1994, 152(6):2968-2976.
Corbin et al., "A Practical Guide to Rodent Islet Isolation and Assessment Revisited," Biol Proced Online, 2021, 23(1):7.
Cwirla et al., "Peptides on phage: a vast library of peptides for identifying ligands," Biochemistry 1990, 87(16):6378-6382.
Darling et al., "Kinetic exclusion assay technology: characterization of molecular interactions," Assay and Drug Dev Tech, 2004, 2:647-657.
Dubowchik et al., "Receptor-mediated and enzyme-dependent targeting of cytotoxic anticancer drugs," Pharm. Therapeutics., Aug. 1999, 83(2):67-123.
Dwivedi et al., "Loss of ZnT8 function protects against diabetes by enhanced insulin secretion," Nat Genet, 2019, 51:1596-1606.
Edge et al., "Deglycosylation of Glycoproteins by Trifluoromethanesulfonic Acid," Anal. Biochem., 1981, 118:131-137.
El-Gohary et al., "Three-dimensional analysis of the islet vasculature," Anat Rec (Hoboken), 2012, 295:1473-1481.
Eriksson et al., "Pancreatic imaging using an antibody fragment targeting the zinc transporter type 8: a direct comparison with radio-iodinated Exendin-4," Acta Diabetol, 2018, 55:49-57.
Felder, "The Challenge of Preparing and Testing Combinatorial Compound Libraries in the Fast Lane, at the Front end of Drug Development,," Chimia 1994, 48:512-541.
Fukuda et al., "Invitro ecolution of single-chain antibodies using mRNA display," Nucleic Acids Res., 2006, 34(19):e127.
Gallop et al., "Applications of combinatorial technologies to drug discovery. 1. Background and peptide combinatorial libraries," J. Med. Chem., 1994, 37(9):1233-1251.
Garner, "Na,K-ATPase in the nuclear envelope regulates Na+: K+ gradients in hepatocyte nuclei," J Membr Biol, 2002, 187:97-115.
Ghetie et al., "Multiple roles for the major histocompatibility complex class I-related receptor FcRn," Annu. Rev. Immunol., 2000, 18:739-766.
Ghetie et al., "Transcytosis and catabolismof antibody," Immunol. Res., 2002, 25(2):97-113.
Gordon et al., "Applications of Combinatorial Technologies to Drug Discovery. 2. Combinatorial Organic Synthesis, Library Screening Strategies, and Future Directions," J Med. Chem. 1994, 37(10):1385-1401.
Gu et al., "Novel autoantibodies to the beta-cell surface epitopes of ZnT8 in patients progressing to type-1 diabetes," J Autoimmun, 2021, 122:102677.
Hahn et al., "3D imaging of human organs with micrometer resolution—applied to the endocrine pancreas," Commun Biol, 2021, 4:1063.

Hara et al., "Transgenic mice with green fluorescent protein-labeled pancreatic beta-cells," Am J Physiol Endocrinol Metab, 2003, 284:E177-183.
Hieter et al., "Evolution of human immunoglobulin kappa J region genes.," J. Biol. Chem., Feb. 1982, 257(3):1516-1522.
Hinton et al., "Engineered human IgG antibodies with longer serum half-lives in primates," J. Biol. Chem., Feb. 2004, 279(8):6213-6216.
Ho et al, Gene, "Site-directed mutagenesis by overlap extension using the polymerase chain reaction." Apr. 1989, 77(1):51-59.
Holliger et al., "'Diabodies': small bivalent and bispecific antibody fragments," Proc. Natl. Acad. Sci. U S A., Jul. 1993, 90:6444-6448.
Houghten et al., "Generation and use of synthetic peptide combinatorial libraries for basic research and drug discovery," Nature, 1991, 354:84-86.
Houghten, "Peptide libraries: criteria and trends," Trends Genet, 1993, 9:235-239.
Huang, "Zinc and its transporters, pancreatic beta-cells, and insulin metabolism," Vitarn Horm, 2014, 95:365-390.
Hudson, et al., "High avidity scFv multimers; diabodies and triabodies," J Immunol. Methods, Dec. 1999, 231(1-2):177-189.
Huston et al., "Protein engineering of antibody binding sites: recovery of specific activity in an anti-digoxin single-chain Fv analogue produced in *Escherichia coli*," Proc. Natl. Acad. Sci. U S A., Aug. 1988, 85:5879-5883.
Ionescu-Tirgoviste et al., "A 3D map of the islet routes throughout the healthy human pancreas," Sci Rep, 2015, 5:14634.
Iwahashi et al., "CDR substitutions of a humanized monoclonal antibody (CC49): contributions of individual CDRs to antigen binding and immunogenicity," Mol. Immunol., 1999, 36:1079-1091.
Jermutus et al., "Tailoring in vitro evolution for protein affinity or stability," Proc. Natl. Acad. Sci. USA, Dec. 2000, 98:75-80.
Johne et al., "Epitope mapping and binding kinetics of monoclonal antibodies studied by real time biospecific interaction analysis using surface plasmon resonance," J. Immunol. Methods, Apr. 1993, 160(2):191-198.
Johnson et al, "Anti-tumor activity of CC49-doxorubicin immunoconguates," Anticancer Res. 1995, 15:1387-93.
Kambe et al., "Current understanding of ZIP and ZnT zinc transporters in human health and diseases, " Cell Mol Life Sci, 2014, 71:3281-3295.
Kambe et al., "Zinc transporters and their functional integration in mammalian cells," J Biol Chem, 2021, 100320.
Kaufman et al., "Amplification and expression of sequences cotransfected with a modular dihydrofolate reductase complementary dna gene," J Mol. Biol. 1982, 159(4):601-621.
Kim et al., "In situ quantification of pancreatic beta-cell mass in mice," J Vis Exp., 2010, 40:1-4.
Lam et al., "A new type of synthetic peptide library for identifying ligand-binding activity," Nature, 1991, 354:82-84.
Lamoyi, "Preparation of F(ab')2 fragments from mouse IgG of various subclasses," Methods in Enzymology, 1989, 121:652-663.
Lau et al, "Conjugation of doxorubicin to monoclonal anti-carcinoembryonic antigen antibody via novel thiol-directed cross-linking reagents," Bioorg-Med-Chem., 1995, 3(10):1299-1304.
Lau et al, "Novel doxorubicin-monoclonal anti-carcinoembryonic antigen antibody immunoconjugate activity in vitro," Bioorg-Med-Chem., 1995, 3(10):1305-12.
Lazar et al., "Engineered antibody Fc variants with enhanced effector function," Proc. Natl. Acad. Sci. USA, 2006, 103(11):4005-4010.
Lebl et al., "One-Bead-One-Structure Cornbinatorial Libraries, " Biopolymers, 1995, 37:177-198.
Lebowitz et al., "Modem analytical ultracentrifugation in protein science: A tutorial review," Protein Science, 2002, 11:2067-2079.
Lei et al., "Characterization of the Erwinia carotovora pelB gene and its product pectate lyase," J. Bacteriol., Sep. 1987, 169(9):4379-4383.
Lemaire et al., Insulin crystallization depends on zinc trar 1 sporter ZnT8 expression, but is not required. for nor.mal glucose homeostasis in .mice. Proc Natl Acad Sci USA 106:14872-14877.

(56) References Cited

OTHER PUBLICATIONS

Lemaire et al., "Zinc transporters and their role in the pancreatic beta-cell," J Diabetes Invesrig, 2012, 3:202-211.

Lernmark et al., "Islet-cell-surface antibodies in juvenile diabetes mellitus," N Engl J Med, 1978, 299:375-380.

Lippow et al., "Computational design of antibody-affinity improvement beyond in vivo maturation," Nat. Biotechnol., 2005, 25(10):1171-1176.

Liston et al., "Beta-Cell Fragility As a Common Underlying Risk Factor in Type 1 and Type 2 Diabetes, " Trends Mol Med, 2017, 23:181-194.

Liu et al., "Characterization of Zinc Influx Transporters (ZTPs) in Pancreatic beta Cells: Roles in Regulating Cytosolic Zinc Homeostasis and Insulin Secretion," J Biol Chem, 2015, 290(30):18757-18769.

Liu et al., "Proinsulin maturation, misfolding, and proteotoxicity," Proc Natl Acad Sci USA, 2007, 104:15841-15846.

Lu et al., "Structure of the zinc transporter YiiP," Science, 2007, 317(5845):1746-1748.

Lukowiak et al., "Identification and purification of functional human beta-cells by a new specific zinc-fluorescent probe," J Histochem Cytochem, 49:519-528.

Lund et al., "Human Fc gamma RI and Fc gamma RII interact with distinct but overlapping sites on human IgG," J Immun., Oct. 1991, 147(8):2657-2662.

Madden et al., "Synthetic Combinatorial Libraries: Views on Techniques and Their Application,," Perspectives in Drug Discovery and Design, 1995, 2:269-282.

Mattila et al, "Extensive allelic sequence variation in the J region of the human immunoglobulin heavy chain gene locus," Eur. J. Immunol., 1995, 25:2578-2582.

Merriman et al., "Down-regulation of the islet-specific zinc transporter-8 (ZnT8) protects human insulinoma cells against inflammatory stress," J Biol Chem, 2019, 294:16992-17006.

Milenic et al, "Construction, Binding Properties, Metabolism, and Tumor Targeting of a Single-Chain Fv Derived from the Pancarcinoma Monoclonal Antibody CC49," Cancer Research, 1991, 51:6363-6371.

Millstein et al., "Hybrid hybridomas and their use in immunohistochemistry," Nature, Oct. 1983, 305:537-539.

Mizushima et al., "pEF-BOS, a powerful mammalian expression vector," Nucleic Acids Res., 1990, 18:5322.

Morgan et al., "The N-terminal end of the CH2 domain of chimeric human IgGI anti-HLA-DR is necessary for C1q, Fc gamma RI and Fc gamma RIII binding," Immunology, 1995, 86(5):319-24.

Morton et al., "Kinetic analysis of macromolecular interactions using surface plasmon resonance hiosensors" Methods in Enzymology, 1998, 295:268-294.

Mulligan et al., "Synthesis of rabbit β-globin in cultured monkey kidney cells following infection with a SV40 B-globin recombinant genome," Nature, 1979, 277:108-114.

Muratore et al., "The vascular architecture of the pancreatic islets: A homage to August Krogh," Comp Biochem Physiol A Mol Integr Physiol, 2021, 252:110846.

Neumann et al., "Gene transfer into mouse lyoma cells by electroporation in high electric fields," EMBO J. 1982, 1(7):841-845.

Neville et al, "Enhancement of Immunotoxin Efficacy by Acid-cleavable Cross-linking Agents Utilizing Diphtheria Toxin and Toxin Mutants," Journal of Biological Chemistry., 1989, 264(25):14653-14661.

Noguchi et al., "Pharmacokinetic prediction of an antibody in mice based on an in vitro cell-based approach using target receptor-expressing cells," Sci Rep, 2020, 10:16268.

Ovacik et al., "Tutorial on Monoclonal Antibody Pharmacokinetics and Its Considerations in Early Development," Clin Transl Sci, 2018, 11:540-552.

Pantoliano et al, "Conformational stability, folding, and ligand-binding affinity of single-chain Fv immunoglobulin fragments expressed in Escherichia coli," Biochemistry, 1991, 30(42):10117-10125.

Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol, 2002, 169:3076-3084.

Peterson et al., "A long-lived IL-2 mutein that selectively activates and expands regulatory T cells as a therapy for autoimmune disease," J Autoimmun, 2018, 95:1-14.

Pierce et al., "Isothermal Titration Calorimetry of Protein-Protein Interactions," Methods, 1999, 19:213-221.

Rajpal et al., "A general method for greatly improving the affinity of antibodies by using combinatorial libraries," PNAS, 2005, 102(24):8466-71.

Roep et al., "Type 1 diabetes mellitus as a disease of the beta-cell (do not blame the immune system?)," Nat Rev Endocrinol, 2021, 17:150-161.

Rousseaux et al., "Optimal conditions for the preparation of proteolytic fragments from monoclonal IgG of different rat IgG subclasses," Methods in Enzymology, 1989, 121:663-669.

Saunders et al., "Ectonucleoside Triphosphate Diphosphohydrolase-3 Antibody Targets Adult Human Pancreatic beta Cells for In Vitro and In Vivo Analysis," 2018, Cell Metab.

Shields et al, "High resolution mapping of the binding site on human IgG1 for Fc gamma RI, Fc gamma RII, Fc gamma RIII, and FcRn and design of IgG1 variants with improved binding to the Fc gamma R, High resolution mapping of the binding site on human IgG1 for Fc gamma RI, Fc gamma RII, Fc gamma RIII, and FcRn and design of IgG1 variants with improved binding to the Fc gamma R," J. Biol. Chem., 2001, 276(9):6591-604.

Shin et al, "Physical map of the 3' region of the human immunoglobulin heavy chain locus: clustering of autoantibody-related variable segments in one haplotype," EMBO J. 1991, 10:3641-3645.

Sjolander et al., "Integrated fluid handling system for biomolecular interaction analysis," Anal. Chem, 1991, 63:2338-2345.

Sojar et al., "A chemical method for the deglycosylation of proteins," Arch. Biochem. Biophys., 1987, 259(1):52-57.

Stull et al., "Mouse islet of Langerhans isolation using a combination of purified collagenase and neutral protease," J Vis Exp., Sep. 2012, 67:4137.

Szabo et al., "Surface plasmon resonance and its use in biomolecular interaction analysis (BIA)," Curr. Opin. Struct. Biol. Oct. 1995, 5(5):699-705.

Takkinen et al, "An active single-chain antibody containing a cellulase linker domain is secreted by *Escherichia coli*," Protein Engineering, 1991, 4:837-841.

Tamura et al., "Structural Correlates of an Anticarcinoma Antibody: Identification of Specificity-Determining Residues (SDRs) and Development of a Minimally Immunogenic Antibody Variant by Retention of SDRs Only," Journal of Immunology, 2000, 164(3):1432-1441.

Thomas et al., "The natural autoantibody repertoire of nonobese diabetic mice is highly active," J Immunol, 2002, 169:6617-6624.

Thorpe et al., "New Coupling Agents for the Synthesis of Immunotoxins Containing a Hindered Disulfide Bond with Improved Stability in Vivo," Cancer Res., 1987, 47(22):5924-5931.

Thorpe et al., "The preparation and cytotoxic properties of antibody-toxin conjugates, " Immunol. Rev., 1982, 62:119-58.

Thorp-Greenwood et al., "Multimodal radio-(PET/SPECT) and fluorescence imaging agents based on metallo-radioisotopes: current applications and prospects for development of new agents," Dalton Trans, 2011, 40(23):6129-6143.

Thotakura et al., "Enzymatic deglycosylation of glycoproteins," Meth. Enzymol., 1987, 138:350-359.

Tozzoli, "Receptor autoimmunity: diagnostic and therapeutic implications," Auto Immun Highlights, 2020, 11:1.

Urlaub et al., "Isolation of Chinese hamster cell mutants deficient in dihydrofolate reductase activity," Proc. Natl. Acad. Sci. USA, 1980, 77:4216-4220.

Vajdos et al., "Comprehensive functional maps of the antigen-binding site of an anti-ErbB2 antibody obtained with shotgun scanning mutagenesis," Journal of Molecular Biology, Jul. 2002, 320(2): 415-428.

(56) References Cited

OTHER PUBLICATIONS

Ward et al., "Binding activities of a repertoire of single immunoglobulin variable domains secreted from *Escherichia coli*," Nature, Oct. 1989, 341:544-546.
Wigler et al., "Biochemical transfer of single-copy eucaryotic genes using total cellular DNA as donor," Cell, 1978, 14(3):725-731.
Winkel et al., "Islet cell surface antibodies from insulin-dependent diabetics bind specifically to pancreatic B cells," J Clin Invest, 1982, 70:41-49.
Xue et al., "Cryo-EM structures of human ZnT8 in both outward- and inward-facing conformations," Elife, 2020, 9:e58823.
Arnon et al, "Monoclonal Antibodies For Immunotargeting Of Drugs In Cancer Therapy," Monoclonal Antibodies And Cancer Therapy, 1986, pp. 243-256.
Ashcroft et al., "Diabetes mellitus and the B cell: the last ten years," Cell, Mar. 16, 2012, 148(6):1160-71.
Atkinson et al., "How does type 1 diabetes develop?: the notion of homicide or beta-cell suicide revisited," Diabetes, 2011, 60(5):1370-1379.
Benton et al., "creening lambdagt recombinant clones by hybridization to single plaques in situ," Science, Apr. 1977, 196(4286):180-182.
Bodganov et al., "Lipids and topological rules governing membrane protein assembly," Biochim. Biophys. Acta, 2014, 1843(8):1475-1488.
Boesgaard et al., "The common SLC30A8 Arg325Trp variant is associated with reduced first-phase insulin release in 846 non-diabetic offspring of type 2 diabetes patients-the EUGENE2 study," Diabetologia, May 2008, 51(5):816-20.
Bonneford et al., "Rare and common genetic events in type 2 diabetes: what should biologists know?" Cell Metab, Mar. 2015, 21(3):357-68.
Burbelo et al., "Luciferase Immunoprecipilation Systems for Measuring Antibodies in Autoimmune and nfectious Diseases," Transl Res, 2015, 165:325-335.
Chao et al., "Kinetic Study of the Antiport Mechanism of an *Escherichia coli* Zinc Transporter, ZitB," J Biol Chem, 2004, 279(13):12043-12050.
Chatterjee et al., "Type 2 diabetes," Lancet, Jun. 2017, 389(10085):2239-2251.
Cheng et al., "Prokaryotic Expression of Bioactive Zinc Transporter 8 Antigens and Detection of Diabetes Specific Autoantibodies in a Single Dot Immunogold Filtration Assay," Clin Lab, 2015, 10:1445-1452.
Cherezov et al., "Insights into the mode of action of a putative zinc transporter CzrB in Thermus thermophilus," Structure, Sep. 2008, 16(9):1378-88.
Chimienti et al., "In vivo expression and functional characterization of the zinc transporter Zn TB in glucose-induced nsulin secretion," J Cell Sci, Oct. 2006, 119(Pt 20):4199-4206.
Darmon et al., "Oriented reconstitution of red cell membrane proteins and assessment of their transmembrane :lisposition by immunoquenching of fluorescence," Biochimica et Biophysica Acta, 1985, 817:238-248.
Degorce et al., "HTRF: A technology tailored for drug discovery—a review of theoretical aspects and recent applications," Curr Chem Genomics, May 28, 2009, 3:22-32.
Delic-Sarac et al., "ELISA Test for Analyzing of Incidence of Type 1 Diabetes Autoantibodies (GAD and A2) in Children and Adolescents," Acta Inform Med, 2016, 24:61-65.
Dunn, "Zinc-ligand interactions modulate assembly and stability of the insulin hexamer—a review," Biometals, Aug. 2005, 18(4):295-303.
Extended European Search Report in European Application No. 19849457.7, dated Jul. 13, 2022, 14 pages.
Ferrannini et al., "Progression to diabetes in relatives of type 1 diabetic patients: mechanisms and mode of onset," Diabetes, 2010, 59(3):679-685.
Friend, et al., "Translational genomics. Clues from the resilien," Science, May 2014, 344(6187):970-2.

Geertsma et al., "Membrane reconstitution of ABC transporters and assays of translocator function, " Nature Protocols, 2008, 3(2):256-266.
Ghazalpour et al., "Comparative analysis of proteome and transcriptome variation in mouse," PLoS Genet, 2011, 7:e1001393.
Grunstein et al., "Colony hybridization: a method for the isolation of cloned DNAs that contain a specific gene, " Proc. Nat. Acad. Sci. USA, 1975, 72(10):3961-3965.
Gupta et al., "Visualizing the kinetic power stroke that drives proton-coupled zinc(II) transport," Nature, 2014, 512:101-104.
Hoch et al., "Histidine pairing at the metal transport site of mammalian ZnT transporters controls Zn2+ over Cd2+ selectivity," Proc Natl Acad Sci U S A, May 2012, 109(19):7202-7.
Ilonen et al., "Patterns of beta-cell autoantibody appearance and genetic associations during the first years of life," Diabetes, 2013, 32(10):3636-3640.
International Preliminary Report on Patentability in International Application No. PCT/US2020/036625, dated Dec. 7, 2021, 5 pages.
International Search Report and Written Opinion in International Application No. PCT/US2020/036625, dated Sep. 17, 2020, 7 pages.
Inzucchi et al., "Management of Hyperglycernia in type 2 diabetes: a patient-centered approach: position statement of the American Diabetes Association (ADA) and the European Association for the Study of Diabetes (EASD)," Diabetes Care, Jun. 2012, 35(6):1364-79.
Jaraosz-Chobot et al., "Rapid increase in the incidence of type 1 diabetes in Polish children from 1989 to 2004, and predictions for 2010 to 2025," Diabetologia, 2011, 54:508-515.
Jefferis et al., "Human immunoglobulin allotypes: possible implications for immunogenicity," Mabs, 2009, 1(4):332-338.
Kawasaki, "ZnT8 and type 1 diabetes," Endocrine Journal, 2012, 59(7):531-537.
Kim et al., "Antibody Engineering for the Development of Therapeutic Antibodies," Molecules and Cells, 2005, 20(1):17-29.
Kimmel, "Identification and characterization of specific clones: strategy for confirming the validity of presumptive lones," Methods in Enzymology, 1987, 152:507.
Klingensmith et al., "The presence of GAD and IA-2 antibodies in youth with a type 2 diabetes phenotype: results from the TODAY study," Diabetes Care., 2010, 33:1970-1975.
Kodama et al., "Expression-Based Genome-Wide Association Study Links Vitamin D-Binding Protein With A\utoantigenicity in Type 1 Diabetes," Diabetes, 2016, 65(5):1341-1349.
Li et al., "hZnT8 (Slc30a8) Transgenic Mice That Overexpress the R325W Polymorph Have Reduced Islet Zn2+ and Proinsulin Levels, Increased Glucose Tolerance After a High-Fat Diet, and Altered Levels of Pancreatic Zinc Binding Proteins," Diabetes, Feb. 2017, 66(2):551-559.
Li et al., "Multiplexed Anli-Toxoplasma IgG, IgM and IgA Assay on Plasmonic Gold Chips: Towards Making Mass Screening Possible with Dye Test Precision," J Clin Microbiol, 2016, 54:1726-1733.
Lim et al., "High-efficiency screening of monoclonal antibodies for membrane protein crystallography, " PLoS One, 2011, 6(9):e24653.
Long et al., "Rising incidence of type 1 diabetes is associated with altered immunophenotype at diagnosis," Diabetes, 2012, 61:683-686.
Lu et al., "Structural basis for autoregulalion of the zinc transporter YiiP," Nat Struct Mol Biol, 2009, 16:1063-1067.
Mathiowitz et al., "Biologically erodable microssheres as potential oral drug delivery systems," Nature, 1997, 386(6623):410-4.
Mittermayer et al., "Addressing unmet medical needs in type 2 diabetes: a narrative review of drugs under :levelopmenl," Curr Diabetes Rev, 2015, 11(1):17-31.
NCBI Accession No. ABQ59023. 1, "SLC30A8 protein [*Homo sapiens*]".
NCBI Accession No. KR712225. 1, "Synthetic construct *Homo sapiens* clone CCSBHm_00900180 SLC30A8 (SLC30A8) mRNA, encodes complete protein."
Ohana et al., "Identification of the Zn2+ binding site and mode of operation of a mammalian Zn2+ transporter," J Biol Chem, Jun. 2009, 284(26):17677-86.

(56) References Cited

OTHER PUBLICATIONS

PCT International Preliminary Report on Patentability in International Application No. PCT/US2017/029250, dated Oct. 30, 2018, 5 pages.

PCT International Preliminary Report on Patentability in International Application No. PCT/US2019/046747, dated Feb. 16, 2021, 7 pages.

PCT International Search and Written Opinion in International Application No. PCT/US2017/029250, dated Aug. 17, 2017, 6 pages.

PCT International Search Report and Written Opinion in International Application No. PCT/US2019/046747, dated Nov. 28, 2019, 8 pages.

PCT Invitation to Pay Additional Fees And, Where Applicable, Protest Fee in International Application No. PCT/US2022/075156, mailed on Nov. 3, 2022, 2 pages.

Pearson, "Zinc transport and diabetes risk," Nat Genet, Apr. 2014, 46(4):323-4.

Pettersen et al., "UCSF Chimera—a visualization system for exploratory research and analysis," J Comput Chem, Oct. 2004, 25(13):1605-12.

Pietropaolo et al., "Primer: immunity and autoimmunity," Diabetes, 2008, 57(11):2872-2882.

Pluckthun et al., "Expression of functional antibody Fv and Fab fragments in *Escherichia coli*," Methods in Enzymology, 1989, 178:497-515.

Prasad et al., "Genetics of Type 2 Diabetes-Pitfalls and Possibilities," Genes (Basel), Mar. 2015, 6(1):87-123.

Punjani et al., "cryoSPARC: algorithms for rapid unsupervised cryo-EM structure determination," Nat Methods, Mar. 2017, 14(3):290-296.

Qian et al., "Screening and identification of human ZnT8-specific single-chain variable fragment (scFv) from type 1 diabetes phage display library," Science China Life Sciences, Jun. 2016, 59(7):686-693.

Rohou et al., "CTFFIND4: Fast and accurate defocus estimation from electron micrographs," J Struct Biol, Nov. 2015, 192(2):216-21.

Rutter, "Think zinc: New roles for zinc in the control of insulin secretion," Islets, Jan.-Feb. 2010, 2(1):49-50.

Scheres, "RELION: implementation of a Bayesian approach to cryo-EM structure determination," J Struct Biol, Dec. 2012, 180(3):519-30.

Schwanhausser et al., "Global quantification of mammalian gene expression control," Nature, 2011, 473:337-342.

Scott et al., "A genome-wide association study of type 2 diabetes in Finns detects multiple susceptibility variants," Science, Jun. 2007, 316(5829):1341-5.

Skarstrand et al., "Zinc transporter 8 (ZnT8) autoantibody epitope specificity and affinity examined with ecombinant ZnT8 variant proteins in specific ZnT8R and ZnT8W autoantibody-positive type 1 diabetes patients," Clinical & Experimental Immunology, 2015, 179(2):220-229.

Sosenko et al., "The Use of Electrochemiluminescence Assays to Predict Autoantibody and Glycemic Progression Toward Type 1 Diabetes in Individuals with Single Autoantibodies," Diabetes Technol Ther, 2017, 3:183-187.

Steck et al., "Predictors of Progression From the Appearance of Islet Autoantibodies to Early Childhood Diabetes: The Environmental Determinants of Diabetes in the Young (TEDDY)," Diabetes Care., 2015, 38(5):808-813.

Stumvoll et al., "Type 2 diabetes: principles of pathogenesis and therapy," Lancet, Apr. 9-15, 2005, 365(9467):1333-46.

Sun et al., "Gene silencing of ZnT8 attenuates inflammation and protects pancreatic tissue injury in T1D," Immunology Letters, Jun. 2018, 198:1-6.

Surface Plasmons on Smooth and Rough Surfaces and on Gratings, Springer Verlag, 1988, 140 pages.

Tabakman et al., "Plasmonic substrates for multiplexed protein microarrays with femlomolar sensitivity and broad dynamic range," Nat Commun.

Takenaga et al., "Microparticle resins as a potential nasal drug delivery system for insulin," J Control Release, 1998, 52:81-87.

Tamaki et al., "The diabetes-susceptible gene SLC30A8/ZnT8 regulates hepatic insulin clearance," J Clin Invest, Oct. 2013, 123(10):4513-24.

Tiberti et al., "Detection of four diabetes specific autoantibodies in a single radioimmunoassay: an nnovative high-throughput approach for autoimmune diabetes screening," 2011, Clin Exp Immunol 3:317-324.

Ustinova et al., "Characterization of monoclonal ZnT8-specific antibody," Frontiers in Immunology, Jan. 2013, retrieved from URL<https://internal-www.frontiersin.org/Community/AbstractDetails.aspx?ABS_DOI=10.3389/conf.fim mu.2013.02.00326&eid=&sname=>, 2 pages.

Vyas et al., "Molecular recognition of oligosaccharide epitopes by a monoclonal Fab specific for Shigella flexneri Y ipopolysaccharide: X-ray structures and thermodynamics," Biochemistry, Nov. 19, 2002, 41(46):13575-86.

Wahl, "Molecular hybridization of immobilized nucleic acids: theoretical concepts and practical considerations," Methods in Enzymology, 1987, 152:399.

Wenzlau et al., "A common nonsynonymous single nucleotide polymorphism in the SLC30A8 gene determines ZnT8 Autoantibody specificity in type 1 diabetes," Diabetes, 2008, 57(10):2693-2697.

Wenzlau et al., "Changes in Zinc Transporter 8 Autoantibodies Following Type 1 Diabetes Onset: The Type 1 Diabetes Genetics Consortium Autoantibody Workshop," Diabetes Care, 2015, 38(Supplement 2):S14-20.

Wu et al., "An electrochemiluminescence (ECL)-based assay for the specific detection of anti-drug antibodies of the IgE isotype," J Pham Biomed Anal, 2013, 86:73-81.

Yi et al., "Different role of zinc transporter 8 between type 1 diabetes mellitus and type 2 diabetes mellitus" J Diabetes Investig, 2016, 7:459-465.

Yu et al., "Antiislet autoantibodies usually develop sequentially rather than simultaneously," Journal of Clinical Endocrinology & Metabolism, 1996, 81(12):4264-4267.

Yu et al., "Early expression of antiinsulin autoantibodies of humans and the NOD mouse: evidence for early dletermination of subsequent diabetes," Proc Nall Acad Sci USA, 2000, 97(4):1701-1706.

Yu et al., "Proinsulin/Insulin autoantibodies measured with electrochemiluminescent assay are the earliest indicator of prediabetic islet autoimmunity," Diabetes Care, 2013, 36(8):2266-2270.

Zeggini et al., "Replication of genome-wide association signals in UK samples reveals risk loci for type 2 diabetes," Science, Jun. 1, 2007, 316(5829):1336-41.

Zhang et al., "A plasmonic chip for biomarker discovery and diagnosis of type 1 diabetes," Nat Med, 2013, 20:948-953.

Zhang et al., "A Simple Statistical Parameter for Use in Evaluation and Validation of High Throughput Screening Assays," J Biomol Screen, 1999, 4(2):67-73.

Zhang et al., "Diagnosis of Zika virus infection on a nanotechnology platform," Nat Med 2017, 23:548-550.

Ziegler et al., "Seroconversion to multiple islet autoantibodies and risk of progression to diabetes in children," JAMA, 2013, 309(23):2473-2479.

Extended European Search Report in European Application No. 18832105.3, dated Mar. 11, 2021, 11 pages.

GenBank Accession No. NM_001172814.1, "*Homo sapiens* solute carrier family 30 (zinc transporter), member 8 (SLC30A8), transcript variant 2, mRNA," dated Mar. 15, 2015, 5 pages.

Hwang et al., "Budding yeast Cdc20: a target of the spindle checkpoint," Science, Feb. 1998, 279(5353):1041-1044 (abstract only).

International Preliminary Report on Patentability in International Appln. No. PCT/US2018/040890, dated Jan. 14, 2020, 6 pages.

International Search Report and Written Opinion in International Appln. No. PCT/US2018/040890, mailed Oct. 25, 2018, 8 pages.

International Search Report and Written Opinion in International Appln. No. PCT/US2022/075156, mailed Jan. 10, 2023, 13 pages.

(56) References Cited

OTHER PUBLICATIONS

Koh et al., "Visible to Near-Infrared Fluorescence Enhanced Cellular Imaging on Plasmonic Gold Chips," small, Jan. 27, 2016, 12(4):457-465 (abstract only).

Atkinson, "The pathogenesis and natural history of type 1 diabetes," Cold Spring Harb Perspect Med, Nov. 2012, 2(11):a007641, 18 pages.

Batista et al., "B cells acquire antigen from target cells after synapse formation," Nature, May 24, 2011, 411(6836):489-494.

Campbell-Thompson et al., "Insulitis and beta-Cell Mass in the Natural History of Type 1 Diabetes," Diabetes, Nov. 18, 2015, 65(3):719-731.

Cheung et al., "The Current State of Beta-Cell-Mass PET Imaging for Diabetes Research and Therapies," Biomedicines, Dec. 3, 2021, 9:1824, 14 pages.

Controlled Drug Delivery: Fundamentals and Applications, 2nd ed., Robinson et al. (eds.), 1987, Chapter 15, 32 pages.

Grinberg-Bleyer et al., "IL-2 reverses established type 1 diabetes in NOD mice by a local effect on pancreatic regulatory T cells," J. Exp. Med., Aug. 2, 2010, 207(9):1871-1878.

Guo et al., "Cell-Surface Autoantibody Targets Zinc Transporter-8 (ZnT8) for In Vivo β-Cell Imaging and Islet-Specific Therapies," Diabetes, Feb. 1, 2023, 72(2):184-195.

Hartemann et al., "Low-dose interleukin 2 in patients with type 1 diabetes: a phase 1/2 randomised, double-blind, placebo-controlled trial," Lancet Diabetes Endocrinol., Dec. 2013, 1(4):295-305.

In't Veld, "Insulitis in human type 1 diabetes: a comparison between patients and animal models," Semin. Immunopathol., Sep. 2014, 36(5):569-579.

International Preliminary Report on Patentability in International Appln. No. PCT/US2022/075156, mailed on Feb. 29, 2024, 9 pages.

Jain et al., "Targeting pancreatic B cells for diabetes treatment," Nat Metab., Sep. 2022, 4:1097-1108.

Johnson et al., "β-cell-specific IL-2 therapy increases islet Foxp3+ Treg and suppresses type 1 diabetes in NOD mice," Diabetes, Oct. 18, 2013, 62(11):3775-3784.

Kaestner et al., "NIH Initiative to Improve Understanding of the Pancreas, Islet, and Autoimmunity in Type 1 Diabetes: The Human Pancreas Analysis Program (HPAP)," Diabetes, May 24, 2019, 68(7):1394-1402.

Kahn et al., "The B cell in Diabetes: Integrating Biomarkers With Functional Measures," Endocr Rev., Jun. 28, 2021, 42:528-583.

Katsarou et al., "Type 1 diabetes mellitus," Nature Reviews Disease Primers, Mar. 30, 2017, 3:17016, 17 pages.

Kavishwar et al., "Unique sphingomyelin patches are targets of a beta-cell-specific antibody," J. Lipid Res., Sep. 2011, 52(9):1660-1671.

Khoryati et al., "An IL-2 mutein engineered to promote expansion of regulatory T cells arrests ongoing autoimmunity in mice," Sci. Immunol., Aug. 14, 2020, 5(50):eaba5264, 21 pages.

Manirarora et al.,"Combination therapy using IL-2/IL-2 monoclonal antibody complexes, rapamycin, and islet autoantigen peptides increases regulatory T cell frequency and protects against spontaneous and induced type 1 diabetes in nonobese diabetic mice," J. Immunol., Oct. 19, 2015, 195:5203-5214.

Marino et al., "B-cell cross-presentation of autologous antigen precipitates diabetes," Diabetes, Oct. 16, 2012, 61(11):2893-2905.

Milstein et al., "Hybrid hybridomas and their use in immunohistochemistry," Nature, Oct. 1983, 305(5834):537-540.

Modern Pharmaceutics, 4th ed., Banker et al. (eds.), 2002, Chapter 15, 29 pages.

Monoclonal Antibodies '84: Biological and Clinical Applications, 1st ed., Pinchera et al. (eds), 1984, 475-512.

Monoclonal Antibodies for Cancer Detection and Therapy, 1st ed., Baldwin et al.(eds.), 1985, Chapter 15, 14 pages.

Montanini et al., "Phylogenetic and functional analysis of the Cation Diffusion Facilitator (CDF) family: improved signature and prediction of substrate specificity," BMC Genomics, Apr. 23, 2007, 8:107, 16 pages.

Nayak et al., "ZnT8-reactive T cells are weakly pathogenic in NOD mice but can participate in diabetes under inflammatory conditions," Diabetes, Sep. 15, 2014, 63(10):3438-3448.

Orban et al., "Co-Stimulation Modulation with Abatacept in Patients with Recent-Onset Type 1 Diabetes: A Randomised Double-Masked Controlled Trial," Lancet, Jul. 30, 2011, 378(9789):412-419.

Reiner et al., "Accurate measurement of pancreatic islet beta-cell mass using a second-generation fluorescent exendin-4 analog," Proc. Natl. Acad. Sci. USA, Aug. 2, 2011, 108(31):12815-12820.

Rigby et al., "Alefacept provides sustained clinical and immunological effects in new-onset type 1 diabetes patients," J. Clin. Invest., Jul. 20, 2015, 125(8):3285-3296.

Rosenzwajg et al., "Low-dose IL-2 in children with recently diagnosed type 1 diabetes: a phase I/II randomised, double-blind, placebo-controlled, dose-finding study," Diabetologia, Jul. 1, 2020, 63:1808-1821.

Smith et al., "B cells in type 1 diabetes mellitus and diabetic kidney disease," Nat. Rev. Nephrol., Oct. 17, 2017, 13(11):712-720.

Sojar et al., "A chemical method for the deglycosylation of proteins," Arch Biochem Biophys., 1987, 259:52-57.

The Pharmacology of Monoclonal Antibodies, 1st ed., Rosenberg et al. (eds.), 1994, Chapter 11, 47 pages.

Uhlen et al., "Proteomics. Tissue-based map of the human proteome," Science, Jan. 23, 2015, 347(6220):1260419, 11 pages.

Wei et al., "Molecular imaging of B-cells: diabetes and beyond," Adv Drug Deliv Rev., Jan. 15, 2019, 139:16-31.

European Search Report in European Application No. 20817829.3, dated Jun. 1, 2023, 20 pages.

Gu et al., "Identification of Autoantibodies to ZnT8 Extracellular Epitope(s) in Patients with T1D," Diabetes, 79th Scientific Sessions of the American-Diabetes-Association (ADA), Jun. 7-11, 2019, 68(Suppl. 1):162-OR.

Schuit et al., Glucose stimulates proinsulin biosynthesis by a dose-dependent recruitment of pancreatic beta cells, Proc Natl Acad Sci USA, (1988), pp. 3865-386, 85 (11).

Dodson et al., The role of assembly in insulin's biosynthesis, Curr Opin Struct Biol, (1998), pp. 189-194, 8 (2).

Foster et al., Elemental composition of secretory granules in pancreatic islets of Langerhans, Biophys J, (1993), pp. 525-532, 64 (2).

Vinkenborg et al., Genetically encoded FRET sensors to monitor intracellular Zn2+ homeostasis, Nat Methods, (2009), pp. 737-740, 6 (10).

Huang, Zinc and its transporters, pancreatic beta-cells, and insulin metabolism, Vitam Horm, (2014), pp. 365-390, 95.

Kambe et al., Current understanding of ZIP and ZnT zinc transporters in human health and diseases, Cell Mol Life Sci, (2014), pp. 3281-3295, 71 (17).

Lemaire et al., Zinc transporters and their role in the pancreatic beta-cell, J Diabetes Investig, (2012), pp. 202-211, 3(3).

Segerstolpe et al., Single-Cell Transcriptome Profiling of Human Pancreatic Islets in Health and Type 2 Diabetes, Cell Metab, (2016), pp. 593-607, 24 (4).

Wenzlau et al., The cation efflux transporter ZnT8 (Slc30A8) is a major autoantigen in human type 1 diabetes, Proc Natl Acad Sci USA, (2007), pp. 17040-17045, 104 (43).

Enee et al., ZnT8 is a major CD8+ T cell-recognized autoantigen in pediatric type 1 diabetes, Diabetes, (2012), pp. 1779-1784, 61 (7).

Sladek et al., A genome-wide association study identifies novel risk loci for type 2 diabetes, Nature, (2007), pp. 881-885, 445 (7130).

Flannick et al., Loss-of-function mutations in SLC30A8 protect against type 2 diabetes, Nat Genet, (2014), pp. 357-363, 46 (4).

Nicolson et al., Insulin storage and glucose homeostasis in mice null for the granule zinc transporter ZnT8 and studies of the type 2 diabetes-associated variants, Diabetes, (2009), pp. 2070-2083, 58 (9).

Wijesekara et al., Beta cell-specific Znt8 deletion in mice causes marked defects in insulin processing, crystallisation and secretion, Diabetologia, (2010), pp. 1656-1668, 53 (8).

Pound et al., Deletion of the mouse Slc30a8 gene encoding zinc transporter-8 results in impaired insulin secretion, Biochem J, (2009), pp. 371-376, 421 (3).

(56) References Cited

OTHER PUBLICATIONS

Lemaire et al., Insulin crystallization depends on zinc transporter ZnT8 expression, but is not required for normal glucose homeostasis in mice, Proc Natl Acad Sci USA, (2009), pp. 14872-14877, 106 (35).

Pound et al., The physiological effects of deleting the mouse SLC30A8 gene encoding zinc transporter-8 are Influenced by gender and genetic background, PLoS One, (2012), e40972, 7 (7).

Chabosseau et al., Zinc and diabetes, Arch Biochem Biophys, (2016), pp. 79-85, 611.

Saltiel et al., Inflammatory mechanisms linking obesity and metabolic disease, J Clin Invest, (2017), pp. 1-4, 127 (1).

Leahy et al., Chronic hyperglycemia is associated with impaired glucose influence on insulin secretion. A study in normal rats using chronic in vivo glucose infusions, J Clin Invest, (1986), pp. 908-915, 77 (3).

Maedler et al., Distinct effects of saturated and monounsaturated fatty acids on betacell turnover and function, Diabetes, (2001), pp. 69-76, 50 (1).

Poitout et al., Glucolipotoxicity: fuel excess and beta-cell dysfunction, Endocr Rev, (2008), pp. 351-366, 29 (3).

Butcher et al., Association of proinflammatory cytokines and islet resident leucocytes with islet dysfunction in type 2 diabetes, Diabetologia, (2014), pp. 491-501, 57 (3).

Hotamisligil et al., Inflammation, metaflammation and immunometabolic disorders, Nature, (2017), pp. 177-185, 542 (7640).

Donath et al., Type 2 diabetes as an inflammatory disease, Nat Rev Immunol, (2011), pp. 98-107, 11 (2).

Tsai et al., Are obesity-related insulin resistance and type 2 diabetes autoimmune diseases?, Diabetes, (2015), pp. 1886-1897, 64 (6).

Zumsteg et al., Nitric oxide production and Fas surface expression mediate two independent pathways of cytokine-induced murine beta-cell damage, Diabetes, (2000), pp. 39-47, 49 (1).

Robertson et al., Beta-cell glucose toxicity, lipotoxicity, and chronic oxidative stress in type 2 diabetes, Diabetes, (2004), pp. S119-124, 53 Suppl 1.

Eide, The oxidative stress of zinc deficiency, Metallomics, (2011), pp. 1124-1129, 3 (11).

Homma et al., SOD1 as a molecular switch for initiating the homeostatic ER stress response under zinc deficiency, Mol Cell, (2013), pp. 75-86, 52 (1).

Fonseca et al., Endoplasmic reticulum stress in beta-cells and development of diabetes, Curr Opin Pharmacol, (2009), pp. 763-770, 9 (6).

Merriman et al., Highly specific monoclonal antibodies for allosteric inhibition and immunodetection of the human pancreatic zinc transporter ZnT8, J Biol Chem, (2018), pp. 16206-16216, 293 (42).

Merriman et al., A subclass of serum anti-ZnT8 antibodies directed to the surface of live pancreatic beta-cells, J Biol Chem, (2018), pp. 579-587, 293 (2).

Merriman et al., Lipid-tuned Zinc Transport Activity of Human ZnT8 Protein Correlates with Risk for Type-2 Diabetes, J Biol Chem, (2016), pp. 26950-26957, 291 (53).

Poitout et al., Glucolipotoxicity of the pancreatic beta cell, Biochim Biophys Acta, (2010), pp. 289-298, 1801 (3).

Eizirik et al., The role of inflammation in insulitis and beta-cell loss in type 1 diabetes, Nat Rev Endocrinol, (2009), pp. 219-226, 5 (4).

Hakonen et al., MANF protects human pancreatic beta cells against stress-induced cell death, Diabetologia, (2018), pp. 2202-2214, 61 (10).

Gurgul-Convey et al., Sensitivity profile of the human EndoC-betaH1 beta cell line to proinflammatory cytokines, Diabetologia, (2016), pp. 2125-2133, 59 (10).

Thul et al., A subcellular map of the human proteome, Science, (2017), eaal3321, 356 (6340).

Davidson et al., Zinc transporter 8 (ZnT8) and beta cell function, Trends Endocrinol Metab, (2014), pp. 415-424, 25 (8).

Chimienti et al., Identification and cloning of a beta-cell-specific zinc transporter, ZnT-8, localized into insulin secretory granules, Diabetes, (2004), pp. 2330-2337, 53 (9).

Solimena et al., ICA 512, an autoantigen of type I diabetes, is an intrinsic membrane protein of neurosecretory granules, EMBO J, (1996), pp. 2102-2114, 15 (9).

Regazzi et al., VAMP-2 and cellubrevin are expressed in pancreatic beta-cells and are essential for Ca(2+)—but not for GTP gamma S-induced insulin secretion, EMBO J, (1995), pp. 2723-2730, 14 (12).

Kay et al., Overexpression of class I major histocompatibility complex accompanies insulitis in the nonobese diabetic mouse and is prevented by anti-interferon-gamma antibody, Diabetologia, (1991), pp. 779-785, 34 (11).

Scheuner et al., The unfolded protein response: a pathway that links insulin demand with beta-cell failure and diabetes, Endocr Rev, (2008), pp. 317-333, 29 (3).

Farino et al., Development of a Rapid Insulin Assay by Homogenous Time-Resolved Fluorescence, PLoS One, (2016), e0148684, 11 (2).

Kharroubi et al., Free fatty acids and cytokines induce pancreatic beta-cell apoptosis by different mechanisms: role of nuclear factor-kappaB and endoplasmic reticulum stress, Endocrinology, (2004), pp. 5087-5096, 145 (11).

Akerfeldt et al., Cytokine-induced beta-cell death is independent of endoplasmic reticulum stress signaling, Diabetes, (2008), pp. 3034-3044, 57 (11).

Cnop et al., Mechanisms of pancreatic beta-cell death in type 1 and type 2 diabetes: many differences, few similarities, Diabetes, (2005), pp. S97-107, 54 Suppl 2.

Li et al., Temporal Proteomic Analysis of Pancreatic beta-Cells in Response to Lipotoxicity and Glucolipotoxicity, Mol Cell Proteomics, (2018), pp. 2119-2131, 17 (11).

\* cited by examiner

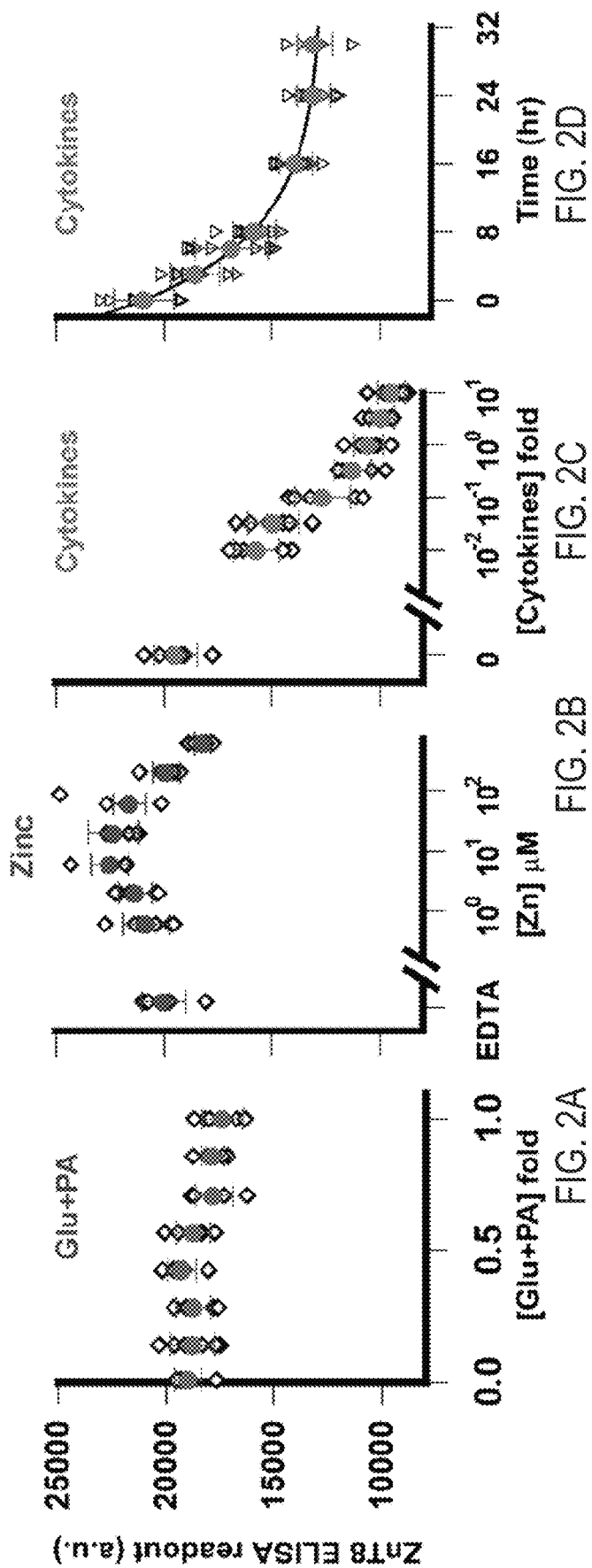

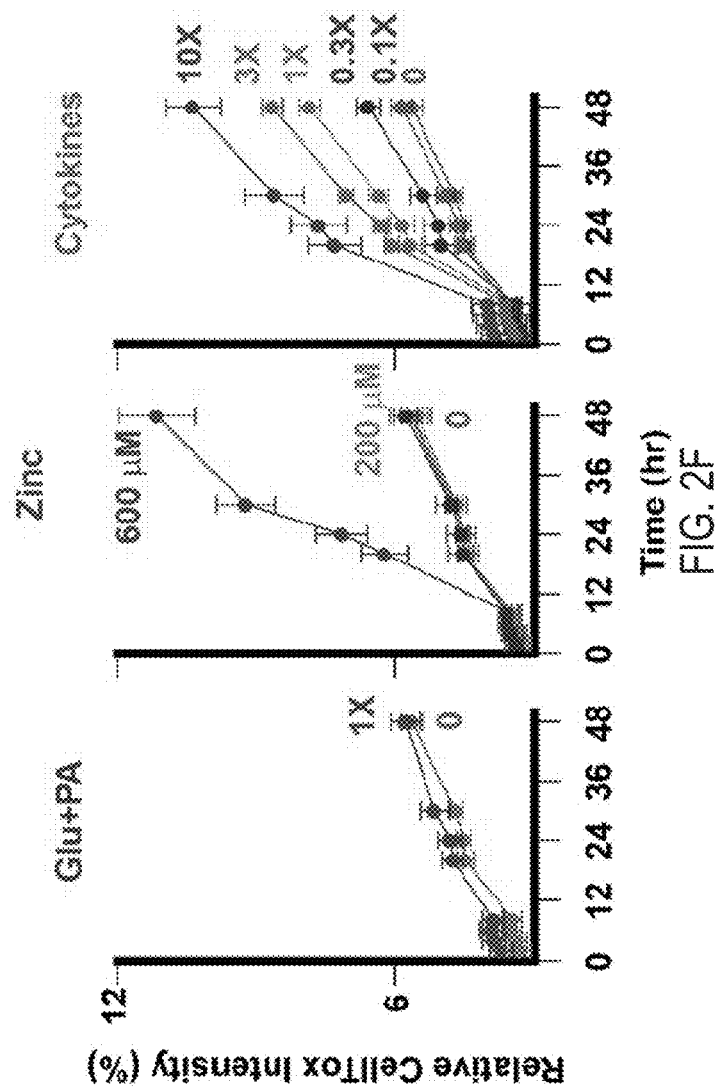
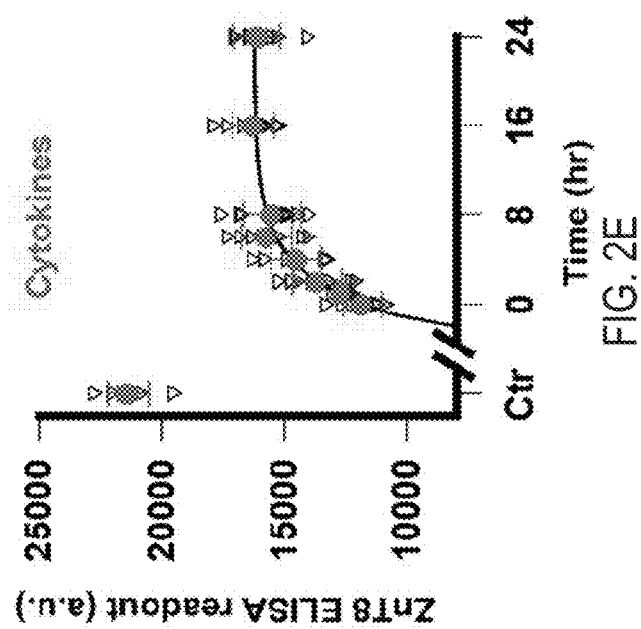
FIG. 2E
FIG. 2F

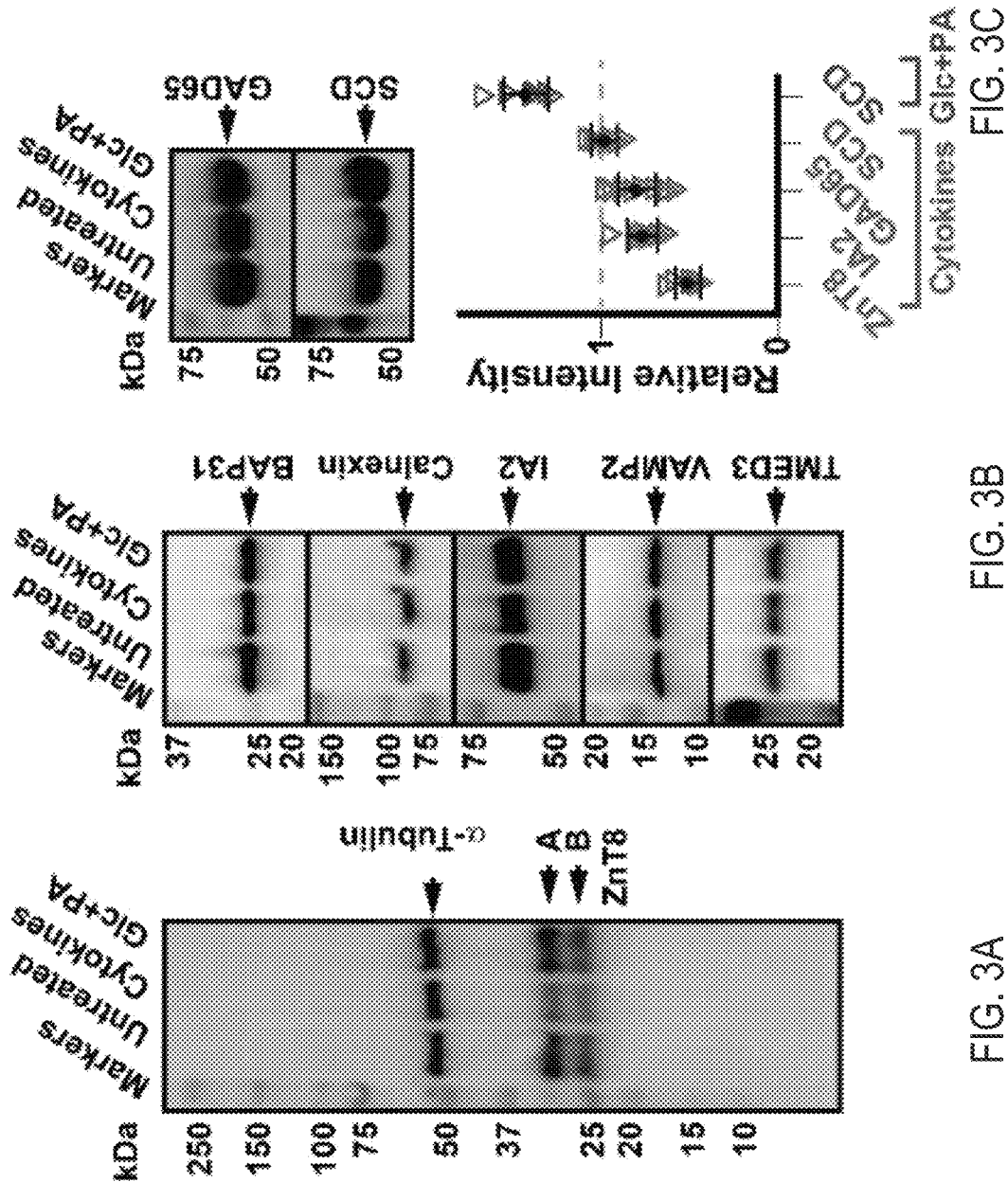

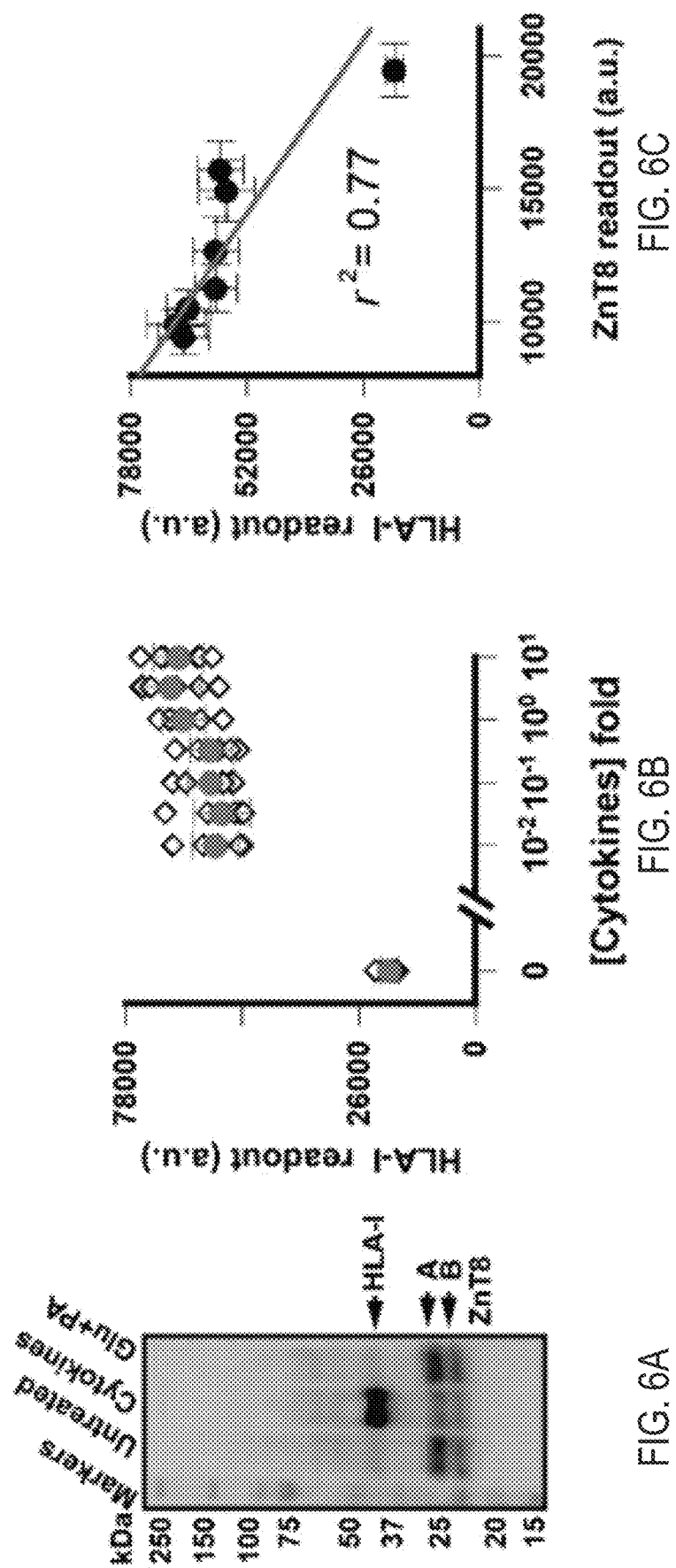

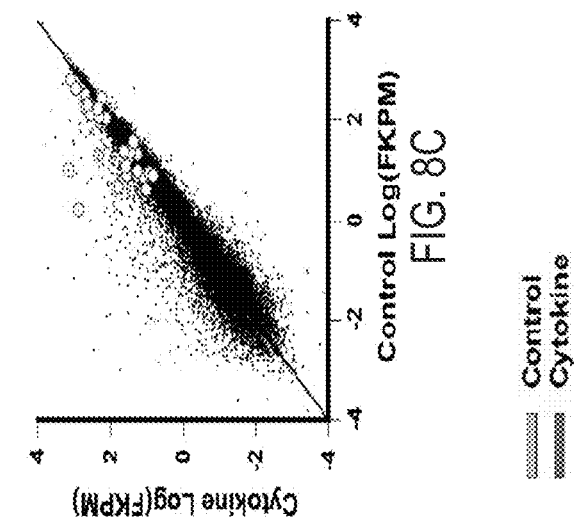
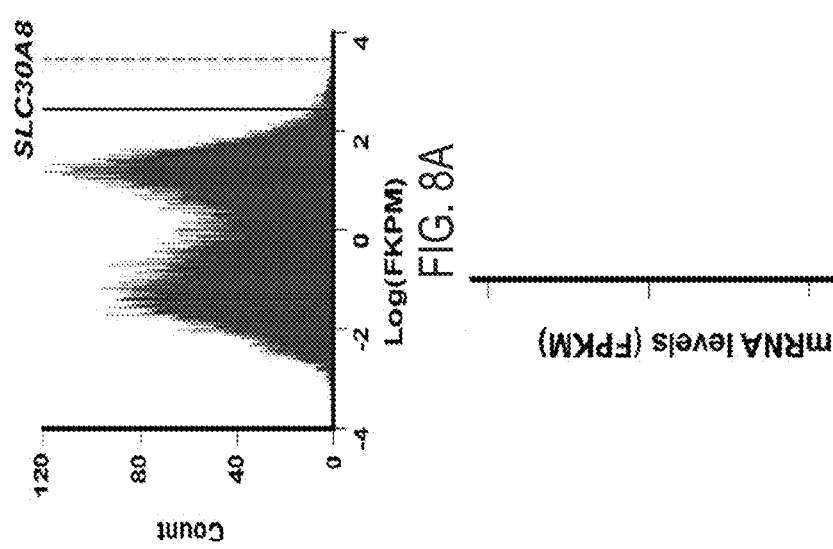
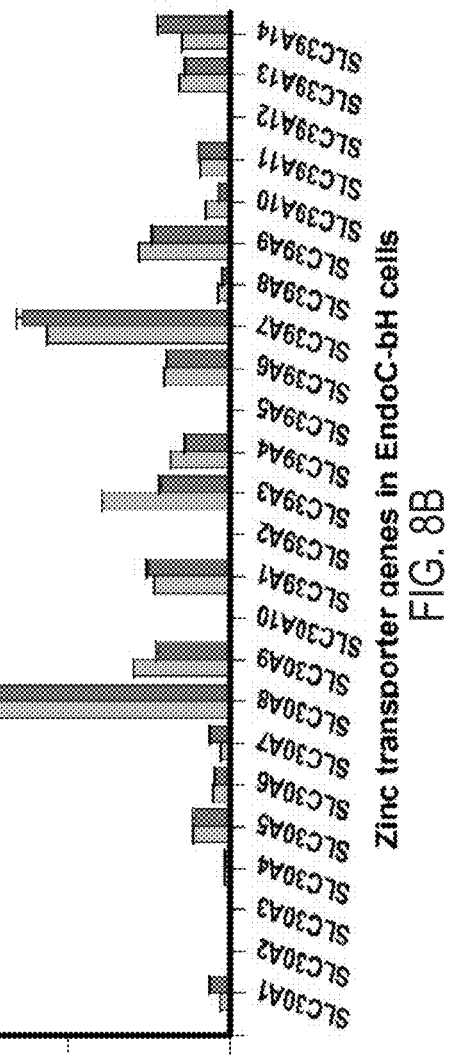

SEQUENCE LISTING

```
<160> NUMBER OF SEQ ID NOS: 64

<210> SEQ ID NO 1
<211> LENGTH: 1404
<212> TYPE: DNA
<213> ORGANISM: Artificial Sequence
<220> FEATURE:
<223> OTHER INFORMATION: mAB12 heavy chain

<400> SEQUENCE: 1
atggacatga gggtgcccgc tcagctcctg gggctcctgc tgctgtggct gagaggtgcg      60
cgctgtcaga tccagttggt gcagtctgga cctgagctga agaagcctgg agagacagtc     120
aagatctcct gcaaggcttc tgggtatacc ttcacaaact atccaatgca ctgggtgaag     180
cagactccag gaaagggttt aaagtggatg ggctggataa acacctactc tggagtgcca     240
acatatgagg atgacttcaa gggacggttt gccttctctt tggaaacctc tgccagtact     300
gcatatttgc agatcaacaa cctcaaaaat gaagacatgg ctacatattt ctgtgcaaga     360
tcgaaccccg atgattactt gtatgctatg gactcctggg gtcaaggaac ctcagtcacc     420
gtctctagtg ccaaaacgac accccatct gtctaccac tggcccctgg atctgctgcc      480
```

-continued

```
caaactaact ccatggtgac cctgggatgc ctggtcaagg gctatttccc tgagccagtg      540
acagtgacct ggaactctgg atccctgtcc agcggtgtgc acaccttccc agctgtcctg      600
cagtctgacc tctacactct gagcagctca gtgactgtcc cctccagcac ctggcccagc      660
gagaccgtca cctgcaacgt tgcccacccg gccagcagca ccaaggtgga caagaaaatt      720
gtgcccaggg attgtggttg taagccttgc atatgtacag tcccagaagt atcatctgtc      780
ttcatcttcc ccccaaagcc caaggatgtg ctcaccatta ctctgactcc taaggtcacg      840
tgtgttgtgg tagacatcag caaggatgat cccgaggtcc agttcagctg gtttgtagat      900
gatgtggagg tgcacacagc tcagacgcaa ccccgggagg agcagttcaa cagcactttc      960
cgctcagtca gtgaacttcc catcatgcac caggactggc tcaatggcaa ggagttcaaa     1020
tgcagggtca acagtgcagc tttccctgcc cccatcgaga aaaccatctc caaaaccaaa     1080
ggcagaccga aggctccaca ggtgtacacc attccacctc ccaaggagca gatggccaag     1140
gataaagtca gtctgacctg catgataaca gacttcttcc ctgaagacat tactgtggag     1200
tggcagtgga atgggcagcc agcggagaac tacaagaaca ctcagcccat catggacaca     1260
gatggctctt acttcgtcta cagcaagctc aatgtgcaga gagcaactg ggaggcagga      1320 aatactttca cctgctctgt gttacatgag ggcctgcaca accaccatac tgagaagagc     1380
ctctcccact ctcctggtaa atga                                            1404
```

```
<210> SEQ ID NO 2
<211> LENGTH: 467
<212> TYPE: PRT
<213> ORGANISM: Artificial Sequence
<220> FEATURE:
<223> OTHER INFORMATION: mAB12 heavy chain

<400> SEQUENCE: 2

Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Pro Met His Trp Val Lys Gln Thr Pro Gly
    50                  55                  60

Lys Gly Leu Lys Trp Met Gly Trp Ile Asn Thr Tyr Ser Gly Val Pro
65                  70                  75                  80

Thr Tyr Gly Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
            100                 105                 110

Met Ala Thr Tyr Phe Cys Ala Arg Ser Asn Pro Tyr Asp Tyr Leu Tyr
        115                 120                 125

Ala Met Asp Ser Trp Gly Gln Gly Thr Ser Val Thr Val Ser Ser Ala
    130                 135                 140

Lys Thr Thr Pro Pro Ser Val Tyr Pro Leu Ala Pro Gly Ser Ala Ala
145                 150                 155                 160

Gln Thr Asn Ser Met Val Thr Leu Gly Cys Leu Val Lys Gly Tyr Phe
                165                 170                 175

Pro Glu Pro Val Thr Val Thr Trp Asn Ser Gly Ser Leu Ser Ser Gly
            180                 185                 190
```

-continued

```
Val His Thr Phe Pro Ala Val Leu Gln Ser Asp Leu Tyr Thr Leu Ser
        195                 200                 205
Ser Ser Val Thr Val Pro Ser Ser Thr Trp Pro Ser Glu Thr Val Thr
    210                 215                 220
Cys Asn Val Ala His Pro Ala Ser Ser Thr Lys Val Asp Lys Lys Ile
225                 230                 235                 240
Val Pro Arg Asp Cys Gly Cys Lys Pro Cys Ile Cys Thr Val Pro Glu
            245                 250                 255
Val Ser Ser Val Phe Ile Phe Pro Pro Lys Pro Lys Asp Val Leu Thr
        260                 265                 270
Ile Thr Leu Thr Pro Lys Val Thr Cys Val Val Val Asp Ile Ser Lys
    275                 280                 285
Asp Asp Pro Glu Val Gln Phe Ser Trp Phe Val Asp Asp Val Glu Val
290                 295                 300
His Thr Ala Gln Thr Gln Pro Arg Glu Glu Gln Phe Asn Ser Thr Phe
305                 310                 315                 320
Arg Ser Val Ser Glu Leu Pro Ile Met His Gln Asp Trp Leu Asn Gly
            325                 330                 335
Lys Glu Phe Lys Cys Arg Val Asn Ser Ala Ala Phe Pro Ala Pro Ile
        340                 345                 350
Glu Lys Thr Ile Ser Lys Thr Lys Gly Arg Pro Lys Ala Pro Gln Val
    355                 360                 365
Tyr Thr Ile Pro Pro Pro Lys Glu Gln Met Ala Lys Asp Lys Val Ser
370                 375                 380
Leu Thr Cys Met Ile Thr Asp Phe Phe Pro Glu Asp Ile Thr Val Glu
385                 390                 395                 400
Trp Gln Trp Asn Gly Gln Pro Ala Glu Asn Tyr Lys Asn Thr Gln Pro
            405                 410                 415
Ile Met Asp Thr Asp Gly Ser Tyr Phe Val Tyr Ser Lys Leu Asn Val
        420                 425                 430
Gln Lys Ser Asn Trp Glu Ala Gly Asn Thr Phe Thr Cys Ser Val Leu
    435                 440                 445
His Glu Gly Leu His Asn His His Thr Glu Lys Ser Leu Ser His Ser
450                 455                 460
Pro Gly Lys
465

<210> SEQ ID NO 3
<211> LENGTH: 7
<212> TYPE: PRT
<213> ORGANISM: Artificial Sequence
<220> FEATURE:
<223> OTHER INFORMATION: mAb12 heavy chain CDR1

<400> SEQUENCE: 3

Gly Tyr Thr Phe Thr Asn Tyr
1               5

<210> SEQ ID NO 4
<211> LENGTH: 5
<212> TYPE: PRT
<213> ORGANISM: Artificial Sequence
<220> FEATURE:
<223> OTHER INFORMATION: mAb12 heavy chain CDR2

<400> SEQUENCE: 4

Thr Tyr Ser Gly Val
1               5
```

<210> SEQ ID NO 5
<211> LENGTH: 12
<212> TYPE: PRT
<213> ORGANISM: Artificial Sequence
<220> FEATURE:
<223> OTHER INFORMATION: mAB heavy chain CDR3

<400> SEQUENCE: 5

Ser Asn Pro Tyr Asp Tyr Leu Tyr Ala Met Asp Ser
1               5                   10

<210> SEQ ID NO 6
<211> LENGTH: 726
<212> TYPE: DNA
<213> ORGANISM: Artificial Sequence
<220> FEATURE:
<223> OTHER INFORMATION: mAb12 light chain

<400> SEQUENCE: 6
atggacatga gggtgcccgc tcagctcctg gggctcctgc tgctgtggct gagaggtgcg    60
cgctgtgatg ttgtgatgac ccaaactcca ctctccctgc ctgtcagtct tggagatcaa   120
gcctccatct cctgcagatc tagtcagagc cttgtacaca tcaatggaaa cacctatata   180
cattggtacc tgcagaagcc aggccagtct ccaaagctcc tgatctacaa agtttccaac   240
cgattttctg ggtcccaga caggttcagt ggcagtggat cagggacaga ttttacactc   300
aagatcagaa gagtggaggc tgaggatctg ggagtttatt tctgctctca aaatacacat   360
gttccattca cattcggctc ggggacaaag ttggaaataa aacgtgcaga tgctgcgcca   420
actgtatcca tcttcccacc atctagcgag cagttaacat ctggaggtgc ctcagtcgtg   480
tgcttcttga caacttcta ccccaaagac atcaatgtca gtggaagat tgatggcagt   540 gaacgacaaa atggcgtcct gaacagttgg actgatcagg acagcaaaga cagcacctac   600
agcatgagca gcaccctcac gttgaccaag gacgagtatg aacgacataa cagctatacc   660
tgtgaggcca ctcacaagac atcaacttca cccattgtca agagcttcaa caggaatgag   720
tgttag                                                              726

<210> SEQ ID NO 7
<211> LENGTH: 241
<212> TYPE: PRT
<213> ORGANISM: Artificial Sequence
<220> FEATURE:
<223> OTHER INFORMATION: mAb12 light chain

<400> SEQUENCE: 7

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Thr Pro Leu Ser
                20                  25                  30

Leu Pro Val Ser Leu Gly Asp Gln Ala Ser Ile Ser Cys Arg Ser Ser
            35                  40                  45

Gln Ser Leu Val His Ile Asn Gly Asn Thr Tyr Ile His Trp Tyr Leu
        50                  55                  60

Gln Lys Pro Gly Gln Ser Pro Lys Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Arg Arg Val Glu Ala Glu Asp Leu Gly Val

```
                    100                 105                 110
Tyr Phe Cys Ser Gln Asn Thr His Val Pro Phe Thr Phe Gly Ser Gly
            115                 120                 125

Thr Lys Leu Glu Ile Lys Arg Ala Asp Ala Ala Pro Thr Val Ser Ile
            130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
            195                 200                 205

Thr Lys Asp Glu Tyr Glu Arg His Asn Ser Tyr Thr Cys Glu Ala Thr
            210                 215                 220

His Lys Thr Ser Thr Ser Pro Ile Val Lys Ser Phe Asn Arg Asn Glu
225                 230                 235                 240

Cys

<210> SEQ ID NO 8
<211> LENGTH: 16
<212> TYPE: PRT
<213> ORGANISM: Artificial Sequence
<220> FEATURE:
<223> OTHER INFORMATION: mAb12 light chain CDR1

<400> SEQUENCE: 8

Arg Ser Ser Gln Ser Leu Val His Ile Asn Gly Asn Thr Tyr Ile His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: mAb12 light chain CDR2

<400> SEQUENCE: 9

Lys Val Ser Asn Arg Phe Ser
1               5

<210> SEQ ID NO 10
<211> LENGTH: 9
<212> TYPE: PRT
<213> ORGANISM: Artificial Sequence
<220> FEATURE:
<223> OTHER INFORMATION: mAb12 light chain CDR3

<400> SEQUENCE: 10

Ser Gln Asn Thr His Val Pro Phe Thr
1               5

<210> SEQ ID NO 11
<211> LENGTH: 1401
<212> TYPE: DNA
<213> ORGANISM: Artificial Sequence
<220> FEATURE:
<223> OTHER INFORMATION: mAb16 heavy chain

<400> SEQUENCE: 11
atggacatga gggtgcccgc tcagctcctg gggctcctgc tgctgtggct gagaggtgcg    60
```

```
cgctgtcaga tccagttggt gcagtctgga cctgagctga agaagcctgg agagacagtc      120
acgatctcct gcaaggcttc tggatatacc ttcacacact atccagtgca ctgggtgaag      180
caggctccag gaaagggttt acagtggatg ggctggataa acacctactc tggagtgcca      240
acatatgcag atgccttcaa gaaacgtttt gccttctctt tggaaacctc tgccagcact      300
gcatatttgc agatcaacaa cctcaaaagt gaggacatgg ctacatattt ctgtgcaaga      360
tcgagggtct atgatgggta ctattttgac tactggggcc aaggcaccac tctcaccgtc      420
tctagtgcca aaacgacacc cccatctgtc tacccactgg cccctggatc tgctgcccaa      480
actaactcca tggtgaccct gggatgcctg gtcaagggct atttccctga gccagtgaca      540
gtgacctgga actctggatc cctgtccagc ggtgtgcaca ccttcccagc tgtcctgcag      600
tctgacctct acactctgag cagctcagtg actgtcccct ccagcacctg gcccagcgag      660
accgtcacct gcaacgttgc ccacccggcc agcagcacca aggtggacaa gaaaattgtg      720
cccagggatt gtggttgtaa gccttgcata tgtacagtcc cagaagtatc atctgtcttc      780
atcttccccc caaagcccaa ggatgtgctc accattactc tgactcctaa ggtcacgtgt      840
gttgtggtag acatcagcaa ggatgatccc gaggtccagt tcagctggtt tgtagatgat      900
gtggaggtgc acacagctca gacgcaaccc cgggaggagc agttcaacag cactttccgc      960
tcagtcagtg aacttcccat catgcaccag gactggctca atggcaagga gttcaaatgc     1020
agggtcaaca gtgcagcttt ccctgccccc atcgagaaaa ccatctccaa aaccaaaggc     1080
agaccgaagg ctccacaggt gtacaccatt ccacctccca aggagcagat ggccaaggat     1140
aaagtcagtc tgacctgcat gataacagac ttcttccctg aagacattac tgtggagtgg     1200
cagtggaatg ggcagccagc ggagaactac aagaacactc agcccatcat ggacacagat     1260
ggctcttact tcgtctacag caagctcaat gtgcagaaga caactgggaa ggcaggaaat     1320
actttcacct gctctgtgtt acatgagggc ctgcacaacc accatactga gaagagcctc     1380
tcccactctc ctggtaaatg a                                               1401

<210> SEQ ID NO 12
<211> LENGTH: 466
<212> TYPE: PRT
<213> ORGANISM: Artificial Sequence
<220> FEATURE:
<223> OTHER INFORMATION: mAb16 heavy chain

<400> SEQUENCE: 12

Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Thr Ile Ser Cys Lys Ala Ser Gly
        35                  40                  45

Tyr Thr Phe Thr His Tyr Pro Val His Trp Val Lys Gln Ala Pro Gly
    50                  55                  60

Lys Gly Leu Gln Trp Met Gly Trp Ile Asn Thr Tyr Ser Gly Val Pro
65                  70                  75                  80

Thr Tyr Ala Asp Ala Phe Lys Lys Arg Phe Ala Phe Ser Leu Glu Thr
                85                  90                  95

Ser Ala Ser Thr Ala Tyr Leu Gln Ile Asn Asn Leu Lys Ser Glu Asp
            100                 105                 110

Met Ala Thr Tyr Phe Cys Ala Arg Ser Arg Val Tyr Asp Gly Tyr Tyr
        115                 120                 125
```

```
Phe Asp Tyr Trp Gly Gln Gly Thr Thr Leu Thr Val Ser Ser Ala Lys
        130                 135                 140
Thr Thr Pro Pro Ser Val Tyr Pro Leu Ala Pro Gly Ser Ala Ala Gln
145                 150                 155                 160
Thr Asn Ser Met Val Thr Leu Gly Cys Leu Val Lys Gly Tyr Phe Pro
                165                 170                 175
Glu Pro Val Thr Val Thr Trp Asn Ser Gly Ser Leu Ser Ser Gly Val
            180                 185                 190
His Thr Phe Pro Ala Val Leu Gln Ser Asp Leu Tyr Thr Leu Ser Ser
        195                 200                 205
Ser Val Thr Val Pro Ser Ser Thr Trp Pro Ser Glu Thr Val Thr Cys
    210                 215                 220
Asn Val Ala His Pro Ala Ser Ser Thr Lys Val Asp Lys Lys Ile Val
225                 230                 235                 240
Pro Arg Asp Cys Gly Cys Lys Pro Cys Ile Cys Thr Val Pro Glu Val
                245                 250                 255
Ser Ser Val Phe Ile Phe Pro Pro Lys Pro Lys Asp Val Leu Thr Ile
            260                 265                 270
Thr Leu Thr Pro Lys Val Thr Cys Val Val Val Asp Ile Ser Lys Asp
        275                 280                 285
Asp Pro Glu Val Gln Phe Ser Trp Phe Val Asp Asp Val Glu Val His
    290                 295                 300
Thr Ala Gln Thr Gln Pro Arg Glu Glu Gln Phe Asn Ser Thr Phe Arg
305                 310                 315                 320
Ser Val Ser Glu Leu Pro Ile Met His Gln Asp Trp Leu Asn Gly Lys
                325                 330                 335
Glu Phe Lys Cys Arg Val Asn Ser Ala Ala Phe Pro Ala Pro Ile Glu
            340                 345                 350
Lys Thr Ile Ser Lys Thr Lys Gly Arg Pro Lys Ala Pro Gln Val Tyr
        355                 360                 365
Thr Ile Pro Pro Pro Lys Glu Gln Met Ala Lys Asp Lys Val Ser Leu
    370                 375                 380
Thr Cys Met Ile Thr Asp Phe Phe Pro Glu Asp Ile Thr Val Glu Trp
385                 390                 395                 400
Gln Trp Asn Gly Gln Pro Ala Glu Asn Tyr Lys Asn Thr Gln Pro Ile
                405                 410                 415
Met Asp Thr Asp Gly Ser Tyr Phe Val Tyr Ser Lys Leu Asn Val Gln
            420                 425                 430
Lys Ser Asn Trp Glu Ala Gly Asn Thr Phe Thr Cys Ser Val Leu His
        435                 440                 445
Glu Gly Leu His Asn His His Thr Glu Lys Ser Leu Ser His Ser Pro
    450                 455                 460
Gly Lys
465

<210> SEQ ID NO 13
<211> LENGTH: 7
<212> TYPE: PRT
<213> ORGANISM: Artificial Sequence
<220> FEATURE:
<223> OTHER INFORMATION: mAb16 heavy chain CDR1

<400> SEQUENCE: 13

Gly Tyr Thr Phe Thr His Tyr
1               5
```

<210> SEQ ID NO 14
<211> LENGTH: 6
<212> TYPE: PRT
<213> ORGANISM: Artificial Sequence
<220> FEATURE:
<223> OTHER INFORMATION: mAb16 heavy chain CDR2

<400> SEQUENCE: 14

Asn Thr Tyr Ser Gly Val
1               5

<210> SEQ ID NO 15
<211> LENGTH: 11
<212> TYPE: PRT
<213> ORGANISM: Artificial Sequence
<220> FEATURE:
<223> OTHER INFORMATION: mAb16 heavy chain CDR3

<400> SEQUENCE: 15

Ser Arg Val Tyr Asp Gly Tyr Tyr Phe Asp Tyr
1               5                   10

<210> SEQ ID NO 16
<211> LENGTH: 726
<212> TYPE: DNA
<213> ORGANISM: Artificial Sequence
<220> FEATURE:
<223> OTHER INFORMATION: mAb16 light chain

<400> SEQUENCE: 16

```
atggacatga gggtgcccgc tcagctcctg gggctcctgc tgctgtggct gagaggtgcg      60
cgctgtgatg ttgtgatgac ccaaactcca ctctccctgc tgtcagtct  tggagatcaa     120 gcctccatct cttgcagatc tagtcagagc cttgtacaca gtaatggaaa gacctattta     180
cattggtacc tgcagaagcc aggccagtct ccaaacctcc tgatctacaa agtttccaac     240
cgattttctg ggtcccaga  caggttcagt ggcagtggat cagggacaga tttcacactc     300
aagatcagca gagtggaggc tgaggatctg ggagtttatt tctgctctca acttacacat     360
gttccgtgga cgttcggtgg aggcaccaag ctggaaatca acgtgcaga  tgctgcgcca     420 actgtatcca tcttcccacc atctagcgag cagttaacat ctggaggtgc ctcagtcgtg     480
tgcttcttga caacttcta  ccccaaagac atcaatgtca gtggaagat  tgatggcagt     540 gaacgacaaa atggcgtcct gaacagttgg actgatcagg acagcaaaga cagcacctac     600
agcatgagca gcaccctcac gttgaccaag gacgagtatg aacgacataa cagctatacc     660
tgtgaggcca ctcacaagac atcaacttca cccattgtca agagcttcaa caggaatgag     720
tgttag                                                                726
```

<210> SEQ ID NO 17
<211> LENGTH: 241
<212> TYPE: PRT
<213> ORGANISM: Artificial Sequence
<220> FEATURE:
<223> OTHER INFORMATION: mAb16 light chain

<400> SEQUENCE: 17

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Thr Pro Leu Ser
            20                  25                  30

```
Leu Pro Val Ser Leu Gly Asp Gln Ala Ser Ile Ser Cys Arg Ser Ser
            35                  40                  45
Gln Ser Leu Val His Ser Asn Gly Lys Thr Tyr Leu His Trp Tyr Leu
 50                  55                  60
Gln Lys Pro Gly Gln Ser Pro Asn Leu Leu Ile Tyr Lys Val Ser Asn
 65                  70                  75                  80
Arg Phe Ser Gly Val Pro Asp Arg Phe Ser Gly Ser Gly Ser Gly Thr
                 85                  90                  95
Asp Phe Thr Leu Lys Ile Ser Arg Val Glu Ala Glu Asp Leu Gly Val
            100                 105                 110
Tyr Phe Cys Ser Gln Leu Thr His Val Pro Trp Thr Phe Gly Gly Gly
            115                 120                 125
Thr Lys Leu Glu Ile Lys Arg Ala Asp Ala Ala Pro Thr Val Ser Ile
130                 135                 140
Phe Pro Pro Ser Ser Glu Gln Leu Thr Ser Gly Gly Ala Ser Val Val
145                 150                 155                 160
Cys Phe Leu Asn Asn Phe Tyr Pro Lys Asp Ile Asn Val Lys Trp Lys
                165                 170                 175
Ile Asp Gly Ser Glu Arg Gln Asn Gly Val Leu Asn Ser Trp Thr Asp
            180                 185                 190
Gln Asp Ser Lys Asp Ser Thr Tyr Ser Met Ser Ser Thr Leu Thr Leu
            195                 200                 205
Thr Lys Asp Glu Tyr Glu Arg His Asn Ser Tyr Thr Cys Glu Ala Thr
210                 215                 220
His Lys Thr Ser Thr Ser Pro Ile Val Lys Ser Phe Asn Arg Asn Glu
225                 230                 235                 240
Cys

<210> SEQ ID NO 18
<211> LENGTH: 16
<212> TYPE: PRT
<213> ORGANISM: Artificial Sequence
<220> FEATURE:
<223> OTHER INFORMATION: mAb16 light chain CDR1

<400> SEQUENCE: 18

Arg Ser Ser Gln Ser Leu Val His Ser Asn Gly Lys Thr Tyr Leu His
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: mAb16 light chain CDR2

<400> SEQUENCE: 19

Lys Val Ser Asn Arg Phe Ser
1               5

<210> SEQ ID NO 20
<211> LENGTH: 8
<212> TYPE: PRT
<213> ORGANISM: Artificial Sequence
<220> FEATURE:
<223> OTHER INFORMATION: mAb16 light chain CDR3

<400> SEQUENCE: 20

Ser Gln Leu Thr His Val Pro Trp
1               5
```

<210> SEQ ID NO 21
<211> LENGTH: 1407
<212> TYPE: DNA
<213> ORGANISM: Artificial Sequence
<220> FEATURE:
<223> OTHER INFORMATION: mAb17 heavy chain

<400> SEQUENCE: 21

```
atggacatga gggtgcccgc tcagctcctg gggctcctgc tgctgtggct gagaggtgcg      60
cgctgtcaga tccagttggt gcagtctgga cctgagctga agaagcctgg agagacagtc     120
aagatctcct gcaaggcttc tgggtatacc ttcacaaact atccaatgca ctggttgaag     180
caggctccag gaaagggttt aaagtggatg gctggataa acacctactc tggagtgcca     240
acatatgcag atgacttcaa gggacggttt gccttctctt tggaaacctc tgccagcact     300
gcatatttgc agatcaacaa cctcaaaaat gaggacatgg ctacatattt ctgtacaaaa     360
tcgcgcatta ctacgatggg gggttatgct atggactgct ggggtcaagg aacctcagtc     420
accgtctcta gtgccaaaac gacaccccca tctgtctacc cactggcccc tggatctgct     480
gcccaaacta actccatggt gaccctggga tgcctggtca aggctatttt ccctgagcca     540
gtgacagtga cctggaactc tggatccctg tccagcggtg tgcacacctt cccagctgtc     600
ctgcagtctg acctctacac tctgagcagc tcagtgactg tcccctccag cacctggccc     660
agcgagaccg tcacctgcaa cgttgcccac ccggccagca gcaccaaggt ggacaagaaa     720
attgtgccca gggattgtgg ttgtaagcct tgcatatgta cagtcccaga agtatcatct     780
gtcttcatct tccccccaaa gcccaaggat gtgctcacca ttactctgac tcctaaggtc     840
acgtgtgttg tggtagacat cagcaaggat gatcccgagg tccagttcag ctggtttgta     900
gatgatgtgg aggtgcacac agctcagacg caaccccggg aggagcagtt caacagcact     960
ttccgctcag tcagtgaact tcccatcatg caccaggact ggctcaatgg caaggagttc    1020
aaatgcaggg tcaacagtgc agctttccct gcccccatcg agaaaccat ctccaaaacc    1080
aaaggcagac cgaaggctcc acaggtgtac accattccac ctcccaagga gcagatggcc    1140
aaggataaag tcagtctgac ctgcatgata acagacttct cccctgaaga cattactgtg    1200
gagtggcagt ggaatgggca gccagcggag aactacaaga cactcagcc catcatggac    1260
acagatggct cttacttcgt ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatga                                        1407
```

<210> SEQ ID NO 22
<211> LENGTH: 468
<212> TYPE: PRT
<213> ORGANISM: Artificial Sequence
<220> FEATURE:
<223> OTHER INFORMATION: mAb17 heavy chain

<400> SEQUENCE: 22

Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Pro Met His Trp Leu Lys Gln Ala Pro Gly

```
              50                  55                  60
Lys Gly Leu Lys Trp Met Gly Trp Ile Asn Thr Tyr Ser Gly Val Pro
 65                  70                  75                  80

Thr Tyr Ala Asp Asp Phe Lys Gly Arg Phe Ala Phe Ser Leu Glu Thr
                     85                  90                  95

Ser Ala Ser Thr Ala Tyr Leu Gln Ile Asn Asn Leu Lys Asn Glu Asp
                100                 105                 110

Met Ala Thr Tyr Phe Cys Thr Lys Ser Arg Ile Thr Thr Met Gly Gly
                115                 120                 125

Tyr Ala Met Asp Cys Trp Gly Gln Gly Thr Ser Val Thr Val Ser Ser
130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
                180                 185                 190

Gly Val His Thr Phe Pro Ala Val Leu Gln Ser Asp Leu Tyr Thr Leu
                195                 200                 205

Ser Ser Ser Val Thr Val Pro Ser Ser Thr Trp Pro Ser Glu Thr Val
210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
                260                 265                 270

Thr Ile Thr Leu Thr Pro Lys Val Thr Cys Val Val Val Asp Ile Ser
                275                 280                 285

Lys Asp Asp Pro Glu Val Gln Phe Ser Trp Phe Val Asp Asp Val Glu
290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
                340                 345                 350

Ile Glu Lys Thr Ile Ser Lys Thr Lys Gly Arg Pro Lys Ala Pro Gln
                355                 360                 365

Val Tyr Thr Ile Pro Pro Pro Lys Glu Gln Met Ala Lys Asp Lys Val
                370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
                420                 425                 430

Val Gln Lys Ser Asn Trp Glu Ala Gly Asn Thr Phe Thr Cys Ser Val
                435                 440                 445

Leu His Glu Gly Leu His Asn His Thr Glu Lys Ser Leu Ser His
                450                 455                 460

Ser Pro Gly Lys
465
```

<210> SEQ ID NO 23
<211> LENGTH: 7
<212> TYPE: PRT
<213> ORGANISM: Artificial Sequence
<220> FEATURE:
<223> OTHER INFORMATION: mAb17 heavy chain CDR1

<400> SEQUENCE: 23

Gly Tyr Thr Phe Thr Asn Tyr
1               5

<210> SEQ ID NO 24
<211> LENGTH: 6
<212> TYPE: PRT
<213> ORGANISM: Artificial Sequence
<220> FEATURE:
<223> OTHER INFORMATION: mAb17 heavy chain CDR2

<400> SEQUENCE: 24

Asn Thr Tyr Ser Gly Val
1               5

<210> SEQ ID NO 25
<211> LENGTH: 13
<212> TYPE: PRT
<213> ORGANISM: Artificial Sequence
<220> FEATURE:
<223> OTHER INFORMATION: mAb17 heavy chain CDR3

<400> SEQUENCE: 25

Ser Arg Ile Thr Thr Met Gly Gly Tyr Ala Met Asp Cys
1               5                   10

<210> SEQ ID NO 26
<211> LENGTH: 726
<212> TYPE: DNA
<213> ORGANISM: Artificial Sequence
<220> FEATURE:
<223> OTHER INFORMATION: mAb17 light chain

<400> SEQUENCE: 26

```
atggacatga gggtgcccgc tcagctcctg gggctcctgc tgctgtggct gagaggtgcg     60
cgctgtgaag ttgtgatgac ccaaactcca ctctccctgc ctgtcagtct tggagatcaa    120
gcctccatct cttgcagatc tagtcagagc cttctacaca gtaatggaaa cacctattta    180
cattggtacc tgcagaggcc aggccagtct ccaaacctcc tgatctccaa agtttccaac    240 cgatttctg gggtcccaga caggttcagt ggcagtggat cagggacaga tttcacactc     300
aagatcagca gagtggaggc tgaggatctg gagttttatt ctgctctcca aaatacacat    360
gttccgtgga cgttcggtgg aggcaccaag ctggaaatca acgtgcaga tgctgcgcca     420 actgtatcca tcttcccacc atctagcgag cagttaacat ctggaggtgc ctcagtcgtg    480
tgcttcttga caacttcta ccccaaagac atcaatgtca agtggaagat tgatggcagt     540
gaacgacaaa atggcgtcct gaacagttgg actgatcagg acagcaaaga cagcacctac    600
agcatgagca gcaccctcac gttgaccaag gacgagtatg aacgacataa cagctatacc    660
tgtgaggcca ctcacaagac atcaacttca cccattgtca agagcttcaa caggaatgag    720
tgttag                                                               726
```

<210> SEQ ID NO 27
<211> LENGTH: 241

```
<212> TYPE: PRT
<213> ORGANISM: Artificial Sequence
<220> FEATURE:
<223> OTHER INFORMATION: mAb17 light chain

<400> SEQUENCE: 27

Met Asp Met Arg Val Pro Ala Gln Leu Gly Leu Leu Leu Leu Trp
1               5                   10                  15

Leu Arg Gly Ala Arg Cys Glu Val Val Met Thr Gln Thr Pro Leu Ser
                20                  25                  30

Leu Pro Val Ser Leu Gly Asp Gln Ala Ser Ile Ser Cys Arg Ser Ser
            35                  40                  45

Gln Ser Leu Leu His Ser Asn Gly Asn Thr Tyr Leu His Trp Tyr Leu
    50                  55                  60

Gln Arg Pro Gly Gln Ser Pro Asn Leu Leu Ile Ser Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Phe Cys Ser Gln Asn Thr His Val Pro Trp Thr Phe Gly Gly Gly
        115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225                 230                 235                 240

Cys

<210> SEQ ID NO 28
<211> LENGTH: 16
<212> TYPE: PRT
<213> ORGANISM: Artificial Sequence
<220> FEATURE:
<223> OTHER INFORMATION: mAb17 light chain CDR1

<400> SEQUENCE: 28

Arg Ser Ser Gln Ser Leu Leu His Ser Asn Gly Asn Thr Tyr Leu His
1               5                   10                  15

<210> SEQ ID NO 29
<211> LENGTH: 7
<212> TYPE: PRT
<213> ORGANISM: Artificial Sequence
<220> FEATURE:
<223> OTHER INFORMATION: mAb17 light chain CDR2

<400> SEQUENCE: 29

Lys Val Ser Asn Arg Phe Ser
1               5
```

<210> SEQ ID NO 30
<211> LENGTH: 9
<212> TYPE: PRT
<213> ORGANISM: Artificial Sequence
<220> FEATURE:
<223> OTHER INFORMATION: mAb17 light chain CDR3

<400> SEQUENCE: 30

Ser Gln Asn Thr His Val Pro Trp Thr
1               5

<210> SEQ ID NO 31
<211> LENGTH: 1407
<212> TYPE: DNA
<213> ORGANISM: Artificial Sequence
<220> FEATURE:
<223> OTHER INFORMATION: mAb20 heavy chain

<400> SEQUENCE: 31

| | | | | | |
|---|---|---|---|---|---|
| atggacatga | gggtgcccgc | tcagctcctg | gggctcctgc | tgctgtggct | gagaggtgcg     60 |
| cgctgtcaga | tccagttggt | gcagtctgga | cctgagctga | agaagcctgg | agagacagtc    120 |
| aagatctcct | gcaaggcttc | tgggtatatc | ttcacaaact | atccaatgca | ctgggtgaag    180 |
| caggctccag | gaaagggttt | aaagtggatg | gctggataa | acacctactc | tggagtgcca    240 |
| acacatgcag | atgacttcaa | gggacggttt | gccttctctt | tggaaacctc | tgccaacagt    300 |
| gcattttgc | agatcaacaa | cctcaaaaat | gaggacacgg | ctacatattt | ctgtacaaga    360 |
| tcgcgcatta | ctccgacggg | gggctatgct | atggactact | ggggtcaagg | aacctcagtc    420 |
| accgtctcta | gtgccaaaac | gacacccca | tctgtctacc | cactggcccc | tggatctgct    480 |
| gcccaaacta | actccatggt | gaccctggga | tgcctggtca | agggctattt | ccctgagcca    540 |
| gtgacagtga | cctggaactc | tggatccctg | tccagcggtg | tgcacacctt | cccagctgtc    600 |
| ctgcagtctg | acctctacac | tctgagcagc | tcagtgactg | tcccctccag | cacctggccc    660 |
| agcgagaccg | tcacctgcaa | cgttgcccac | ccggccagca | gcaccaaggt | ggacaagaaa    720 |
| attgtgccca | gggattgtgg | ttgtaagcct | tgcatatgta | cagtcccaga | agtatcatct    780 |
| gtcttcatct | tccccccaaa | gcccaaggat | gtgctcacca | ttactctgac | tcctaaggtc    840 |
| acgtgtgttg | tggtagacat | cagcaaggat | gatcccgagg | tccagttcag | ctggtttgta    900 |
| gatgatgtgg | aggtgcacac | agctcagacg | caaccccggg | aggagcagtt | caacagcact    960 |
| ttccgctcag | tcagtgaact | tcccatcatg | caccaggact | ggctcaatgg | caaggagttc   1020 |
| aaatgcaggg | tcaacagtgc | agctttccct | gcccccatcg | agaaaaccat | ctccaaaacc   1080 |
| aaaggcagac | cgaaggctcc | acaggtgtac | accattccac | ctcccaagga | gcagatggcc   1140 |
| aaggataaag | tcagtctgac | ctgcatgata | acagacttct | tccctgaaga | cattactgtg   1200 |
| gagtggcagt | ggaatgggca | gccagcggag | aactacaaga | acactcagcc | catcatggac   1260 |
| acagatggct | cttacttcgt | ctacagcaag | ctcaatgtgc | agaagagcaa | ctgggaggca   1320 |
| ggaaatactt | tcacctgctc | tgtgttacat | gagggcctgc | acaaccacca | tactgagaag   1380 |
| agcctctccc | actctcctgg | taaatga    |            |            |           1407 |

<210> SEQ ID NO 32
<211> LENGTH: 468
<212> TYPE: PRT
<213> ORGANISM: Artificial Sequence
<220> FEATURE:
<223> OTHER INFORMATION: mAb20 heavy chain

<400> SEQUENCE: 32

```
Met Asp Met Arg Val Pro Ala Gln Leu Leu Gly Leu Leu Leu Trp
1               5                   10                  15

Leu Arg Gly Ala Arg Cys Gln Ile Gln Leu Val Gln Ser Gly Pro Glu
                20                  25                  30

Leu Lys Lys Pro Gly Glu Thr Val Lys Ile Ser Cys Lys Ala Ser Gly
            35                  40                  45

Tyr Ile Phe Thr Asn Tyr Pro Met His Trp Val Lys Gln Ala Pro Gly
        50                  55                  60

Lys Gly Leu Lys Trp Met Gly Trp Ile Asn Thr Tyr Ser Gly Val Pro
65                  70                  75                  80

Thr His Ala Asp Asp Phe Lys Gly Arg Phe Ala Phe Ser Leu Glu Thr
                85                  90                  95

Ser Ala Asn Ser Ala Phe Leu Gln Ile Asn Asn Leu Lys Asn Glu Asp
                100                 105                 110

Thr Ala Thr Tyr Phe Cys Thr Arg Ser Arg Ile Thr Pro Thr Gly Gly
            115                 120                 125

Tyr Ala Met Asp Tyr Trp Gly Gln Gly Thr Ser Val Thr Val Ser Ser
        130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
            290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
            340                 345                 350

Ile Glu Lys Thr Ile Ser Lys Thr Lys Gly Arg Pro Lys Ala Pro Gln
        355                 360                 365

Val Tyr Thr Ile Pro Pro Pro Lys Glu Gln Met Ala Lys Asp Lys Val
    370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
```

405                 410                 415
Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His His Thr Glu Lys Ser Leu Ser His
    450                 455                 460

Ser Pro Gly Lys
465

<210> SEQ ID NO 33
<211> LENGTH: 7
<212> TYPE: PRT
<213> ORGANISM: Artificial Sequence
<220> FEATURE:
<223> OTHER INFORMATION: mAb20 heavy chain CDR1

<400> SEQUENCE: 33

Gly Tyr Ile Phe Thr Asn Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: mAb20 heavy chain CDR2

<400> SEQUENCE: 34

Asn Thr Tyr Ser Gly Val
1               5

<210> SEQ ID NO 35
<211> LENGTH: 13
<212> TYPE: PRT
<213> ORGANISM: Artificial Sequence
<220> FEATURE:
<223> OTHER INFORMATION: mAb20 heavy chain CDR3

<400> SEQUENCE: 35

Ser Arg Ile Thr Pro Thr Gly Gly Tyr Ala Met Asp Tyr
1               5                   10

<210> SEQ ID NO 36
<211> LENGTH: 726
<212> TYPE: DNA
<213> ORGANISM: Artificial Sequence
<220> FEATURE:
<223> OTHER INFORMATION: mAb20 light chain

<400> SEQUENCE: 36
atggacatga gggtgcccgc tcagctcctg ggctcctgc tgctgtggct gagaggtgcg      60
cgctgtgatg ttgtgatgac ccaaactcca ctctccctgc ctgtcagtct tggagatcaa    120
gcctccatct cttgcagatc tagtcagagc cttgtacaca gtaatggaaa cacctattta    180
cattggtacc tgcagaagcc aggccagtct ccaaacctcc tgatctccaa agtttccaac    240
cgattttctg ggtcccaga aaggttcagt ggcagtggat cagggacaga tttcacactc    300
aagatcagca gagtggaggc tgaggatctg ggagtttatt tctgctctca aaatacacat    360
gttccgtgga cgttcggtgg aggcaccaag ctggaaatca acgtgcaga tgctgcgcca    420 actgtatcca tcttcccacc atctagcgag cagttaacat ctggaggtgc ctcagtcgtg    480

```
tgcttcttga caacttcta ccccaaagac atcaatgtca agtggaagat tgatggcagt    540
gaacgacaaa atggcgtcct gaacagttgg actgatcagg acagcaaaga cagcaccctac   600 agcatgagca gcaccctcac gttgaccaag gacgagtatg aacgacataa cagctatacc   660
tgtgaggcca ctcacaagac atcaacttca cccattgtca agagcttcaa caggaatgag   720
tgttag                                                              726
```

```
<210> SEQ ID NO 37
<211> LENGTH: 241
<212> TYPE: PRT
<213> ORGANISM: Artificial Sequence
<220> FEATURE:
<223> OTHER INFORMATION: mAb20 light chain

<400> SEQUENCE: 37
```

Met Asp Met Arg Val Pro Ala Gln Leu Leu Gly Leu Leu Leu Leu Trp
1               5                   10                  15

Leu Arg Gly Ala Arg Cys Asp Val Val Met Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Val His Ser Asn Gly Asn Thr Tyr Leu His Trp Tyr Leu
    50                  55                  60

Gln Lys Pro Gly Gln Ser Pro Asn Leu Leu Ile Ser Lys Val Ser Asn
65                  70                  75                  80

Arg Phe Ser Gly Val Pro Glu Arg Phe Ser Gly Ser Gly Ser Gly Thr
                85                  90                  95

Asp Phe Thr Leu Lys Ile Ser Arg Val Glu Ala Glu Asp Leu Gly Val
            100                 105                 110

Tyr Phe Cys Ser Gln Asn Thr His Val Pro Trp Thr Phe Gly Gly Gly
        115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225                 230                 235                 240

Cys

```
<210> SEQ ID NO 38
<211> LENGTH: 16
<212> TYPE: PRT
<213> ORGANISM: Artificial Sequence
<220> FEATURE:
<223> OTHER INFORMATION: mAb20 light chain CDR1

<400> SEQUENCE: 38
```

Arg Ser Ser Gln Ser Leu Val His Ser Asn Gly Asn Thr Tyr Leu His
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: mAb20 light chain CDR2

<400> SEQUENCE: 39

Lys Val Ser Asn Arg Phe Ser
1               5

<210> SEQ ID NO 40
<211> LENGTH: 9
<212> TYPE: PRT
<213> ORGANISM: Artificial Sequence
<220> FEATURE:
<223> OTHER INFORMATION: mAb40 light chain CDR3

<400> SEQUENCE: 40

Ser Gln Asn Thr His Val Pro Trp Thr
1               5

<210> SEQ ID NO 41
<211> LENGTH: 1407
<212> TYPE: DNA
<213> ORGANISM: Artificial Sequence
<220> FEATURE:
<223> OTHER INFORMATION: mAb28 heavy chain

<400> SEQUENCE: 41

| | | | | | |
|---|---|---|---|---|---|
| atggacatga | gggtgcccgc | tcagctcctg | gggctcctgc | tgctgtggct | gagaggtgcg | 60 |
| cgctgtcaga | tccagttggt | gcagtctgga | cctgagctga | agaagcctgg | agagacagtc | 120 |
| aagatctcct | gcaaggcttc | tgggtatacc | ttcacaaact | atccaatgca | ctgggtaaag | 180 |
| caggctccag | gaaaggattt | aaagtggatg | gctggataa | acacctactc | tggaatgtca | 240 |
| acatatgcag | atgacttcaa | gggacggttt | gccttctctt | tggaaacctc | tgccagcact | 300 |
| gcgtatttgc | agatcaacaa | cctcaaaaat | gaggacatgg | ctacatattt | ctgtgcaaga | 360 |
| tcgcgcatta | aacgatggg | gggctatgct | atggactact | ggggtcaagg | agcctcagtc | 420 |
| accgtctcta | gtgccaaaac | gacaccccca | tctgtctacc | cactggcccc | tggatctgct | 480 |
| gcccaaacta | actccatggt | gaccctggga | tgcctggtca | agggctattt | ccctgagcca | 540 |
| gtgacagtga | cctggaactc | tggatccctg | tccagcggtg | tgcacacctt | cccagctgtc | 600 |
| ctgcagtctg | acctctacac | tctgagcagc | tcagtgactg | tcccctccag | cacctggccc | 660 |
| agcgagaccg | tcacctgcaa | cgttgcccac | ccggccagca | gcaccaaggt | ggacaagaaa | 720 |
| attgtgccca | gggattgtgg | ttgtaagcct | tgcatatgta | cagtcccaga | agtatcatct | 780 |
| gtcttcatct | tccccccaaa | gcccaaggat | gtgctcacca | ttactctgac | tcctaaggtc | 840 |
| acgtgtgttg | tggtagacat | cagcaaggat | gatcccgagg | tccagttcag | ctggtttgta | 900 |
| gatgatgtgg | aggtgcacac | agctcagacg | caaccccggg | aggagcagtt | caacagcact | 960 |
| ttccgctcag | tcagtgaact | tcccatcatg | caccaggact | ggctcaatgg | caaggagttc | 1020 |
| aaatgcaggg | tcaacagtgc | agctttccct | gcccccatcg | agaaaaccat | ctccaaaacc | 1080 |
| aaaggcagac | cgaaggctcc | acaggtgtac | accattccac | ctcccaagga | gcagatggcc | 1140 |
| aaggataaag | tcagtctgac | ctgcatgata | acagacttct | tccctgaaga | cattactgtg | 1200 |
| gagtggcagt | ggaatgggca | gccagcggag | aactacaaga | cactcagcc | catcatggac | 1260 |

```
acagatggct cttacttcgt ctacagcaag ctcaatgtgc agaagagcaa ctgggaggca    1320
ggaaatactt tcacctgctc tgtgttacat gagggcctgc acaaccacca tactgagaag    1380
agcctctccc actctcctgg taaatga                                        1407
```

<210> SEQ ID NO 42
<211> LENGTH: 468
<212> TYPE: PRT
<213> ORGANISM: Artificial Sequence
<220> FEATURE:
<223> OTHER INFORMATION: mAb28 heavy chain

<400> SEQUENCE: 42

```
Met Asp Met Arg Val Pro Ala Gln Leu Leu Gly Leu Leu Leu Leu Trp
1               5                   10                  15

Leu Arg Gly Ala Arg Cys Gln Ile Gln Leu Val Gln Ser Gly Pro Glu
            20                  25                  30

Leu Lys Lys Pro Gly Glu Thr Val Lys Ile Ser Cys Lys Ala Ser Gly
        35                  40                  45

Tyr Thr Phe Thr Asn Tyr Pro Met His Trp Val Lys Gln Ala Pro Gly
    50                  55                  60

Lys Asp Leu Lys Trp Met Gly Trp Ile Asn Thr Tyr Ser Gly Met Ser
65                  70                  75                  80

Thr Tyr Ala Asp Asp Phe Lys Gly Arg Phe Ala Phe Ser Leu Glu Thr
                85                  90                  95

Ser Ala Ser Thr Ala Tyr Leu Gln Ile Asn Asn Leu Lys Asn Glu Asp
            100                 105                 110

Met Ala Thr Tyr Phe Cys Ala Arg Ser Arg Ile Thr Thr Met Gly Gly
        115                 120                 125

Tyr Ala Met Asp Tyr Trp Gly Gln Gly Ala Ser Val Thr Val Ser Ser
    130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
            180                 185                 190

Gly Val His Thr Phe Pro Ala Val Leu Gln Ser Asp Leu Tyr Thr Leu
        195                 200                 205

Ser Ser Ser Val Thr Val Pro Ser Ser Thr Trp Pro Ser Glu Thr Val
    210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
            260                 265                 270

Thr Ile Thr Leu Thr Pro Lys Val Thr Cys Val Val Val Asp Ile Ser
        275                 280                 285

Lys Asp Asp Pro Glu Val Gln Phe Ser Trp Phe Val Asp Asp Val Glu
    290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335
```

```
Gly Lys Glu Phe Lys Cys Arg Val Asn Ser Ala Ala Phe Pro Ala Pro
                340                 345                 350

Ile Glu Lys Thr Ile Ser Lys Thr Lys Gly Arg Pro Lys Ala Pro Gln
            355                 360                 365

Val Tyr Thr Ile Pro Pro Lys Glu Gln Met Ala Lys Asp Lys Val
        370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asp Thr Asp Gly Ser Tyr Phe Val Tyr Ser Lys Leu Asn
            420                 425                 430

Val Gln Lys Ser Asn Trp Glu Ala Gly Asn Thr Phe Thr Cys Ser Val
        435                 440                 445

Leu His Glu Gly Leu His Asn His Thr Glu Lys Ser Leu Ser His
                450                 455                 460

Ser Pro Gly Lys
465

<210> SEQ ID NO 43
<211> LENGTH: 7
<212> TYPE: PRT
<213> ORGANISM: Artificial Sequence
<220> FEATURE:
<223> OTHER INFORMATION: mAb28 heavy chain CDR1

<400> SEQUENCE: 43

Gly Tyr Thr Phe Thr Asn Tyr
1               5

<210> SEQ ID NO 44
<211> LENGTH: 6
<212> TYPE: PRT
<213> ORGANISM: Artificial Sequence
<220> FEATURE:
<223> OTHER INFORMATION: mAb28 heavy chain CDR2

<400> SEQUENCE: 44

Asn Thr Tyr Ser Gly Met
1               5

<210> SEQ ID NO 45
<211> LENGTH: 13
<212> TYPE: PRT
<213> ORGANISM: Artificial Sequence
<220> FEATURE:
<223> OTHER INFORMATION: mAb28 heavy chain CDR3

<400> SEQUENCE: 45

Ser Arg Ile Thr Thr Met Gly Gly Tyr Ala Met Asp Tyr
1               5                   10

<210> SEQ ID NO 46
<211> LENGTH: 726
<212> TYPE: DNA
<213> ORGANISM: Artificial Sequence
<220> FEATURE:
<223> OTHER INFORMATION: mAb28 light chain

<400> SEQUENCE: 46
atggacatga gggtgcccgc tcagctcctg gggctcctgc tgctgtggct gagaggtgcg      60
cgctgtgaag ttgtgatgac ccaaactcca ctctcccctgc ctgtcagtct tggagatcaa     120
```

```
gcctccatct cttgcagatc tagtcagagc cttgtacaca gtaatggaaa cacctattta    180
cattggtacc tgcagaagcc aggccagtct ccaaagctcc tgatctccaa agtttccaac    240
cgattttctg gggtcccaga caggttcagt ggcagtggat cagggacaga tttcacactc    300
aagatcatca gagtggaggc tgaggatctg ggagtttatt tctgctctca aaatacacat    360
gttccgtgga cgttcggtgg aggcaccaag ctggaaatca aacgtgcaga tgctgcgcca    420
actgtatcca tcttcccacc atctagcgag cagttaacat ctggaggtgc ctcagtcgtg    480
tgcttcttga caacttcta ccccaaagac atcaatgtca gtggaagat tgatggcagt    540 gaacgacaaa atggcgtcct gaacagttgg actgatcagg acagcaaaga cagcacctac    600
agcatgagca gcaccctcac gttgaccaag gacgagtatg aacgacataa cagctatacc    660
tgtgaggcca ctcacaagac atcaacttca cccattgtca agagcttcaa caggaatgag    720
tgttag                                                              726
```

<210> SEQ ID NO 47
<211> LENGTH: 241
<212> TYPE: PRT
<213> ORGANISM: Artificial Sequence
<220> FEATURE:
<223> OTHER INFORMATION: mAb28 light chain

<400> SEQUENCE: 47

```
Met Asp Met Arg Val Pro Ala Gln Leu Leu Gly Leu Leu Leu Leu Trp
1               5                   10                  15

Leu Arg Gly Ala Arg Cys Glu Val Val Met Thr Gln Thr Pro Leu Ser
            20                  25                  30

Leu Pro Val Ser Leu Gly Asp Gln Ala Ser Ile Ser Cys Arg Ser Ser
        35                  40                  45

Gln Ser Leu Val His Ser Asn Gly Asn Thr Tyr Leu His Trp Tyr Leu
    50                  55                  60

Gln Lys Pro Gly Gln Ser Pro Lys Leu Leu Ile Ser Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ile Arg Val Glu Ala Glu Asp Leu Gly Val
            100                 105                 110

Tyr Phe Cys Ser Gln Asn Thr His Val Pro Trp Thr Phe Gly Gly Gly
        115                 120                 125

Thr Lys Leu Glu Ile Lys Arg Ala Asp Ala Ala Pro Thr Val Ser Ile
    130                 135                 140

Phe Pro Pro Ser Ser Glu Gln Leu Thr Ser Gly Gly Ala Ser Val Val
145                 150                 155                 160

Cys Phe Leu Asn Asn Phe Tyr Pro Lys Asp Ile Asn Val Lys Trp Lys
                165                 170                 175

Ile Asp Gly Ser Glu Arg Gln Asn Gly Val Leu Asn Ser Trp Thr Asp
            180                 185                 190

Gln Asp Ser Lys Asp Ser Thr Tyr Ser Met Ser Ser Thr Leu Thr Leu
        195                 200                 205

Thr Lys Asp Glu Tyr Glu Arg His Asn Ser Tyr Thr Cys Glu Ala Thr
    210                 215                 220

His Lys Thr Ser Thr Ser Pro Ile Val Lys Ser Phe Asn Arg Asn Glu
225                 230                 235                 240

Cys
```

<210> SEQ ID NO 48
<211> LENGTH: 16
<212> TYPE: PRT
<213> ORGANISM: Artificial Sequence
<220> FEATURE:
<223> OTHER INFORMATION: mAb28 light chain CDR1

<400> SEQUENCE: 48

Arg Ser Ser Gln Ser Leu Val His Ser Asn Gly Asn Thr Tyr Leu His
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: mAb28 light chain CDR2

<400> SEQUENCE: 49

Lys Val Ser Asn Arg Phe Ser
1               5

<210> SEQ ID NO 50
<211> LENGTH: 9
<212> TYPE: PRT
<213> ORGANISM: Artificial Sequence
<220> FEATURE:
<223> OTHER INFORMATION: mAb28 light chain CDR3

<400> SEQUENCE: 50

Ser Gln Asn Thr His Val Pro Trp Thr
1               5

<210> SEQ ID NO 51
<211> LENGTH: 1389
<212> TYPE: DNA
<213> ORGANISM: Artificial Sequence
<220> FEATURE:
<223> OTHER INFORMATION: mAb39 heavy chain

<400> SEQUENCE: 51

```
atgggatgga gctgtatcat gttcttttg gtagcaacag ctacagatgt ccactcccag      60
gtccaactgc agcagcctgg ggctgaactg gtgaagcctg gggcttcagt gaagctgtcc    120
tgcaaggctt ctggctactc cttcaccacc tactggatgc actgggtgaa gcagaggcct    180
ggacaaggcc tagagtgggt tggagatatt aatcctagga cggtcgtac taactacaat    240
gagaagtcca agagcaaggc cacactgact gtagacatat catccagcac agtatacatg    300
caagtcagca gcctgacatc tgaggactct gcggtctatt actgtgcaat atggtcgggt    360
gctatggact actggggtcc aggaacctca gtcaccgtct cctcagccaa acaacagcc    420
ccatcggtct atccactggc ccctgtgtgt ggagatacaa ctggctcctc ggtgactcta    480
ggatgcctgg tcaagggtta tttccctgag ccagtgacct tgacctggaa ctctggatcc    540
ctgtccagtg atgtgcacac cttcccagct ctcctgcagt ctggcctcta caccctcagc    600
agctcagtga ctgtaaccac ctggcccagc cagaccatca cctgcaatgt ggcccacccg    660
gcaagcagca ccaaagtgga caagaaaatt gagcccagag gtccccaac acataaaccc    720
tgtcctccat gcccagctcc taacctcttg gtggaccat ccgtcttcat cttccctcca    780
aagatcaagg atgtactcat gatctccctg agcccatgg tcacgtgtgt ggtggtggat    840
gtgagcgagg atgacccaga tgtccatgtc agctggttcg tgaacaacgt ggaagtacac    900
```

```
acagctcaga cacaaaccca tagagaggat tacaacagta ctatccgggt ggtcagtgcc    960
ctccccatcc agcaccagga ctggatgagt ggcaaggagt tcaaatgcaa ggtcaacaac   1020
aaagccctcc cagcgcccat cgagagaacc atctcaaaac ccaagggcc  agtaagagct   1080 ccacaggtat atgtcttgcc tccaccagaa gaagagatga ctaagaaaca ggtcactctg   1140
acctgcatga tcacagactt catgcctgaa gacatttacg tggagtggac caacaacggg   1200
caaacagagc taaactacaa gaacactgaa ccagtcctgg actctgatgg ttcttacttc   1260
atgtacagca agctgagagt ggaaaagaag aactgggtgg aaagaaatag ctactcctgt   1320
tcagtggtcc acgagggtct gcacaatcac cacacgacta agagcttctc ccggtctccg   1380
ggtaaatga                                                          1389
```

<210> SEQ ID NO 52
<211> LENGTH: 462
<212> TYPE: PRT
<213> ORGANISM: Artificial Sequence
<220> FEATURE:
<223> OTHER INFORMATION: mAb39 heavy chain

<400> SEQUENCE: 52

```
Met Gly Trp Ser Cys Ile Met Phe Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Ser Phe
        35                  40                  45

Thr Thr Tyr Trp Met His Trp Val Lys Gln Arg Pro Gly Gln Gly Leu
    50                  55                  60

Glu Trp Val Gly Asp Ile Asn Pro Arg Asn Gly Arg Thr Asn Tyr Asn
65                  70                  75                  80

Glu Lys Ser Lys Ser Lys Ala Thr Leu Thr Val Asp Ile Ser Ser Ser
                85                  90                  95

Thr Val Tyr Met Gln Val Ser Ser Leu Thr Ser Glu Asp Ser Ala Val
            100                 105                 110

Tyr Tyr Cys Ala Ile Trp Ser Gly Ala Met Asp Tyr Trp Gly Pro Gly
        115                 120                 125

Thr Ser Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Asp Val His Thr Phe Pro Ala Leu Leu
            180                 185                 190

Gln Ser Gly Leu Tyr Thr Leu Ser Ser Val Thr Val Thr Thr Trp
        195                 200                 205

Pro Ser Gln Thr Ile Thr Cys Asn Val Ala His Pro Ala Ser Ser Thr
    210                 215                 220

Lys Val Asp Lys Lys Ile Glu Pro Arg Gly Ser Pro Thr His Lys Pro
225                 230                 235                 240

Cys Pro Pro Cys Pro Ala Pro Asn Leu Leu Gly Gly Pro Ser Val Phe
                245                 250                 255

Ile Phe Pro Pro Lys Ile Lys Asp Val Leu Met Ile Ser Leu Ser Pro
            260                 265                 270
```

```
Met Val Thr Cys Val Val Asp Val Ser Glu Asp Pro Asp Val
        275                 280                 285

His Val Ser Trp Phe Val Asn Asn Val Glu Val His Thr Ala Gln Thr
290                 295                 300

Gln Thr His Arg Glu Asp Tyr Asn Ser Thr Ile Arg Val Val Ser Ala
305                 310                 315                 320

Leu Pro Ile Gln His Gln Asp Trp Met Ser Gly Lys Glu Phe Lys Cys
                325                 330                 335

Lys Val Asn Asn Lys Ala Leu Pro Ala Pro Ile Glu Arg Thr Ile Ser
                340                 345                 350

Lys Pro Lys Gly Pro Val Arg Ala Pro Gln Val Tyr Val Leu Pro Pro
            355                 360                 365

Pro Glu Glu Glu Met Thr Lys Lys Gln Val Thr Leu Thr Cys Met Ile
        370                 375                 380

Thr Asp Phe Met Pro Glu Asp Ile Tyr Val Glu Trp Thr Asn Asn Gly
385                 390                 395                 400

Gln Thr Glu Leu Asn Tyr Lys Asn Thr Glu Pro Val Leu Asp Ser Asp
                405                 410                 415

Gly Ser Tyr Phe Met Tyr Ser Lys Leu Arg Val Glu Lys Lys Asn Trp
                420                 425                 430

Val Glu Arg Asn Ser Tyr Ser Cys Ser Val Val His Glu Gly Leu His
            435                 440                 445

Asn His His Thr Thr Lys Ser Phe Ser Arg Ser Pro Gly Lys
            450                 455                 460

<210> SEQ ID NO 53
<211> LENGTH: 7
<212> TYPE: PRT
<213> ORGANISM: Artificial Sequence
<220> FEATURE:
<223> OTHER INFORMATION: mAb39 heavy chain CDR1

<400> SEQUENCE: 53

Gly Tyr Ser Phe Thr Thr Tyr
1               5

<210> SEQ ID NO 54
<211> LENGTH: 6
<212> TYPE: PRT
<213> ORGANISM: Artificial Sequence
<220> FEATURE:
<223> OTHER INFORMATION: mAb39 heavy chain CDR2

<400> SEQUENCE: 54

Asn Pro Arg Asn Gly Arg
1               5

<210> SEQ ID NO 55
<211> LENGTH: 7
<212> TYPE: PRT
<213> ORGANISM: Artificial Sequence
<220> FEATURE:
<223> OTHER INFORMATION: mAb39 heavy chain CDR3

<400> SEQUENCE: 55

Trp Ser Gly Ala Met Asp Tyr
1               5

<210> SEQ ID NO 56
<211> LENGTH: 717
```

```
<212> TYPE: DNA
<213> ORGANISM: Artificial Sequence
<220> FEATURE:
<223> OTHER INFORMATION: mAb39 light chain

<400> SEQUENCE: 56
atgaagttgc ctgttaggct gttggtgctg atgttctgga ttcctgcttc cagcagtgat      60
gttgtgatga cccaaactcc actctccctg cctgtcagtc ttggagatca accctccatc     120
tcttgcaaat ctagtcagag ccttgtacac aataatggaa acacctattt acattggtac     180
ctgcagaagc caggccagtc tccaaagctc ctgatctaca agtttccaa ccgattttct      240 ggggtcccag acaggttcag tggcagtgga tcagggacag atttcacact caagatcagc     300
agagtggagg ctgaggatct gggagtttat ttctgctctc aaactacaca tgttcctccg     360
acgttcggtg aggcaccaa gctggaaatc aaacgggctg atgctgcacc aactgtatcc      420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat gaacgacata cagctatac ctgtgaggcc      660 actcacaaga catcaacttc acccattgtc aagagcttca caggggaga gtgttga         717

<210> SEQ ID NO 57
<211> LENGTH: 238
<212> TYPE: PRT
<213> ORGANISM: Artificial Sequence
<220> FEATURE:
<223> OTHER INFORMATION: mAb39 light chain

<400> SEQUENCE: 57

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Pro Ser Ile Ser Cys Lys Ser Ser Gln Ser Leu
        35                  40                  45

Val His Asn Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Thr Thr His Val Pro Pro Thr Phe Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205
```

```
Glu Tyr Glu Arg His Asn Ser Tyr Thr Cys Glu Ala Thr His Lys Thr
    210                 215                 220

Ser Thr Ser Pro Ile Val Lys Ser Phe Asn Arg Gly Glu Cys
225                 230                 235
```

```
<210> SEQ ID NO 58
<211> LENGTH: 16
<212> TYPE: PRT
<213> ORGANISM: Artificial Sequence
<220> FEATURE:
<223> OTHER INFORMATION: mAb39 light chain CDR1

<400> SEQUENCE: 58

Lys Ser Ser Gln Ser Leu Val His Asn Asn Gly Asn Thr Tyr Leu His
1               5                   10                  15

<210> SEQ ID NO 59
<211> LENGTH: 7
<212> TYPE: PRT
<213> ORGANISM: Artificial Sequence
<220> FEATURE:
<223> OTHER INFORMATION: mAb39 light chain CDR2

<400> SEQUENCE: 59

Lys Val Ser Asn Arg Phe Ser
1               5

<210> SEQ ID NO 60
<211> LENGTH: 9
<212> TYPE: PRT
<213> ORGANISM: Artificial Sequence
<220> FEATURE:
<223> OTHER INFORMATION: mAb39 light chain CDR3

<400> SEQUENCE: 60

Ser Gln Thr Thr His Val Pro Pro Thr
1               5

<210> SEQ ID NO 61
<211> LENGTH: 1389
<212> TYPE: DNA
<213> ORGANISM: Artificial Sequence
<220> FEATURE:
<223> OTHER INFORMATION: mAb39 heavy chain v2 (t1375a-->S459T)

<400> SEQUENCE: 61
atgggatgga gctgtatcat gttctttttg gtagcaacag ctacagatgt ccactcccag      60
gtccaactgc agcagcctgg ggctgaactg gtgaagcctg ggcttcagt gaagctgtcc      120 tgcaaggctt ctggctactc cttcaccacc tactggatgc actgggtgaa gcagaggcct    180
ggacaaggcc tagagtgggt tggagatatt aatcctagga acggtcgtac taactacaat    240
gagaagtcca gagcaaggc cacactgact gtagacatat catccagcac agtatacatg     300
caagtcagca gcctgacatc tgaggactct gcggtctatt actgtgcaat atggtcgggt    360
gctatggact actggggtcc aggaaccctca gtcaccgtct cctcagccaa acaacagcc    420 ccatcggtct atccactggc ccctgtgtgt ggagatacaa ctggctcctc ggtgactcta    480
ggatgcctgg tcaagggtta tttccctgag ccagtgacct tgacctggaa ctctggatcc    540
ctgtccagtg atgtgcacac cttcccagct ctcctgcagt ctggcctcta caccctcagc    600
agctcagtga ctgtaaccac ctggcccagc cagaccatca cctgcaatgt ggcccacccg    660
gcaagcagca ccaaagtgga caagaaaatt gagcccagag ggtccccaac acataaaccc    720
```

```
tgtcctccat gcccagctcc taacctcttg ggtggaccat ccgtcttcat cttccctcca    780
aagatcaagg atgtactcat gatctccctg agccccatgg tcacgtgtgt ggtggtggat    840
gtgagcgagg atgacccaga tgtccatgtc agctggttcg tgaacaacgt ggaagtacac    900
acagctcaga cacaaaccca tagagaggat tacaacagta ctatccgggt ggtcagtgcc    960
ctccccatcc agcaccagga ctggatgagt ggcaaggagt tcaaatgcaa ggtcaacaac   1020
aaagccctcc cagcgcccat cgagagaacc atctcaaaac ccaagggcc agtaagagct    1080 ccacaggtat atgtcttgcc tccaccagaa gaagagatga ctaagaaaca ggtcactctg   1140
acctgcatga tcacagactt catgcctgaa gacatttacg tggagtggac caacaacggg   1200
caaacagagc taaactacaa gaacactgaa ccagtcctgg actctgatgg ttcttacttc   1260
atgtacagca agctgagagt ggaaaagaag aactgggtgg aaagaaatag ctactcctgt   1320
tcagtggtcc acgagggtct gcacaatcac cacacgacta agagcttctc ccggactccg   1380
ggtaaatga                                                           1389
```

<210> SEQ ID NO 62
<211> LENGTH: 462
<212> TYPE: PRT
<213> ORGANISM: Artificial Sequence
<220> FEATURE:
<223> OTHER INFORMATION: mAb39 heavy chain (S459T)

<400> SEQUENCE: 62

```
Met Gly Trp Ser Cys Ile Met Phe Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Ser Phe
        35                  40                  45

Thr Thr Tyr Trp Met His Trp Val Lys Gln Arg Pro Gly Gln Gly Leu
    50                  55                  60

Glu Trp Val Gly Asp Ile Asn Pro Arg Asn Gly Arg Thr Asn Tyr Asn
65                  70                  75                  80

Glu Lys Ser Lys Ser Lys Ala Thr Leu Thr Val Asp Ile Ser Ser Ser
                85                  90                  95

Thr Val Tyr Met Gln Val Ser Ser Leu Thr Ser Glu Asp Ser Ala Val
            100                 105                 110

Tyr Tyr Cys Ala Ile Trp Ser Gly Ala Met Asp Tyr Trp Gly Pro Gly
        115                 120                 125

Thr Ser Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Asp Val His Thr Phe Pro Ala Leu Leu
            180                 185                 190

Gln Ser Gly Leu Tyr Thr Leu Ser Ser Val Thr Val Thr Thr Trp
        195                 200                 205

Pro Ser Gln Thr Ile Thr Cys Asn Val Ala His Pro Ala Ser Ser Thr
    210                 215                 220

Lys Val Asp Lys Lys Ile Glu Pro Arg Gly Ser Pro Thr His Lys Pro
225                 230                 235                 240
```

```
Cys Pro Pro Cys Pro Ala Pro Asn Leu Leu Gly Gly Pro Ser Val Phe
            245                 250                 255

Ile Phe Pro Pro Lys Ile Lys Asp Val Leu Met Ile Ser Leu Ser Pro
            260                 265                 270

Met Val Thr Cys Val Val Val Asp Val Ser Glu Asp Pro Asp Val
            275                 280                 285

His Val Ser Trp Phe Val Asn Asn Val Glu Val His Thr Ala Gln Thr
            290                 295                 300

Gln Thr His Arg Glu Asp Tyr Asn Ser Thr Ile Arg Val Val Ser Ala
305                 310                 315                 320

Leu Pro Ile Gln His Gln Asp Trp Met Ser Gly Lys Glu Phe Lys Cys
                325                 330                 335

Lys Val Asn Asn Lys Ala Leu Pro Ala Pro Ile Glu Arg Thr Ile Ser
            340                 345                 350

Lys Pro Lys Gly Pro Val Arg Ala Pro Gln Val Tyr Val Leu Pro Pro
            355                 360                 365

Pro Glu Glu Glu Met Thr Lys Lys Gln Val Thr Leu Thr Cys Met Ile
    370                 375                 380

Thr Asp Phe Met Pro Glu Asp Ile Tyr Val Glu Trp Thr Asn Asn Gly
385                 390                 395                 400

Gln Thr Glu Leu Asn Tyr Lys Asn Thr Glu Pro Val Leu Asp Ser Asp
                405                 410                 415

Gly Ser Tyr Phe Met Tyr Ser Lys Leu Arg Val Glu Lys Lys Asn Trp
            420                 425                 430

Val Glu Arg Asn Ser Tyr Ser Cys Ser Val Val His Glu Gly Leu His
            435                 440                 445

Asn His His Thr Thr Lys Ser Phe Ser Arg Thr Pro Gly Lys
    450                 455                 460
```

<210> SEQ ID NO 63
<211> LENGTH: 1107
<212> TYPE: DNA
<213> ORGANISM: Homo sapiens
<220> FEATURE:
<221> NAME/KEY: misc_feature
<222> LOCATION: (1)..(1107)
<223> OTHER INFORMATION: znT8 coding sequence

<400> SEQUENCE: 63

```
atggagtttc ttgaaagaac gtatcttgtg aatgataaag ctgccaagat gtatgctttc      60
acactagaaa gtgtggaact ccaacagaaa ccggtgaata agatcagtg tcccagagag      120 agaccagagg agctggagtc aggaggcatg taccactgcc acagtggctc caagcccaca      180
gaaaaggggg cgaatgagta cgcctatgcc aagtggaaac tctgttctgc ttcagcaata      240
tgcttcattt tcatgattgc agaggtcgtg ggtgggcaca ttgctgggag tcttgctgtt      300
gtcacagatg ctgcccacct cttaattgac ctgaccagtt cctgctcag tctcttctcc      360 ctgtggttgt catcgaagcc tccctctaag cggctgacat ttggatggca ccgagcagag      420
atccttggtg ccctgctctc catcctgtgc atctgggtgg tgactggcgt gctagtgtac      480
ctggcatgtg agcgcctgct gtatcctgat taccagatcc aggcgactgt gatgatcatc      540
gtttccagct gcgcagtggc ggccaacatt gtactaactg tggttttgca ccagagatgc      600
cttggccaca tcacaagga agtacaagcc aatgccagcg tcagagctgc ttttgtgcat      660
gcccttggag atctatttca gagtatcagt gtgctaatta gtgcacttat tatctacttt      720
```

-continued

```
aagccagagt ataaaatagc cgacccaatc tgcacattca tctttccat cctggtcttg      780 gccagcacca tcactatctt aaaggacttc tccatcttac tcatggaagg tgtgccaaag      840
agcctgaatt acagtggtgt gaaagagctt attttagcag tcgacggggt gctgtctgtg      900
cacagcctgc acatctggtc tctaacaatg aatcaagtaa ttctctcagc tcatgttgct      960
acagcagcca gccgggacag ccaagtggtt cggagagaaa ttgctaaagc ccttagcaaa     1020
agctttacga tgcactcact caccattcag atggaatctc cagttgacca ggaccccgac     1080
tgccttttct gtgaagaccc ctgtgac                                         1107
```

<210> SEQ ID NO 64
<211> LENGTH: 369
<212> TYPE: PRT
<213> ORGANISM: Homo sapiens
<220> FEATURE:
<221> NAME/KEY: MISC_FEATURE
<222> LOCATION: (1)..(369)
<223> OTHER INFORMATION: znT8 full length amino acid sequence
<220> FEATURE:
<221> NAME/KEY: MISC_FEATURE
<222> LOCATION: (66)..(369)
<223> OTHER INFORMATION: znT8 amino acid sequence without the N-terminal
      domain
<220> FEATURE:
<221> NAME/KEY: MISC_FEATURE
<222> LOCATION: (276)..(369)
<223> OTHER INFORMATION: znT8 cytoplasmic domain

<400> SEQUENCE: 64

```
Met Glu Phe Leu Glu Arg Thr Tyr Leu Val Asn Asp Lys Ala Ala Lys
1               5                   10                  15

Met Tyr Ala Phe Thr Leu Glu Ser Val Glu Leu Gln Gln Lys Pro Val
            20                  25                  30

Asn Lys Asp Gln Cys Pro Arg Glu Arg Pro Glu Glu Leu Glu Ser Gly
        35                  40                  45

Gly Met Tyr His Cys His Ser Gly Ser Lys Pro Thr Glu Lys Gly Ala
    50                  55                  60

Asn Glu Tyr Ala Tyr Ala Lys Trp Lys Leu Cys Ser Ala Ser Ala Ile
65                  70                  75                  80

Cys Phe Ile Phe Met Ile Ala Glu Val Val Gly Gly His Ile Ala Gly
                85                  90                  95

Ser Leu Ala Val Val Thr Asp Ala Ala His Leu Leu Ile Asp Leu Thr
            100                 105                 110

Ser Phe Leu Leu Ser Leu Phe Ser Leu Trp Leu Ser Ser Lys Pro Pro
        115                 120                 125

Ser Lys Arg Leu Thr Phe Gly Trp His Arg Ala Glu Ile Leu Gly Ala
    130                 135                 140

Leu Leu Ser Ile Leu Cys Ile Trp Val Val Thr Gly Val Leu Val Tyr
145                 150                 155                 160

Leu Ala Cys Glu Arg Leu Leu Tyr Pro Asp Tyr Gln Ile Gln Ala Thr
                165                 170                 175

Val Met Ile Ile Val Ser Ser Cys Ala Val Ala Ala Asn Ile Val Leu
            180                 185                 190

Thr Val Val Leu His Gln Arg Cys Leu Gly His Asn His Lys Glu Val
        195                 200                 205

Gln Ala Asn Ala Ser Val Arg Ala Ala Phe Val His Ala Leu Gly Asp
    210                 215                 220

Leu Phe Gln Ser Ile Ser Val Leu Ile Ser Ala Leu Ile Ile Tyr Phe
225                 230                 235                 240
```

```
Lys Pro Glu Tyr Lys Ile Ala Asp Pro Ile Cys Thr Phe Ile Phe Ser
            245                 250                 255

Ile Leu Val Leu Ala Ser Thr Ile Thr Ile Leu Lys Asp Phe Ser Ile
            260                 265                 270

Leu Leu Met Glu Gly Val Pro Lys Ser Leu Asn Tyr Ser Gly Val Lys
            275                 280                 285

Glu Leu Ile Leu Ala Val Asp Gly Val Leu Ser Val His Ser Leu His
            290                 295                 300

Ile Trp Ser Leu Thr Met Asn Gln Val Ile Leu Ser Ala His Val Ala
305                 310                 315                 320

Thr Ala Ala Ser Arg Asp Ser Gln Val Val Arg Arg Glu Ile Ala Lys
            325                 330                 335

Ala Leu Ser Lys Ser Phe Thr Met His Ser Leu Thr Ile Gln Met Glu
            340                 345                 350

Ser Pro Val Asp Gln Asp Pro Asp Cys Leu Phe Cys Glu Asp Pro Cys
            355                 360                 365

Asp
```

CELL-BASED ZNT8 ASSAY

CROSS-REFERENCE TO RELATED APPLICATIONS

This application claims the benefit of U.S. Provisional Application No. 62/908,761, filed Oct. 1, 2019, which is incorporated herein by reference in its entirety.

STATEMENT OF GOVERNMENTAL INTEREST

This invention was made with government support under grant no. GM065137, awarded by the National Institutes of Health. The government has certain rights in the invention.

FIELD OF THE INVENTION

The present invention relates to the fields of immunology and diabetes. More specifically, the present invention provides methods and compositions directed to the use of antibodies to quantify cellular pancreatic zinc transporter 8.

INCORPORATION-BY-REFERENCE OF MATERIAL SUBMITTED ELECTRONICALLY

This application contains a sequence listing. It has been submitted electronically via EFS-Web as an ASCII text file entitled "P15832-02_ST25.txt." The sequence listing is 74,667 bytes in size, and was created on Dec. 1, 2020. It is hereby incorporated by reference in its entirety.

BACKGROUND OF THE INVENTION

The human genome encodes a multitude of zinc transporters involved in regulation of cellular zinc homeostasis and signaling. Among all zinc transporters, Zinc Transporter-8 (ZnT8) is unique in its tissue-specific expression. Microarray profiling of mouse tissues and single-cell transcriptome profiling of human pancreatic islets showed that SLC30A8 transcription is mostly restricted to the endocrine cells of pancreatic islets. The transcriptional profile of SLC30A8 has a similar degree of islet specificity to that of well-known β-cell markers such as PDX1 and NKX6.1. Single cell RNAseq showed that these β-cell markers also had "spill-over" transcription to non-β-endocrine cells, but the "spill-over" did not extend to exocrine or ductal cells. In islet β-cells, ZnT8 is primarily expressed in insulin secretory granules where ZnT8 is required for granular zinc enrichment and zinc-insulin crystalline packaging in the form of hexameric insulins. The zinc content within insulin granules is over 10 mM. This high zinc level is implicated in insulin synthesis, storage, regulation of insulin secretion and hepatic insulin clearance following glucose stimulated insulin secretion (GSIS).

Islet β-cells are the sole source in the human body for providing insulin. Insufficient insulin production is a major pathogenic component of type-2 diabetes (T2D). The common T2D is a complex polygenic disease associated with more than 150 T2D-risk genes. Until now, SLC30A8 is the only one known for harboring protective loss-of-function (LOF) mutations. Genotyping ~150,000 individuals across multiple population cohorts revealed that carriers of LOF mutations had a 65% lower risk for T2D. This unique position of SLC30A8 in the genetic landscape of T2D susceptibility makes ZnT8 an attractive therapeutic target. Notably, a missense single-nucleotide polymorphism in SLC30A8 (rs13266634) is associated with increased susceptibility to T2D. Zinc transport activity of the higher-risk R325 variant is hyperactive compared with the lower-risk W325 variant, corresponding to a higher zinc level in human pancreatic islets from donors carrying the R325 variant. Moreover, transgenic mice overexpressing the R325 variant increased islet zinc level and decreased glucose tolerance after a high-fat diet, although GSIS phenotypes of ZnT8 KO-mouse models were heterogeneous. Emerging evidence from ZnT8 biochemistry, animal models and human genetics seems coalesced to suggest a causal relationship linking the gain-of-function R235 variant and increased T2D risk, supporting the case for ZnT8 inhibition as a potential antidiabetogenic strategy.

Two alternative approaches may be used to downregulate ZnT8 activity in β-cells: inhibiting zinc transport or reducing ZnT8 expression. The mechanism driving zinc transport is conserved from bacteria to humans. In a bacterial homolog YiiP (28), zinc transport is susceptible to allosteric regulation by zin binding to a cytosolic C-terminal domain (CTD) (29). Likewise, allostery may be targeted for ZnT8 inhibition using mAb to trap ZnT8 in a fixed conformation, but a proof-of-principle allosteric inhibitor is still lacking. Moreover, functional regulation of ZnT8 expression in β-cells has yet to be investigated due to a lack of ZnT8-specific reagents for tracking the cellular ZnT8 level over a heterogenous background. Discovering specific and high affinity mAbs would permit testing the allosteric inhibition hypothesis while developing assays to quantify the cellular ZnT8 level.

SUMMARY OF THE INVENTION

The present invention is based, at least in part, on the development of an assay to quantify the cellular ZnT8 level. Such assays can be used to screen for ZnT8 modulators using an anti-ZnT8 antibody or antigen-binding fragment thereof and human pancreatic beta cells. The assay can be used to identify agonists or antagonists of ZnT8. In certain embodiments, inhibitors of ZnT8 that mimic the naturally occurring LOF mutations to prevent type-2 diabetes in humans can be identified. In particular embodiments, compounds that decrease ZnT8 amount following cytokine stress can be identified. In other embodiments, compounds that rescue ZnT8 degradation following cytokine stress can be identified.

Accordingly, in one aspect, the present invention provides compositions and methods useful for screening for modulators of ZnT8. In one embodiment, a method comprises the steps of (a) permeabilizing human beta cells present in a substrate; (b) contacting the cells with a test agent; and (c) measuring the amount of zinc transporter 8 (ZnT8) using at least one anti-ZnT8 antibody or antigen-binding fragment thereof.

In another embodiment, a method of identifying a modulator of ZnT8 comprises the steps of (a) contacting human beta cells with a test agent; and (b) detecting a change in the amount of ZnT8 in the cell as compared to the amount of ZnT8 in a cell not contacted with the test agent, wherein the detecting step utilizes at least one anti-ZnT8 antibody or antigen-binding fragment thereof.

In a further embodiment, a method of identifying a modulator of ZnT8 comprising the steps of (a) contacting human beta cells with a metabolic or cytokine stressor; (b) contacting the cells with a test agent; and (c) detecting a change in the amount of ZnT8 in the cell as compared to the amount of ZnT8 in a cell contacted with the stressor but not contacted with the test agent, wherein the detecting step utilizes at least one anti-ZnT8 antibody or antigen-binding fragment thereof. In particular embodiments, the metabolic stressor comprises glucose and palmitic acid. In other embodiments, the cytokine stressor comprises one or more of IL-1β, TNF-α, IFN-γ, and IL-17. In any of the foregoing embodiments, the measuring or detecting step comprises a proximity ligation assay.

In certain embodiments, the human beta cells comprise the cell line EndoC-βH1. In another embodiment, the human beta cells comprise the cell line EndoC-βH2. In yet another embodiment, the human beta cells comprise the cells line EndoC-βH2. The cells can comprise one of 1.1B4, 1.4E7 or 1.1E7. In other embodiments, the human beta cells are differentiated from human pluripotent stem cells (hPSCs). In another embodiment, the human beta cells comprise primary pancreatic islets. In a further embodiment, the human beta cells comprise pseudoislets.

In particular embodiments of the present invention, the at least one anti-ZnT8 antibody specifically binds ZnT8 antibody with a high signal-to-noise ratio as compared to other ZnT paralogs and high-abundant cellular proteins present in the human beta cells.

In one embodiment, the at least one anti-ZnT8 antibody or antigen-binding fragment thereof comprises a Fab. In a specific embodiment, the Fab comprises SEQ ID NO:32 and SEQ ID NO:37. In an alternative embodiment, the Fab comprises (a) heavy chain complementary determining regions (CDRs) 1, 2, and 3, wherein the heavy chain CDR1 comprises SEQ ID NO:33, or the amino acid sequence of SEQ ID NO:33 with a substitution at two or fewer amino acid positions, the heavy chain CDR2 comprises SEQ ID NO:34, or the amino acid sequence of SEQ ID NO:34 with a substitution at two or fewer amino acid positions, and the heavy chain CDR3 comprises SEQ ID NO:35, or the amino acid sequence of SEQ ID NO:35 with a substitution at two or fewer amino acid positions; and (b) light chain CDRs 1, 2, and 3, wherein the light chain CDR1 comprises SEQ ID NO:38, or the amino acid sequence of SEQ ID NO:38 with a substitution at two or fewer amino acid positions, the light chain CDR2 comprises SEQ ID NO:39, or the amino acid sequence of SEQ ID NO:39 with a substitution at two or fewer amino acid positions, and the light chain CDR3 comprises SEQ ID NO:40, or the amino acid sequence of SEQ ID NO:40 with a substitution at two or fewer amino acid positions.

In an alternative embodiment, the at least one anti-ZnT8 antibody or antigen-binding fragment thereof comprises (a) a first Fab comprising SEQ ID NO:32 and SEQ ID NO:37; and a second Fab comprising SEQ ID NO:52 and SEQ ID NO:57.

In another specific embodiment, the at least one detectably labeled anti-ZnT8 antibody or antigen-binding fragment thereof comprises (a) a first Fab comprising (i) heavy chain complementary determining regions (CDRs) 1, 2, and 3, wherein the heavy chain CDR1 comprises SEQ ID NO:33, or the amino acid sequence of SEQ ID NO:33 with a substitution at two or fewer amino acid positions, the heavy chain CDR2 comprises SEQ ID NO:34, or the amino acid sequence of SEQ ID NO:34 with a substitution at two or fewer amino acid positions, and the heavy chain CDR3 comprises SEQ ID NO:35, or the amino acid sequence of SEQ ID NO:35 with a substitution at two or fewer amino acid positions, and (ii) light chain CDRs 1, 2, and 3, wherein the light chain CDR1 comprises SEQ ID NO:38, or the amino acid sequence of SEQ ID NO:38 with a substitution at two or fewer amino acid positions, the light chain CDR2 comprises SEQ ID NO:39, or the amino acid sequence of SEQ ID NO:39 with a substitution at two or fewer amino acid positions, and the light chain CDR3 comprises SEQ ID NO:40, or the amino acid sequence of SEQ ID NO:40 with a substitution at two or fewer amino acid positions; and (b) a second Fab comprising (i) heavy chain complementary determining regions (CDRs) 1, 2, and 3, wherein the heavy chain CDR1 comprises SEQ ID NO:53, or the amino acid sequence of SEQ ID NO:53 with a substitution at two or fewer amino acid positions, the heavy chain CDR2 comprises SEQ ID NO:54, or the amino acid sequence of SEQ ID NO:54 with a substitution at two or fewer amino acid positions, and the heavy chain CDR3 comprises SEQ ID NO:55, or the amino acid sequence of SEQ ID NO:55 with a substitution at two or fewer amino acid positions, and (ii) light chain CDRs 1, 2, and 3, wherein the light chain CDR1 comprises SEQ ID NO:58, or the amino acid sequence of SEQ ID NO:58 with a substitution at two or fewer amino acid positions, the light chain CDR2 comprises SEQ ID NO:59, or the amino acid sequence of SEQ ID NO:59 with a substitution at two or fewer amino acid positions, and the light chain CDR3 comprises SEQ ID NO:60, or the amino acid sequence of SEQ ID NO:60 with a substitution at two or fewer amino acid positions.

In further embodiments, the at least one anti-ZnT8 antibody or antigen-binding fragment thereof comprises SEQ ID NO:2 and SEQ ID NO:7; SEQ ID NO:12 and SEQ ID NO:17; SEQ ID NO:22 and SEQ ID NO:27; SEQ ID NO:32 and SEQ ID NO:37; SEQ ID NO:42 and SEQ ID NO:47; or SEQ ID NO:52 and SEQ ID NO:57.

In other specific embodiments, the at least one anti-ZnT8 antibody or antigen-binding fragment thereof comprises (a) (i) heavy chain CDRs 1, 2, and 3, wherein the heavy chain CDR1 comprises SEQ ID NO:3, or the amino acid sequence of SEQ ID NO:3 with a substitution at two or fewer amino acid positions, the heavy chain CDR2 comprises SEQ ID NO:4, or the amino acid sequence of SEQ ID NO:4 with a substitution at two or fewer amino acid positions, and the heavy chain CDR3 comprises SEQ ID NO:5, or the amino acid sequence of SEQ ID NO:5 with a substitution at two or fewer amino acid positions, and (a) (ii) light chain CDRs 1, 2, and 3, wherein the light chain CDR1 comprises SEQ ID NO:8, or the amino acid sequence of SEQ ID NO:8 with a substitution at two or fewer amino acid positions, the light chain CDR2 comprises SEQ ID NO:9, or the amino acid sequence of SEQ ID NO:9 with a substitution at two or fewer amino acid positions, and the light chain CDR3 comprises SEQ ID NO:10, or the amino acid sequence of SEQ ID NO:10 with a substitution at two or fewer amino acid positions; or (b) (i) heavy chain CDRs 1, 2, and 3, wherein the heavy chain CDR1 comprises SEQ ID NO:13, or the amino acid sequence of SEQ ID NO:13 with a substitution at two or fewer amino acid positions, the heavy chain CDR2 comprises SEQ ID NO:14, or the amino acid sequence of SEQ ID NO:14 with a substitution at two or fewer amino acid positions, and the heavy chain CDR3 comprises SEQ ID NO:15, or the amino acid sequence of SEQ ID NO:15 with a substitution at two or fewer amino acid positions, and (b) (ii) light chain CDRs 1, 2, and 3, wherein the light chain CDR1 comprises SEQ ID NO:18, or the amino acid sequence of SEQ ID NO:18 with a substitution at two or fewer amino acid positions, the light chain CDR2 comprises SEQ ID NO:19, or the amino acid sequence of SEQ ID NO:19 with a substitution at two or fewer amino acid positions, and the light chain CDR3 comprises SEQ ID NO:20, or the amino acid sequence of SEQ ID NO:20 with a substitution at two or fewer amino acid positions; or (c) (i) heavy chain CDRs 1, 2, and 3, wherein the heavy chain CDR1 comprises SEQ ID NO:23, or the amino acid sequence of SEQ ID NO:23 with a substitution at two or fewer amino acid positions, the heavy chain CDR2 comprises SEQ ID NO:24, or the amino acid sequence of SEQ ID NO:24 with a substitution at two or fewer amino acid positions, and the heavy chain CDR3 comprises SEQ ID NO:25, or the amino acid sequence of SEQ ID NO:25 with a substitution at two or fewer amino acid positions, and (c) (ii) light chain CDRs 1, 2, and 3, wherein the light chain CDR1 comprises SEQ ID NO:28, or the amino acid sequence of SEQ ID NO:28 with a substitution at two or fewer amino acid positions, the light chain CDR2 comprises SEQ ID NO:29, or the amino acid sequence of SEQ TD NO:29 with a substitution at two or fewer amino acid positions, and the light chain CDR3 comprises SEQ ID NO:30, or the amino acid sequence of SEQ ID NO:30 with a substitution at two or fewer amino acid positions; or (d) (i) heavy chain CDRs 1, 2, and 3, wherein the heavy chain CDR1 comprises SEQ ID NO:33, or the amino acid sequence of SEQ ID NO:33 with a substitution at two or fewer amino acid positions, the heavy chain CDR2 comprises SEQ ID NO:34, or the amino acid sequence of SEQ ID NO:34 with a substitution at two or fewer amino acid positions, and the heavy chain CDR3 comprises SEQ ID NO:35, or the amino acid sequence of SEQ ID NO:35 with a substitution at two or fewer amino acid positions, and (d) (ii) light chain CDRs 1, 2, and 3, wherein the light chain CDR1 comprises SEQ ID NO:38, or the amino acid sequence of SEQ ID NO:38 with a substitution at two or fewer amino acid positions, the light chain CDR2 comprises SEQ ID NO:39, or the amino acid sequence of SEQ ID NO:39 with a substitution at two or fewer amino acid positions, and the light chain CDR3 comprises SEQ ID NO:40, or the amino acid sequence of SEQ ID NO:40 with a substitution at two or fewer amino acid positions;

(e) (i) heavy chain CDRs 1, 2, and 3, wherein the heavy chain CDR1 comprises SEQ ID NO:43, or the amino acid sequence of SEQ ID NO:43 with a substitution at two or fewer amino acid positions, the heavy chain CDR2 comprises SEQ ID NO:44, or the amino acid sequence of SEQ ID NO:44 with a substitution at two or fewer amino acid positions, and the heavy chain CDR3 comprises SEQ ID NO:45, or the amino acid sequence of SEQ ID NO:45 with a substitution at two or fewer amino acid positions, and (e) (ii) light chain CDRs 1, 2, and 3, wherein the light chain CDR1 comprises SEQ ID NO:48, or the amino acid sequence of SEQ ID NO:48 with a substitution at two or fewer amino acid positions, the light chain CDR2 comprises SEQ ID NO:49, or the amino acid sequence of SEQ ID NO:49 with a substitution at two or fewer amino acid positions, and the light chain CDR3 comprises SEQ ID NO:50, or the amino acid sequence of SEQ ID NO:50 with a substitution at two or fewer amino acid positions; or (f) (i) heavy chain CDRs 1, 2, and 3, wherein the heavy chain CDR1 comprises SEQ ID NO:53, or the amino acid sequence of SEQ ID NO:53 with a substitution at two or fewer amino acid positions, the heavy chain CDR2 comprises SEQ ID NO: 54, or the amino acid sequence of SEQ ID NO:54 with a substitution at two or fewer amino acid positions, and the heavy chain CDR3 comprises SEQ ID NO:55, or the amino acid sequence of SEQ ID NO:55 with a substitution at two or fewer amino acid positions, and (f) (ii) light chain CDRs 1, 2, and 3, wherein the light chain CDR1 comprises SEQ ID NO:58, or the amino acid sequence of SEQ ID NO:58 with a substitution at two or fewer amino acid positions, the light chain CDR2 comprises SEQ ID NO:59, or the amino acid sequence of SEQ ID NO:59 with a substitution at two or fewer amino acid positions, and the light chain CDR3 comprises SEQ ID NO:60, or the amino acid sequence of SEQ ID NO:60 with a substitution at two or fewer amino acid positions.

BRIEF DESCRIPTION OF THE FIGURES

FIG. 1A: Linear response of ZnT8-ELISA readout with an increasing number of EndoC-βH1 (red), INS-1E (blue) and HEK293 cells (dark cyan). Solid lines are linear regressions of mean values of four to eight replicated measurements for each datapoint. Error bars are standard deviations. The coefficient of determination (r2) for fitted regression lines range from 0.98 to 1.00. FIG. 1B: Linear response of ZnT8-ELISA readout with increasing ZnT8 expression in HEK293 cells (r2=1.00). The number of ZnT8-expressing cells in each well was increased from 0 to 10×103 and the number of ZnT8-negative cells adjusted to give a total number of 30×103 cells in each well. ZnT8 expression was induced by doxycycline for 16 hr. LOQ is 10× standard deviation above the background. FIG. 1C: Linear response of ZnT8-ELISA readout to purified ZnT8.

FIG. 2A-2F. Perturbation of endogenous ZnT8 expression. FIG. 2A-2C: Dose responses of the endogenous ZnT8 level as a function of Glc+PA (green), zinc (blue) or cytokine concentration (red). Filled circles are means of eight replicated measurements (diamonds) with standard deviations shown as error bars. FIG. 2D: Time course of cytokine-induced ZnT8 downregulation. Solid line is an exponential fit of the time course (r2=0.99). Error bars are standard deviations of eight replicated measurements from one representative experiment. FIG. 2E: Time course of ZnT8 recovery after removal of cytokines at t=0. Ctr indicates untreated control. Solid line is an exponential fit of the time course (r2=0.99). FIG. 2F Time courses of normalized CellTox fluorescence intensities in response to different concentrations of Glc+PA, zinc and cytokine exposures as indicated. The relative CellTox fluorescence intensity was normalized to that induced by detergent-induced cell lysis. Filled circles are means of eight replicated measurements and error bars standard deviations.

FIG. 3A-3D. Effects of cytokine and metabolic stress on proteins in different subcellular locations. FIG. 3A: Immunoblotting analysis of total cell lysate from ~2×104 EndoC-βH1 cells with or without stress exposure as indicated. ZnT8 and α-tubulin were probed with respective antibodies at the same time on the same immunoblot. Two ZnT8 splice variants are marked as A and B, respectively. FIG. 3B: immunoblotting analysis of total cell lysate using antibodies to BAP31, calnexin, IA2. VAMP2 and TMED3 as indicated. FIG. 3C: immunoblotting analysis of total cell lysates using antibodies to GAD65 and SCD as indicated (upper panel), and responses of four β-cell autoantigens and SCD to cytokine (red) or metabolic stress (green) as indicated (lower panel). Respective protein band intensities were quantified and normalized to that of untreated controls on the same immunoblots. FIG. 3D: Densitometric quantification of ZnT8, α-tubulin and BAP31 at different time points of cytokine (red) and Glc+PA exposures (green). Protein band intensities were normalized to that of untreated controls on the same immunoblots. *** indicate statistical significance by paired t-test with p<0.001. Error bars are standard errors of eight measurements from four independent experiments.

FIG. 5A: ZnT8 probed by mAb20 immunoblotting using liposomes from 1×106 cells before and after bound to mAb20- or IgG-beads followed by SDS-elution. FIG. 5B: Co-immunoprecipitation of ZnT8 and organelle markers. ZnT8-liposomes were captured by mAb20-beads, eluted and then probed by an antibody to BAP31, IA2, TMED3, VAMP2 or Golgin97 as indicated. Pre-bound liposomes and IgG-bead bound liposomes were used as a positive and negative control, respectively. Of note, gel loading of pre-bound liposomes was half of the mAb20-bead bound liposomes. FIG. 5C: Quantification of ER-resident ZnT8. Upper panel, a representative mAb20-immunoblotting of liposomes before and after incubation with anti-BAP31-beads. Liposomes in the flow-through and SDS-elution of BAP31-beads are marked as unbound and bound, respectively Lower panel, densitometric quantification of ZnT8 intensity of total liposomes, unbound and bound fractions. ZnT8 intensities were normalized to the intensity of total liposomes on the same immunoblot. Error bars are standard errors of four independent experiments. FIG. 5D: Cytokine-induced reduction of ER-resident ZnT8. Upper panel, a representative mAb20 immunoblotting of liposomes from an equal number of EndoC-βH1 cells (1×106). Ctr and Cyt indicate liposomes from untreated control and cytokine-treated cells, respectively. Ctr-bound and Cyt-bound are captured Ctr- and Cyt-liposomes on anti-BAP31-beads with SDS-elution. Lower panel, densitometric quantification of ZnT8 intensities with normalization to the Ctr intensity on the same immunoblot. Error bars are standard errors of mean values from 4 independent experiments. FIG. 5E: Confocal microscopy imaging of EndoC-βH1 cells with and without exposure to 1× cytokine cocktail for 24 hr, and then co-immunostained with mouse mAb20 and a rabbit anti-insulin pAb. Scale bars are 5 μm.

FIG. 6A-6C: Responses of HLA-I molecules to metabolic and cytokine stress. FIG. 6A: Anti-HLA-I immunoblotting analysis of cell lysates of EndoC-βH1 cells with cytokine and metabolic pre-exposures as indicated. ZnT8 on the same immunoblot was probed with mAb20 as a reference. FIG. 6B: Dose-dependent response of HLA-I molecules to cytokine exposures. Filled circles and error bars are means and standard deviations of eight replicated measurements (diamonds) by HLA-I ELISA. FIG. 6C: Correlation of endogenous ZnT8 and HLA-I expression. Data points (filled circles) were taken from FIG. 2C and FIG. 6B for endogenous ZnT8 and HLA-I levels over a range of identical cytokine concentrations. Error bars are standard deviations and the solid line a liner regression (r2=0.77).

FIG. 7A: GSIS from EndoC-βH1 cells that were pre-exposed to different concentrations of Glc+PA (green), zinc (blue) and cytokines (red) for 24 hr. Filled circles and error bars are means and standard deviations of eight replicated measurements (diamonds). FIG. 7B: Insulin content in EndoC-βH1 cells under identical stress exposures as in FIG. 7A. FIG. 7C: Correlations of ZnT8 expression and insulin production under different stress conditions. Data points were generated using the endogenous ZnT8 levels from FIG. 2A-C and insulin contents from FIG. 7B measured under identical stress exposures. Solid lines are linear regressions and the levels of ZnT8-insulin correlation are indicated by respective r2 values.

FIG. 8A-SC. Transcriptomic analysis of EndoC-βH1 cells in response to cytokine exposure. FIG. 8A: Overlap of distributions of mRNA levels in the EndoC-βH1 transcriptome with (red) or without (black) 1× cytokine exposure for 24 hr. Black line indicates the SLC30A8 mRNA level in EndoC-βH cells. Dashed magenta line indicates a 10-fold increase of the SLC30A mRNA level in human pancreatic β-cells (82). FIG. 8B: m RNA levels of ZnT(SLC30) and ZIP(SLC39) gene families in EndoC-βH1 cells. Error bars are standard deviations of three biological replicates. FIG. 8C: Correlation of mRNA levels with and without cytokine exposure along a diagonal line. Off-diagonal datapoints indicate cytokine-induced transcriptional changes. Red data points are LMP2, LMP7 and MECl-1 transcripts, and blue datapoints are other UPR-related transcripts listed in Table-1.

FIG. 9A: anti-ZnT8 immunoblotting of EndoC-βH1 cells following a 24 hr exposure to 1× cytokines or 1 μM epoxomicin in various combinations as indicated (upper panel), cellular insulin contents measured in parallel (lower panel). FIG. 9B: Normalized CellTox fluorescence intensities in response to 1× cytokines or 1 μM epoxomicin in various combinations as indicated. C. anti-ZnT8 immunoblotting of EndoC-βH1 cells treated with ZnT8-targeting or scrambled siRNA as indicated. D. Normalized CellTox fluorescence intensities in response to 15× cytokine exposure for 24 hr. EndoC-βH1 cells were pre-treated with ZnT8-targeting or scrambled siRNA as indicated. Error bars are standard deviations of 4 independent measurements.

DETAILED DESCRIPTION OF THE INVENTION

Figure 1A:
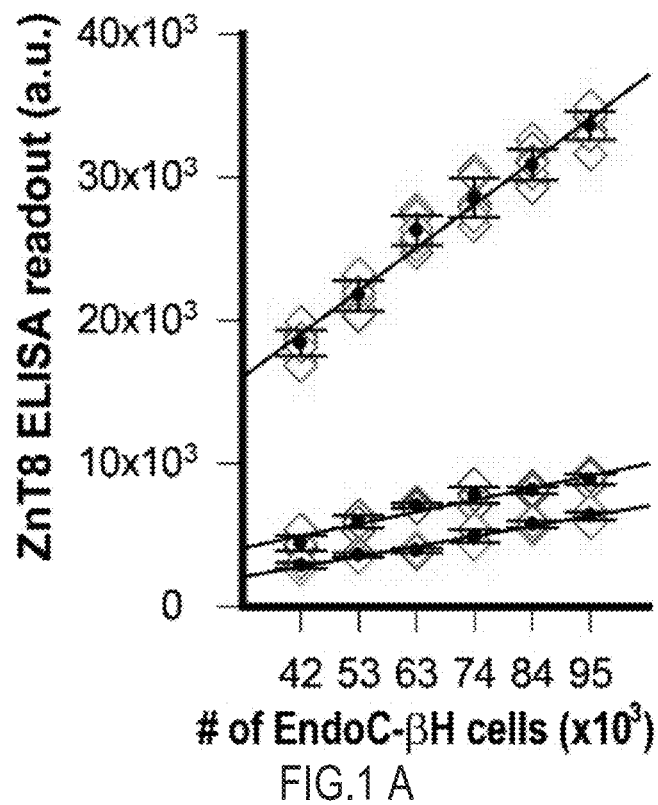
FIG. 1A-1C. Assay calibration.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the articles "a" and "an" are used to refer to one or to more than one (i.e., to at least one) of the grammatical object of the article. By way of example, "an element" means one element or more than one element.

As used herein, "about," when referring to a measurable value such as an amount, a temporal duration, and the like, is meant to encompass variations of +20% or +10%, more preferably +5%, even more preferably +1%, and still more preferably +0.1% from the specified value, as such variations are appropriate to perform the disclosed methods.

As used herein, the term "T1D" refers to type 1 diabetes.

The term "antibody" means an immunoglobulin molecule that recognizes and specifically binds to a target, such as a protein (e.g., the ZnT8, a subunit thereof, or the receptor complex), polypeptide, peptide, carbohydrate, polynucleotide, lipid, or combinations of the foregoing through at least one antigen recognition site within the variable region of the immunoglobulin molecule. A typical antibody comprises at least two heavy (HC) chains and two light (LC) chains interconnected by disulfide bonds. Each heavy chain is comprised of a "heavy chain variable region" or "heavy chain variable domain" (abbreviated herein as VH) and a heavy chain constant region (CH), The heavy chain constant region is comprised of three domains, CH1, CH2, and CH3. Each light chain is comprised of a "light chain variable region" or "light chain variable domain" (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FRs). Each VH and VL region is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. As used herein, the term "antibody" encompasses intact polyclonal antibodies, intact monoclonal antibodies, antibody fragments (such as Fab, Fab', F(ab')2, Fd, Facb, and Fv fragments), single chain Fv (scFv), minibodies (e.g., sc(Fv) 2, diabody), multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. Thus, the term "antibody" includes whole antibodies and any antigen-binding fragment or single chains thereof. Antibodies can be naked or conjugated to other molecules such as toxins, detectable labels, radioisotopes, small molecule drugs, polypeptides, etc.

The term "isolated antibody" refers to an antibody that has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody is purified (1) to greater than 95% by weight of antibody as determined by, for example, the Lowry method, and including more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or silver stain. An isolated antibody includes the antibody in situ within recombinant cells since at least one component of the antibody's natural environment will not be present. Ordinarily, however, isolated antibody will be prepared by at least one purification step.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, "substantially purified" refers to being essentially free of other components. For example, a substantially purified polypeptide is a polypeptide which has been separated from other components with which it is normally associated in its naturally occurring state.

The term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined herein, e.g., because the entire variable region of a chimeric antibody is non-human.

The term "antigen" is generally used in reference to any substance that is capable of reacting with an antibody. An antigen can also refer to a synthetic peptide, polypeptide, protein or fragment of a polypeptide or protein, or other molecule which elicits an antibody response in a subject, or is recognized and bound by an antibody.

The term "antigen-binding fragment" refers to a portion of an intact antibody and refers to the antigenic determining, variable regions of an intact antibody. It is known in the art that the antigen-binding function of an antibody can be performed by fragments of a full-length antibody. Examples of antigen-binding antibody fragments include, but are not limited to Fab, Fab', F(ab')2, Facb, Fd, and Fv fragments, linear antibodies, single chain antibodies, and multi-specific antibodies formed from antibody fragments. In some instances, antibody fragments may be prepared by proteolytic digestion of intact or whole antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

The term "Fab" refers to an antibody fragment that is essentially equivalent to that obtained by digestion of immunoglobulin (typically IgG) with the enzyme papain. The heavy chain segment of the Fab fragment is the Fd piece. Such fragments can be enzymatically or chemically produced by fragmentation of an intact antibody, recombinantly produced from a gene encoding the partial antibody sequence, or it can be wholly or partially synthetically produced. The term "F(ab')2" refers to an antibody fragment that is essentially equivalent to a fragment obtained by digestion of an immunoglobulin (typically IgG) with the enzyme pepsin at pH 4.0-4.5. Such fragments can be enzymatically or chemically produced by fragmentation of an intact antibody, recombinantly produced from a gene encoding the partial antibody sequence, or it can be wholly or partially synthetically produced. The term "Fv" refers to an antibody fragment that consists of one NH and one N domain held together by noncovalent interactions.

The terms "ZnT8 antibody," "anti-ZnT8 antibody," "anti-ZnT8," "antibody that binds to ZnT8" and any grammatical variations thereof refer to an antibody that is capable of specifically binding to ZnT8 with sufficient affinity such that the antibody could be useful, for example, as a therapeutic agent or diagnostic reagent in targeting ZnT8. The extent of binding of an anti-ZnT8 antibody disclosed herein to an unrelated, non-ZnT8 protein is less than about 10% of the binding of the antibody to ZnT8 as measured, e.g., by a radioimmunoassay (RIA), BIACORE™ (using recombinant ZnT8 as the analyte and antibody as the ligand, or vice versa), or other binding assays known in the art. In certain embodiments, an antibody that binds to ZnT8 has a dissociation constant (KD) of <1 µM, <100 nM, <50 nM, <10 nM, or <1 nM.

The term "% identical" ("sequence identity") between two polypeptide (or polynucleotide) sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site. Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence. One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2 (ClustalX is a version of the ClustalW2 program ported to the Windows environment). Another suitable program is MUSCLE. ClustalW2 and MUSCLE are alternatively available, e.g., from the European Bioinformatics Institute (EBI).

By "detectable label" is meant a composition that when linked (directly or indirectly) to a molecule of interest renders the latter detectable via spectroscopic, photochemical, biochemical, immunochemical, chemical or electrochemiluminescent means. For example, detectable labels include radioactive isotopes, magnetic beads, metallic beads, colloidal particles, fluorescent dyes, electron-dense reagents, enzymes (for example, as commonly used in an ELISA), biotin, digoxigenin, or haptens. The labeling of an antigen can be carried out by any generally known method. Examples of the detectable label known to those skilled in the art include a fluorescent dye, an enzyme, a coenzyme, a chemiluminescent substance or a radioactive substance. Specific examples may include radioisotopes ($^{32}P$, $^{14}C$, $^{125}I$, $^{3}H$, $^{131}I$ and the like), fluorescein, rhodanine, dansyl chloride, umbelliferone, luciferase, peroxidase, alkaline phosphatase, beta-galactosidase, beta-glucosidase, horseradish peroxidase, glucoamylase, lysozyme, saccharide oxidase, microperoxidase, biotin and the like.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

I. Anti-ZnT8 Antibodies

The antibodies or antigen-binding fragment thereof of this disclosure specifically bind to ZnT8. In specific embodiments, these antibodies or antigen-binding fragments specifically bind to human ZnT8. "Specifically binds" as used herein means that the antibody or antigen-binding fragment preferentially binds ZnT8 (e.g., human ZnT8, mouse ZnT8) over other proteins. In certain instances, the anti-ZnT8 antibodies of the disclosure have a higher affinity for ZnT8 than for other proteins. In more particular embodiments, anti-ZnT8 antibodies specifically bind ZnT8 over other ZnT paralogs. Anti-ZnT8 antibodies that specifically bind ZnT8 may have a binding affinity for human ZnT8 of less than or equal to $1 \times 10^{-7}$ M, less than or equal to $2 \times 10^{-7}$ M, less than or equal to $3 \times 10^{-7}$ M, less than or equal to $4 \times 10^{-7}$ M, less than or equal to $5 \times 10^{-7}$ M, less than or equal to $6 \times 10^{-7}$ M, less than or equal to $7 \times 10^{-7}$ M, less than or equal to $8 \times 10^{-7}$ M, less than or equal to $9 \times 10^{-7}$ M, less than or equal to $1 \times 10^{-8}$ M, less than or equal to $2 \times 10^{-8}$ M, less than or equal to $3 \times 10^{-8}$ M, less than or equal to $4 \times 10^{-8}$ M, less than or equal to $5 \times 10^{-8}$ M, less than or equal to $6 \times 10^{-8}$ M, less than or equal to $7 \times 10^{-8}$ M, less than or equal to $8 \times 10^{-8}$ M, less than or equal to $9 \times 10^{-8}$ M, less than or equal to $1 \times 10^{-9}$ M, less than or equal to $2 \times 10^{-9}$ M, less than or equal to $3 \times 10^{-9}$ M, less than or equal to $4 \times 10^{-9}$ M, less than or equal to $5 \times 10^{-9}$ M, less than or equal to $6 \times 10^{-9}$ M, less than or equal to $7 \times 10^{-9}$ M, less than or equal to $8 \times 10^{-9}$ M, less than or equal to $9 \times 10^{-9}$ M, less than or equal to $1 \times 10^{-10}$ M, less than or equal to $2 \times 10^{-10}$ N, less than or equal to $3 \times 10^{-10}$ M, less than or equal to $4 \times 10^{-10}$, less than or equal to $5 \times 10^{-10}$ M, less than or equal to $6 \times 10^{-10}$ M, less than or equal to $7 \times 10^{-10}$ M, less than or equal to $8 \times 10^{-10}$ M, less than or equal to $9 \times 10^{-10}$ M, less than or equal to $1 \times 10^{-11}$ M, less than or equal to $2 \times 10^{-11}$ M, less than or equal to $3 \times 10^{-11}$ M, less than or equal to $4 \times 10^{-11}$ M, less than or equal to $5 \times 10^{-11}$ M, less than or equal to $6 \times 10^{-11}$ M, less than or equal to $7 \times 10^{-11}$ M, less than or equal to $8 \times 10^{-11}$ M, less than or equal to $9 \times 10^{-11}$ M, less than or equal to $1 \times 10^{-12}$ M, less than or equal to $2 \times 10^{-12}$ M, less than or equal to $3 \times 10^{-12}$ M, less than or equal to $4 \times 10^{-12}$ M, less than or equal to $5 \times 10^{-12}$ M, less than or equal to $6 \times 10^{-12}$ M, less than or equal to $7 \times 10^{-12}$ M, less than or equal to $8 \times 10^{-12}$ M, or less than or equal to $9 \times 10^{-12}$ M. Methods of measuring the binding affinity of an antibody are well known in the art and include Surface Plasmon Resonance (SPR) (Morton and Myszka "Kinetic analysis of macromolecular interactions using surface plasmon resonance biosensors" Methods in Enzymology (1998) 295, 268-294), Bio-Layer Interferometry, (Abdiche et al "Determining Kinetics and Affinities of Protein Interactions Using a Parallel Real-time Label-free Biosensor, the Octet" Analytical Biochemistry (2008) 377, 209-217), Kinetic Exclusion Assay (KinExA) (Darling and Brault "Kinetic exclusion assay technology: characterization of molecular interactions" Assay and Drug Dev Tech (2004) 2, 647-657), isothermal calorimetry (Pierce et al "Isothermal Titration Calorimetry of Protein-Protein Interactions" Methods (1999) 19, 213-221) and analytical ultracentrifugation (Lebowitz et al "Modern analytical ultracentrifugation in protein science: A tutorial review" Protein Science (2002), 11:2067-2079).

In a specific embodiment, at least one anti-ZnT8 antibody or antigen-binding fragments thereof are used. In one embodiment, the antibody or antigen-binding fragment thereof comprises a Fab. In particular embodiments, the Fab comprises the heavy chain and light chain of mAb12 (SEQ ID NOS:2 and 7, respectively), mAb16 (SEQ ID NOS: 12 and 17, respectively), mAb17 (SEQ ID NOS:22 and 27, respectively), mAb20 (SEQ ID NOS:32 and 37, respectively), mAb28 (SEQ ID NOS:42 and 47, respectively) or mAb39 (SEQ ID NOS:52 and 57, respectively). In a specific embodiment, the antibody or antigen-binding fragment thereof comprises the heavy chain and light chain of mAb 12 (SEQ ID NOS. 2 and 7, respectively), mAb16 (SEQ ID NOS: 12 and 17, respectively), mAb17 (SEQ ID NOS:22 and 27, respectively), mAb20 (SEQ ID NOS:32 and 37, respectively), mAb28 (SEQ ID NOS: 42 and 47, respectively) or mAb39 (SEQ ID NOS:52 and 57, respectively).

In other embodiments, the Fab comprises heavy chain CDRs 1, 2 and 3 and light chain CDRs 1, 2 and 3. In particular embodiments, a Fab comprises the heavy chain CDRs 1, 2 and 3 and light chain CDRs 1, 2, and 3 of mAb 12 (SEQ ID NOS:3–5 and SEQ ID NOS:8-10, respectively), mAb 16 (SEQ ID NOS:13-15 and SEQ ID NOS:18-20, respectively), mAb 17 (SEQ ID NOS:23-25 and SEQ ID NOS:28-30, respectively), mAb 20 (SEQ ID NOS:33-35 and SEQ ID NOS:38-40, respectively), mAb 28 (SEQ ID NOS: 43-45 and SEQ ID NOS:48-50, respectively), or mAb 39 (SEQ ID NOS:53-55 and SEQ ID NOS:58-60, respectively).

In alternative embodiments, the anti-ZnT8 antibody or antigen-binding fragment thereof comprises heavy chain CDRs 1, 2 and 3 and light chain CDRs 1, 2 and 3. In particular embodiments, the anti-ZnT8 antibody or antigen-binding fragment thereof comprises the heavy chain CDRs 1, 2 and 3 and light chain CDRs 1, 2, and 3 of mAb 12 (SEQ ID NOS:3-5 and SEQ ID NOS:8-10, respectively), mAb 16 (SEQ ID NOS: 13-15 and SEQ ID NOS: 18-20, respectively), mAb 17 (SEQ ID NOS:23-25 and SEQ ID NOS: 28-30, respectively), mAb 20 (SEQ ID NOS:33-35 and SEQ ID NOS:38-40, respectively), mAb 28 (SEQ ID NOS:43-45 and SEQ ID NOS:48-50, respectively), or mAb 39 (SEQ ID NOS:53-55 and SEQ ID NOS:58-60, respectively).

In a specific embodiment, at least two anti-ZnT8 antibodies or antigen-binding fragments thereof are used to bind specifically ZnT8. Each of the at least two anti-ZnT8 antibodies or antigen-binding fragments thereof comprises heavy chain CDRs 1, 2 and 3 and light chain CDRs 1, 2 and 3. In particular embodiments, a first anti-ZnT8 antibody or antigen-binding fragment thereof comprises the heavy chain CDRs 1, 2 and 3 and light chain CDRs 1, 2, and 3 of mAb 20 (SEQ ID NOS:33-35 and SEQ ID NOS:38-40, respectively), and a second anti-ZnT8 antibody or antigen-binding fragment thereof comprises the heavy chain CDRs 1, 2 and 3 and light chain CDRs 1, 2, and 3 of mAb 39 (SEQ ID NOS:53-55 and SEQ ID NOS:58-60, respectively). In alternative embodiments, at least two anti-ZnT8 antibodies or antigen-binding fragments thereof comprise the heavy and light chains or heavy chain CDRs 1, 2, and 3 and light chain CDRs 1, 2 and 3 of mAb12, mAb16, mAb17, mAb20, mAb28 or mAb39.

A. Antibody Fragments

The present disclosure encompasses the antibody fragments or domains described herein that retains the ability to specifically bind to ZnT8 (e.g., human ZnT8). Antibody fragments include, e.g. Fab, Fab, F(ab')2, Facb, and Fv.

These fragments may be humanized or fully human. Antibody fragments may be prepared by proteolytic digestion of intact antibodies. For example, antibody fragments can be obtained by treating the whole antibody with an enzyme such as papain, pepsin, or plasmin. Papain digestion of whole antibodies produces F(ab)2 or Fab fragments; pepsin digestion of whole antibodies yields F(ab')2 or Fab'; and plasmin digestion of whole antibodies yields Facb fragments.

Alternatively, antibody fragments can be produced recombinantly. For example, nucleic acids encoding the antibody fragments of interest can be constructed, introduced into an expression vector, and expressed in suitable host cells. See, e.g., Co, M. S. et al., J Immunol., 152:2968-2976 (1994); Better, M, and Horwitz, A. H., Methods in Enzymology, 178:476-496 (1989); Pluckthun, A and Skerra, A, Methods in Enzymology, 178:476-496 (1989); Lamoyi, E., Methods in Enzymology, 121:652-663 (1989); Rousseaux, J. et al., Methods in Enzymology, (1989) 121:663-669 (1989); and Bird, R E. et al., TIBTECH, 9:132-137 (1991)). Antibody fragments can be expressed in and secreted from *E. coli*, thus allowing the facile production of large amounts of these fragments. Antibody fragments can be isolated from the antibody phage libraries. Alternatively, Fab'-SH fragments can be directly recovered from *E. coli* and chemically coupled to form F(ab)2 fragments (Carter et al., Bio/Technology, 10:163-167 (1992)). According to another approach, F(ab')2 fragments can be isolated directly from recombinant host cell culture. Fab and F(ab') 2 fragment with increased in vivo half-life comprising a salvage receptor binding epitope residues are described in U.S. Pat. No. 5,869,046.

B. Minibodies

Also encompassed are minibodies of the antibodies described herein. Minibodies of anti-ZnT8 antibodies include diabodies, single chain (scFv), and single-chain (Fv)2 (sc(Fv)2).

A "diabody" is a bivalent minibody constructed by gene fusion (see, e.g., Holliger, P. et al., Proc. Natl. Acad. Sci. U.S.A., 90:6444-6448 (1993): EP 404,097: WO 93/11161). Diabodies are dimers composed of two polypeptide chains. The VL and VH domain of each polypeptide chain of the diabody are bound by linkers. The number of amino acid residues that constitute a linker can be between 2 to 12 residues (e.g., 3-10 residues or five or about five residues). The linkers of the polypeptides in a diabody are typically too short to allow the VL and VH to bind to each other. Thus, the VL and VH encoded in the same polypeptide chain cannot form a single-chain variable region fragment, but instead form a dimer with a different single-chain variable region fragment. As a result, a diabody has two antigen-binding sites.

An scFv is a single-chain poly peptide antibody obtained by linking the VH and VL with a linker (see e.g., Huston et al., Proc. Natl. Acad. Sci. U S. A., 85:5879-5883 (1988); and Pluckthun, "The Pharmacology of Monoclonal Antibodies" Vol. 113, Ed Resenburg and Moore, Springer Verlag, New York, pp. 269-315, (1994)). Each variable domain (or a portion thereof) is derived from the same or different anti bodies. Single chain Fv molecules preferably comprise an scFv linker interposed between the VH domain and the VL domain. Exemplary scFv molecules are known in the art and are described, for example, in U.S. Pat. No. 5,892,019; Ho et alt Gene, 77:51 (1989); Bird et al., Science, 242:423 (1988); Pantoliano et al, Biochemistry, 30: 101 17 (1991); Milenic et al, Cancer Research, 51:6363 (1991); Takkinen et al, Protein Engineering, 4:837 (1991).

The term "scFv linker" as used herein refers to a moiety interposed between the VL and VTH domains of the scFv. The scFv linkers preferably maintain the scFv molecule in an antigen-binding conformation. In one embodiment, an scFv linker comprises or consists of an scFv linker peptide. In certain embodiments, an scFv linker peptide comprises or consists of a Gly-Ser peptide linker. In other embodiments, an scFv linker comprises a disulfide bond.

The order of VHs and VLs to be linked is not particularly limited, and they may be arranged in any order. Examples of arrangements include: [VH] linker [VL]; or [VL] linker [VH]. The H chain V region and L chain V region in an scFv may be derived from any anti-ZnT8 antibody or antigen-binding fragment thereof described herein.

An sc(Fv)2 is a minibody in which two VHs and two VLs are linked by a linker to form a single chain (Hudson, et al., J Immunol. Methods, (1999) 231: 177-189 (1999)). An sc(Fv)2 can be prepared, for example, by connecting scFvs with a linker. The sc(Fv)2 of the present invention include antibodies preferably in which two VHs and two VLs are arranged in the order of VH, VL, VH, and VL ([VH] linker [VL] linker [VH] linker [VL]), beginning from the N terminus of a single-chain polypeptide; however, the order of the two VHs and two VLs is not limited to the above arrangement, and they may be arranged in any order. Examples of arrangements are listed below:

[VL] linker [VH] linker [VH] linker [VL]
[VH] linker [VL] linker [VL] linker [VH]
[VH] linker [VH] linker [VL] linker [VL]
[VL] linker [VL] linker [VH] linker [VH]
[VL] linker [VH] linker [VL] linker [VH]

Normally, three linkers are required when four antibody variable regions are linked; the linkers used may be identical or different. There is no particular limitation on the linkers that link the VH and VL regions of the minibodies. In some embodiments, the linker is a peptide linker. Any arbitrary single-chain peptide comprising about 3 to 25 residues (e.g., 5, 6, 7, 8, 9, 10, 11, 12, 13, 14, 15, 16, 17, 18) can be used as a linker.

In other embodiments, the linker is a synthetic compound linker (chemical cross-linking agent). Examples of cross-linking agents that are available on the market include N-hydroxysuccinimide (NHS), disuccinimidylsuberate (DSS), bis(sulfosuccinimidyl)suberate (BS3), dithiobis(succinimidy Ipropionate) (DSP), dithiobis(sulfosuccinimidy Ipropionate) (DTSSP), ethyleneglycol bis(succinimnidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl]sulfone (BSOCOES), and bis[2-(sulfosuccinimidooxycarbonyloxy)ethyl]sulfone (sulfo-BSOCOES).

The amino acid sequence of the VH or VL in the antibody fragments or minibodies may include modifications such as substitutions, deletions, additions, and/or insertions. For example, the modification may be in one or more of the CDRs of the anti-ZnT8 antibodies described herein. In certain embodiments, the modification involves one, two, or three amino acid substitutions in one, two, or three CDRs of the VH and/or one, two, or three CDRs of the VL domain of the anti-ZnT8 minibody. Such substitutions are made to improve the binding and/or functional activity of the anti-ZnT8 minibody. In other embodiments, one, two, or three amino acids of one or more of the six CDRs of the anti-ZnT8 antibody or antigen-binding fragment thereof may be deleted or added as long as there is ZnT8 binding and/or functional activity when VH and VL are associated.

C. VHH

VHH also known as nanobodies are derived from the antigen-binding variable heavy chain regions (VHHs) of heavy chain antibodies found in camels and llamas, which lack light chains. The present disclosure encompasses VHHs that specifically bind ZnT8.

D. Variable Domain of New Antigen Receptors (VNARs)

A VNAR is a variable domain of a new antigen receptor (IgNAR). IgNARs exist in the sera of sharks as a covalently linked heavy chain homodimer. It exists as a soluble and receptor bound form consisting of a variable domain (VNAR) with differing numbers of constant domains. The VNAR is composed of a CDR1 and CDR3 and in lien of a CDR2 has HV2 and HV4 domains (see, e.g., Barelle and Porter, Antibodies, 4:240-258 (2015)). The present disclosure encompasses VNARs that specifically bind ZnT8.

E. Constant Regions

Antibodies of this disclosure can be whole antibodies or single chain Fc (scFc) and can comprise any constant region known in the art. The light chain constant region can be, for example, a kappa- or lambda-type light chain constant region, e.g., a human kappa or human lambda light chain constant region. The heavy chain constant region can be, e.g., an alpha-, delta-, epsilon-, gamma-, or mu-type heavy chain constant region, e.g., a human alpha-, human delta-, human epsilon-, human gamma- or human mu-type heavy chain constant region. In certain instances, the anti-ZnT8 antibody is an IgA antibody, an IgD antibody, an IgE antibody, an IgG1 antibody, an IgG2 antibody, an IgG3 antibody, an IgG4 antibody, or an IgM antibody.

In one embodiment, the light or heavy chain constant region is a fragment, derivative, variant, or mutein of a naturally occurring constant region. In some embodiments, the variable heavy chain of the anti-ZnT8 antibodies described herein is linked to a heavy chain constant region comprising a CH1 domain and a hinge region. In some embodiments, the variable heavy chain is linked to a heavy chain constant region comprising a CH2 domain. In some embodiments, the variable heavy chain is linked to a heavy chain constant region comprising a CR3 domain. In some embodiments, the variable heavy chain is linked to a heavy chain constant region comprising a CH2 and CH3 domain. In some embodiments, the variable heavy chain is linked to a heavy chain constant region comprising a hinge region, a CR2 and a CH3 domain. The CH1, hinge region, CH2, and/or CH3 can be from an IgG antibody (e.g., IgG1, IgG4). In certain embodiments, the variable heavy chain of an anti-ZnT8 antibody described herein is linked to a heavy chain constant region comprising a CHI domain, hinge region, and CH2 domain from IgG4 and a CH-3 domain from IgG1. In certain embodiments such a chimeric antibody may contain one or more additional mutations in the heavy chain constant region that increase the stability of the chimeric antibody. In certain embodiments, the heavy chain constant region includes substitutions that modify the properties of the antibody.

In certain embodiments, an anti-ZnT8 antibody of this disclosure is an IgG isotype antibody. In one embodiment, the antibody is IgG1. In another embodiment, the antibody is IgG2. In yet another embodiment, the antibody is IgG4. In some instances, the IgG4 antibody has one or more mutations that reduce or prevent it adopting a functionally monovalent format. For example, the hinge region of IgG4 can be mutated to make it identical in amino acid sequence to the hinge region of human IgG1 (mutation of a serine in human IgG4 hinge to a proline). In some embodiments, the antibody has a chimeric heavy chain constant region (e.g., having the CH1, hinge, and CH2 regions of IgG4 and CH3 region of IgG1).

F. Bispecific Antibodies

In certain embodiments, an anti-ZnT8 antibody of this disclosure is a bispecific antibody. Bispecific antibodies are antibodies that have binding specificities for at least two different epitopes. Exemplary bispecific antibodies may bind to two different epitopes of the ZnT8 protein. Other such antibodies may combine a ZnT8 binding site with a binding site for another protein. Bispecific antibodies can be prepared as full length antibodies or low molecular weight forms thereof (e.g., F(ab') 2 bispecific antibodies, sc(Fv)2 bispecific antibodies, diabody bispecific antibodies).

Traditional production of full length bispecific antibodies is based on the co-expression of two immunoglobulin heavy chain-light chain pairs, where the two chains have different specificities (Millstein et al., Nature, 305:537-539 (1983)). In a different approach, antibody variable domains with the desired binding specificities are fused to immunoglobulin constant domain sequences. DNAs encoding the immunoglobulin heavy chain fusions and, if desired, the immunoglobulin light chain, are inserted into separate expression vectors, and are co-transfected into a suitable host cell. This provides for greater flexibility in adjusting the proportions of the three polypeptide fragments. It is, however, possible to insert the coding sequences for two or all three polypeptide chains into a single expression vector when the expression of at least two polypeptide chains in equal ratios results in high yields.

According to another approach described in U.S. Pat. No. 5,731,168, the interface between a pair of antibody molecules can be engineered to maximize the percentage of heterodimers that are recovered from recombinant cell culture. The preferred interface comprises at least a part of the CH3 domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking methods.

The "diabody" technology provides an alternative mechanism for making bispecific antibody fragments. The fragments comprise a VH connected to a VL by a linker which is too short to allow pairing between the two domains on the same chain. Accordingly, the VH and VL domains of one fragment are forced to pair with the complementary VL and VH domains of another fragment, thereby forming two antigen-binding sites.

G. Conjugated Antibodies

The antibodies or antigen-binding fragments disclosed herein may be conjugated to various molecules including macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), human serum albumin or a fragment thereof, radioactive materials (e.g., 90Y, 131I), fluorescent substances, luminescent substances, haptens, enzymes, metal chelates, detectable labels and drugs.

In certain embodiments, an anti-ZnT8 antibody or antigen-binding fragment thereof is modified with a moiety that improves its stabilization and/or retention in circulation, e.g., In blood, serum, or other tissues, e.g., by at least 1.5, 2, 5, 10, 15, 20, 25, 30, 40, or 50 fold. For example, the anti-ZnT8 antibody or antigen-binding fragment thereof can be associated with (e.g., conjugated to) a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 Daltons (or about 1,000 to about 15,000, and 2,000 to about 12,500) can be used. For example, the anti-ZnT8 antibody or antigen-binding fragment thereof can be conjugated to a water soluble polymer, e.g., a hydrophilic polyvinyl polymer, e.g., polyvinylalcohol or polyvinylpyrrolidone. Examples of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene; polymethacrylates; carbomers; and branched or unbranched polysaccharides.

The above-described conjugated antibodies or fragments can be prepared by performing chemical modifications on the antibodies or the lower molecular weight forms thereof described herein Methods for modifying antibodies are well known in the art.

III. Affinity Maturation

In one embodiment, an anti-ZnT8 antibody or antigen-binding fragment thereof is modified, e.g., by mutagenesis, to provide a pool of modified antibodies. The modified antibodies are then evaluated to identify one or more antibodies having altered functional properties (e.g., improved binding, improved stability, reduced antigenicity or increased stability in vivo). In one implementation, display library technology is used to select or screen the pool of modified antibodies. Higher affinity antibodies are then identified from the second library, e.g., by using higher stringency or more competitive binding and washing conditions. Other screening techniques can also be used. Methods of effecting affinity maturation include random mutagenesis (e.g., Fukuda et al., Nucleic Acids Res. 34:e127 (2006); targeted mutagenesis (e.g., Rajpal et al., Proc. Natl. Acad. Sci. USA, 102:8466-71 (2005); shuffling approaches (e.g., Jermutus et al., Proc. Natl. Acad. Sci. USA, 98:75-80 (2001); and in silica approaches (e.g., Lippow et al., Nat. Biotechnol., 25: 1171-6 (2005).

In some embodiments, the mutagenesis is targeted to regions known or likely to be at the binding interface. If, for example, the identified binding proteins are antibodies, then mutagenesis can be directed to the CDR regions of the heavy or light chains as described herein. Further, mutagenesis can be directed to framework regions near or adjacent to the CDRs, e.g., framework regions, particularly within 10, 5, or 3 amino acids of a CDR junction. In the case of antibodies, mutagenesis can also be limited to one or a few of the CDRs, e.g., to make step-wise improvements.

In one embodiment, mutagenesis is used to make an antibody more similar to one or more germline sequences. One exemplary germlining method can include: identifying one or more germline sequences that are similar (e.g., most similar in a particular database) to the sequence of the isolated antibody. Then mutations (at the amino acid level) can be made in the isolated antibody, either incrementally, in combination, or both. For example, a nucleic acid library that includes sequences encoding some or all possible germline mutations is made. The mutated antibodies are then evaluated, e.g., to identify an antibody that has one or more additional germline residues relative to the isolated antibody and that is still useful (e.g., has a functional activity). In one embodiment, as many germline residues are introduced into an isolated antibody as possible.

In one embodiment, mutagenesis is used to substitute or insert one or more germline residues into a CDR region. For example, the germline CDR residue can be from a germline sequence that is similar (e.g., most similar) to the variable region being modified. After mutagenesis, activity (e.g., binding or other functional activity) of the antibody can be evaluated to determine if the germline residue or residues are tolerated. Similar mutagenesis can be performed in the framework regions.

Selecting a germline sequence can be performed in different ways. For example, a germline sequence can be selected if it meets a predetermined criterion for selectivity or similarity, e.g., at least a certain percentage identity, e.g., at least 75, 80, 85, 90, 91, 92, 93, 94, 95, 96, 97, 98, 99, or 99.5% identity, relative to the donor non-human antibody. The selection can be performed using at least 2, 3, 5, or 10 germline sequences. In the case of CDR1 and CDR2, identifying a similar germline sequence can include selecting one such sequence. In the case of CDR3, identifying a similar germline sequence can include selecting one such sequence, but may include using two germline sequences that separately contribute to the amino-terminal portion and the carboxy-terminal portion. In other implementations, more than one or two germline sequences are used, e.g., to form a consensus sequence.

Calculations of "sequence identity" between two sequences are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frameshift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

In other embodiments, the antibody may be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies may be accomplished by altering the amino acid sequence to contain glycosylation site consensus sequences; such techniques are well known in the art Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) CRC Crit. Rev. Biochem. 22:259-306. Removal of any carbohydrate moieties present on the antibodies may be accomplished chemically or enzymatically as described in the art (Hakimnuddin et al. (1987) Arch. Biochem. Biophys., 259: 52; Edge et al. (1981) Anal. Biochem., 118:131; and Thotakura et al. (1987) Meth. Enzymol., 138:350). See, e.g., U.S. Pat. No. 5,869,046 for a modification that increases in vivo half-life by providing a salvage receptor binding epitope.

In one embodiment, an anti-ZnT8 antibody has one or more CDR sequences (e.g., a Chothia, an enhanced Chothia, or Kabat CDR) that differ from those described herein. In one embodiment, an anti-ZnT8 antibody has one or more CDR sequences include amino acid changes, such as substitutions of 1, 2, 3, or 4 amino acids if a CDR is 5-7 amino acids in length, or substitutions of 1, 2, 3, 4, or 5, of amino acids in the sequence of a CDR if a CDR is 8 amino acids or greater in length. The amino acid that is substituted can have similar charge, hydrophobicity, or stereochemical characteristics. In some embodiments, the amino acid substitution(s) is a conservative substitution. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). In other embodiments, the amino acid substitution(s) is a non-conservative substitution. The antibody or antibody fragments thereof that contain the substituted CDRs can be screened to identify antibodies of interest.

Unlike in CDRs, more substantial changes in structure framework regions (FRs) can be made without adversely affecting the binding properties of an antibody. Changes to FRs include, but are not limited to, humanizing a nonhuman-derived framework or engineering certain framework residues that are important for antigen contact or for stabilizing the binding site, e.g., changing the class or subclass of the constant region, changing specific amino acid residues which might alter an effector function such as Fc receptor binding (Lund et al., J Immun., 147:26S7-62 (1991); Morgan et al., Immunology, 86:319-24 (199S)), or changing the species from which the constant region is derived.

IV. Methods of Producing Anti-ZnT8 Antibodies

The anti-ZnT8 antibodies (or antigen-binding domain(s) of an antibody or functional fragment thereof) of this disclosure may be produced, for example, in bacterial or eukaryotic cells. To produce the polypeptide of interest, a polynucleotide encoding the polypeptide is constructed, introduced into an expression vector, and then expressed in suitable host cells. Standard molecular biology techniques are used to prepare the recombinant expression vector, transfect the host cells, select for transformants, culture the host cells and recover the antibody.

If the antibody is to be expressed in bacterial cells (e.g., E. coli), the expression vector should have characteristics that permit amplification of the vector in the bacterial cells. Additionally, when E. coli such as JM109, DH5a, HB1O1, or XL I-Blue is used as a host, the vector must have a promoter, for example, a lacZ promoter (Ward et al., 341: 544-546 (1989), araB promoter (Better et al., Science, 240: 1041-1043 (1988)), or T7 promoter that can allow efficient expression in E. coli. Examples of such vectors include, for example, M13-series vectors, pUC-series vectors, pBR322, pBluescript, pCR-Script, pGEX-5X-1 (Pharmacia), "QIA-express system" (QIAGEN), pEGFP, and pET (when this expression vector is used, the host is preferably BL21 expressing T7 RNA polymerase). The expression vector may contain a signal sequence for antibody secretion. For production into the periplasm of E. coli, the pelB signal sequence (Lei et al., J. Bacteriol., 169:4379 (1987)) may be used as the signal sequence for antibody secretion. For bacterial expression, calcium chloride methods or electroporation methods may be used to introduce the expression vector into the bacterial cell.

If the antibody is to be expressed in animal cells such as CHO, COS, 293, 293T, and NIH3T3 cells, the expression vector includes a promoter necessary for expression in these cells, for example, an SV40 promoter (Mulligan et al., Nature, 277:108 (1979)), MMLV-LTR promoter, EF1a promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, the antibodies are produced in mammalian cells. Exemplary mammalian host cells for expressing a polypeptide include Chinese Hamster Ovary (CHO cells) (including dhfr-CHO cells, described in Urlaub and Chasm (1980) Proc. Natl. Acad. Sci. USA 77:4216-4220, used with a DHFR selectable marker, e.g., as described in Kaufman and Sharp (1982) Mol. Biol. 159:601 621), human embryonic kidney 293 cells (e.g, 293, 293E, 293T) COS cells, NIH3T3 cells, lymphocytic cell lines, e.g., NSO myeloma cells and SP2 cells, and a cell from a transgenic animal, e.g., a transgenic mammal. For example, the cell is a mammary epithelial cell.

The antibodies of the present disclosure can be isolated from inside or outside (such as medium) of the host cell and purified as substantially pure and homogenous antibodies. Methods for isolation and purification commonly used for polypeptides may be used for the isolation and purification of antibodies described herein, and are not limited to any particular method. Antibodies may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column, Examples of columns using protein A column include Hyper D, POROS, and Sepharose FF (GE Healthcare Biosciences). The present disclosure also includes antibodies that are highly purified using these purification methods.

The present disclosure also provides a nucleic acid molecule or a set of nucleic acid molecules encoding an anti-ZnT8 antibody or antigen-binding molecule thereof disclosed herein. In one embodiment, the invention includes a nucleic acid molecule encoding a polypeptide chain, which comprises a light chain of an anti-ZnT8 antibody or antigen-binding molecule thereof as described herein. In one embodiment, the invention includes a nucleic acid molecule encoding a polypeptide chain, which comprises a heavy chain of an anti-ZnT8 antibody or antigen-binding molecule thereof as described herein.

Also provided are a vector or a set of vectors comprising such nucleic acid molecule or the set of the nucleic acid molecules or a complement thereof, as well as a host cell comprising the vector.

The instant disclosure also provides a method for producing a ZnT8 or antigen-binding molecule thereof or chimeric molecule disclosed herein, such method comprising culturing the host cell disclosed herein and recovering the antibody, antigen-binding molecule thereof, or the chimeric molecule from the culture medium.

A variety of methods are available for recombinantly producing a ZnT8 antibody or antigen-binding molecule thereof disclosed herein, or a chimeric molecule disclosed herein. It will be understood that because of the degeneracy of the code, a variety of nucleic acid sequences will encode the amino acid sequence of the polypeptide. The desired polynucleotide can be produced by de novo solid-phase DNA synthesis or by PCR mutagenesis of an earlier prepared polynucleotide.

For recombinant production, a polynucleotide sequence encoding a polypeptide (e.g., a ZnT8 antibody or antigen-binding molecule thereof disclosed herein, or any of the chimeric molecules disclosed herein) is inserted into an appropriate expression vehicle, i.e., a vector which contains the necessary elements for the transcription and translation of the inserted coding sequence, or in the case of an RNA viral vector, the necessary elements for replication and translation.

The nucleic acid encoding the polypeptide (e.g., a ZnT8 antibody or antigen-binding molecule thereof disclosed herein, or any of the chimeric molecules disclosed herein) is inserted into the vector in proper reading frame. The expression vector is then transfected into a suitable target cell which will express the polypeptide. Transfection techniques known in the art include, but are not limited to, calcium phosphate precipitation (Wigler et al. 1978, Cell 14:725) and electroporation (Neumann et al. 1982, EMBO J. 1:841). A variety of host-expression vector systems can be utilized to express the polypeptides described herein (e.g., a ZnT8 antibody or antigen-binding molecule thereof disclosed herein, or any of the chimeric molecules disclosed herein) in eukaryotic cells. In one embodiment, the eukaryotic cell is an animal cell, including mammalian cells (e.g., 293 cells, PerC6, CHO, BHK, Cos, HeLa cells). When the polypeptide is expressed in a eukaryotic cell, the DNA encoding the polypeptide (e.g., a ZnT8 antibody or antigen-binding molecule thereof disclosed herein, or any of the chimeric molecules disclosed herein) can also code for a signal sequence that will permit the poly peptide to be secreted. One skilled in the art will understand that while the poly peptide is translated, the signal sequence is cleaved by the cell to form the mature chimeric molecule. Various signal sequences are known in the art and familiar to the skilled practitioner. Alternatively, where a signal sequence is not included, the poly peptide (e.g., a ZnT8 antibody or antigen-binding molecule thereof disclosed herein, or any of the chimeric molecules disclosed herein) can be recovered by lysing the cells.

V. Small Molecule Modulators of ZnT8

In one aspect, the methods of the present invention can be used to identify a ZnT8 modulator. In particular embodiments, the ZnT8 modulator is a small molecule. The term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

Nevertheless, compound libraries may be screened for ZnT8 modulators. A compound library is a mixture or collection of one or more putative modulators generated or obtained in any manner. Any type of molecule that is capable of interacting, binding or has affinity for ZnT8 may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as "small molecule" organic compounds generated, for example, using combinatorial chemistry techniques; and mixtures thereof.

A library typically contains more than one putative modulator or member, i.e., a plurality of members or putative modulators. In certain embodiments, a compound library may comprise less than about 50,000, 25,000, 20,000, 15,000, 10000, 5000, 1000, 500 or 100 putative modulators, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to 2000, 300 to 3000, 300 to 5000, 300 to 6000, 300 to 10,000, 500 to about 1000, 500 to about 2000, 500 to about 3000, 500 to about 5000, 500 to about 6000, or 500 to about 10,000 putative modulators. In particular embodiments, a compound library may comprise less than about 50,000, 25,000, 20,000, 15,000, 10,000, 5,000, 1000, or 500 putative modulators.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401, Lebl et al., Biopolymers 1995, 37 177-198; and references cited therein. Compound libraries may also be obtained from commercial sources including, for example, from Maybridge, ChemNavigator.com, Timtec Corporation, ChemBridge Corporation. A-Syntese-Biotech ApS, Akos-SC, G & J Research Chemicals Ltd., Life Chemicals, Interchim S.A., and Spectrum Info. Ltd.

VI. Screening for Modulators of ZnT8

The compositions and methods can be used to screen for modulators of ZnT8 using an anti-ZnT8 antibody or antigen-binding fragment thereof and human pancreatic beta cells. The assay can be used to identify agonists or antagonists of ZnT8. In certain embodiments, inhibitors of ZnT8 that mimic the naturally occurring LOF mutations to prevent type-2 diabetes in humans can be identified. In particular embodiments, compounds that decrease ZnT8 amount following cytokine stress can be identified. In other embodiments, compounds that rescue ZnT8 degradation following cytokine stress can be identified.

Accordingly, in one embodiment, a method comprises the steps of (a) permeabilizing human beta cells present in a substrate; (b) contacting the cells with a test agent; and (c) measuring the amount of zinc transporter 8 (ZnT8) using at least one anti-ZnT8 antibody or antigen-binding fragment thereof.

In another embodiment, a method of identifying a modulator of ZnT8 comprises the steps of (a) contacting human beta cells with a test agent; and (b) detecting a change in the amount of ZnT8 in the cell as compared to the amount of ZnT8 in a cell not contacted with the test agent, wherein the detecting step utilizes at least one anti-ZnT8 antibody or antigen-binding fragment thereof.

In a further embodiment, a method of identifying a modulator of ZnT8 comprising the steps of (a) contacting human beta cells with a metabolic or cytokine stressor; (b) contacting the cells with a test agent; and detecting a change in the amount of ZnT8 in the cell as compared to the amount of ZnT8 in a cell contacted with the stressor but not contacted with the test agent, wherein the detecting step utilizes at least one anti-ZnT8 antibody or antigen-binding fragment thereof. In particular embodiments, the metabolic stressor comprises glucose and palmitic acid. In other embodiments, the cytokine stressor comprises one or more of IL-1β, TNF-α, IFN-γ, and IL-17. In any of the foregoing embodiments, the measuring or detecting step comprises a proximity ligation assay.

In particular embodiments, a human pancreatic beta-cell line is used. In certain embodiments, a human pancreatic beta-cell line that exhibits GSIS is used. In one embodiment, a human pancreatic beta-cell line that displays functional characteristics of bona fide beta cells is used. In other embodiments, a human pancreatic beta cell that is a diabetes model is used. In a specific embodiment, the cell line is EndoC-βH1. Other cell lines include, but are not limited to, EndoC-BH2 and EndoC-BH3. Further cell lines include 1.1B4, 1.4E7 and 1.1E7.

In other embodiments primary human islets are used. In a further embodiment, human pseudoislets are used. In still further embodiments, a hPSC-based model is used. For example Cellartis® hiPS beta cells can be used (Takara Bio USA, Inc., Catalog No. Y0106 (Mountain View, CA)).

VII. Kits

The compositions of the present invention can be provided in a kit. In one embodiment, a kit comprises an antibody described herein.

In addition to the anti-ZnT8 antibody or fragment thereof; the kit can include other ingredients, such as a solvent or buffer, a stabilizer, or a preservative, performing the assay. The anti-ZnT8 antibody or fragment thereof can be provided in any form, e.g., liquid, dried or lyophilized form, preferably substantially pure and/or sterile. When the agents are provided in a liquid solution, the liquid solution preferably is an aqueous solution. When the anti-ZnT8 antibody or fragment thereof is provided as a lyophilized product, the lyophilized powder is generally reconstituted by the addition of a suitable solvent. The solvent, e.g., sterile water or buffer (e.g., PBS), can optionally be provided in the kit.

The kit can further comprise human beta cells for performing the modulator screen. Such cells can comprise a cell line including, but not limited to, EndoC-βH1, EndoC-βH2, EndoC-βH3, 1.1B4, 1.4E7, 1.1E7. Alternatively, the kit can comprise hPSCs for differentiation into beta cells. The kit can further comprise control cells including, but not limited to, INS-1E and HEK293 cells. The kit can also comprise ingredients necessary for preparing the cells for detection using an anti-ZnT8 antibody or antigen-binding fragment thereof including, but not limited to, fixation, permeabilization and blocking. Such ingredients can include, but are not limited to, buffers/solutions comprising paraformaldehyde and/or sodium azide.

In other embodiments, the kit comprises reagents and ingredients for detecting ZnT8 in the beta cells. In a specific embodiment, the kit comprises secondary antibodies and a detection scheme such as HRP or chemiluminescence. In another embodiment, the kit comprises reagents and ingredients for a proximity ligation assay.

In a further embodiment, a kit comprises a substrate for performing a modulator screen. In certain embodiments, the solid substrate comprises a silicon wafer, glass, metal, plastic, ceramic, metal alloy, polymer or any combinations thereof. In a particular embodiment, the solid substrate comprises a plate. In a more particular embodiment, the plate is a 96-well plate from, for example. Meso Scale Diagnostics, LLC (Rockville, MD). The kit can comprises a substrate useful for high-throughput screening.

The kit can include one or more containers for the composition or compositions containing the agents. In some embodiments, the kit contains separate containers, dividers or compartments for the components and for any informational material. For example, the components can be contained in a bottle, vial, or tube, and the informational material can be contained in a plastic sleeve or packet. In other embodiments, the separate elements of the kit are contained within a single, undivided container. For example, a component can be contained in a bottle, vial or tube that has attached thereto the informational material in the form of a label. The containers of the kits can be air tight, waterproof (e.g., impermeable to changes in moisture or evaporation), and/or light-tight (e.g., in the case of an ECL label).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

EXAMPLE 1: Downregulation of the Islet-Specific Zinc Transporter-8 (ZnT8) Protects Human Insulinoma Cells Against Inflammatory Stress. ZnT8 has a primary function as a zinc sequestrating transporter in the insulin secretory granules (ISGs) of pancreatic β-cells. Loss-of-function mutations in ZnT8 are associated with protection against type-2 diabetes (T2D), but the protective mechanism is unclear. As described herein, the present inventors developed an in-cell ZnT assay to track endogenous ZnT8 responses to metabolic and inflammatory stress applied to human insulinoma EndoC-βH1 cells. Unexpectedly, high glucose and free fatty acid (FFA) did not alter the cellular ZnT8 level, but proinflammatory cytokines induced an acute, reversible and graded ZnT8 downregulation. Approximately 50% of the cellular ZnT8 were localized to the endoplasmic reticulum (ER) as the primary target of cytokine insult. Transcriptome profiling of cytokine exposure revealed an adaptive unfolded protein response (UPR) with a marked immunoproteasome activation that degraded ZnT8 and insulin in a highly coordinated manner over a 1000-fold cytokine concentration range. ZnT8 knockdown by RNA interference protected cells against cytokine cytotoxicity, suggesting a protective mechanism by which decongesting the ER burden of ZnT8 protects β-cells from proapoptotic UPR in the face of chronic low-grade inflammation.

INTRODUCTION

Pancreatic β-cells dedicate up to 50% of biosynthetic capacity to insulin production upon glucose stimulation (1). The synthesized insulins are complexed with zinc to form solid zinc-insulin crystals for storage in insulin secretory granules (ISGs), giving rise to one of the highest quantities of cellular zinc in the human body (2,3). The granular zinc is secreted along with insulin and then recycled back into β-cells during iterative cycles of insulin secretion and restocking. This dynamic process demands tight controls over zinc transport to achieve coordinated zinc mobilization while maintaining the cytosolic free zinc concentration around a homeostatic setpoint (4). Among all the zinc transporters in β-cells (5,6), ZnT8 is unique in its islet-specific expression (7,8), and its high abundance as a major autoantigen involved in autoimmunity of type-1 diabetes (T1D) (9,10). Human genetics revealed that a hyperactive ZnT8 polymorphic variant encoded by SLC30A gene was associated with increased T2D risk (11) whereas truncating mutations in SLC3A8 were found to be protective against T2D in heterozygous human carriers (12). The emerging evidence supports a causality linking ZnT8 downregulation and reduced T2D risk, but the protective mechanism of ZnT8 downregulation is unclear.

The onset of T2D and its progression are largely determined by a progressive failure of β-cells to produce sufficient amounts of insulin to compensate for insulin resistance. Multiple ZnT8 null mouse models showed a consistent decrease of ISG zinc content (13-17), but variable phenotypic changes in glucose-stimulated insulin secretion (GSIS) (18). Apparently, the transport activity of ZnT8 is not closely associated with GSIS, raising the possibility that novel aspects of ZnT8 cell biology may regulate f-cell resilience to stress-induced failure. A major stress factor for T2D is the deleterious consequences of overnutrition (19) Chronic exposures to high levels of glucose and FFA impair insulin secretion, induce β-cell death and promote insulin resistance (20,21). A combination of elevated glucose and FFA has a potentiating effect known as glucolipotoxicity (22). Excessive levels of glucose and FFA can also induce local production and release of cytokines and chemokines from pancreatic islets, leading to macrophage recruitment and islet inflammation characterized by increased expression of inflammatory cytokines derived from innate immune cells (23). This local inflammation is exacerbated by circulating cytokines released from nutrient-stressed adipose tissues (24-26). Moreover, β-cells under metabolic and inflammatory stresses overproduce hydroxyl radicals (*OH) and nitroxide (NO) by mitochondrial oxidation and inducible nitric oxide synthase, respectively (27,28). Zinc is an essential co-factor for enzymes involved in the proper functioning of the antioxidant defense system (29). Perturbation of zinc homeostasis could intensify oxidative stress and cell damage (30). At the cellular level, metabolic, inflammatory and zinc stress converge to activate UPR that could either allow cells to survive by adapting to stress or kill cells through apoptosis (31). Characterizing stress-induced ZnT8 responses in adaptive unfolded protein response (UPR) may illuminate how ZnT8 influences the UPR decision on μ-cell fate, thereby informing on the protective mechanism of ZnT8 downregulation.

A major challenge to track adaptive UPR is the lack of a detectable change in cell viability. In the present example, the present inventors stress-induced fluctuations of the endogenous ZnT8 level as a phenotypic readout. Toward this end, the present inventors generated an anti-ZnT8 monoclonal antibody (mAb20) with superb specificity for in-cell ZnT8 immunodetection over a low background of non-specific bindings to other ZnT paralogs and high-abundant cellular proteins in EndoC-βH1 cells (32). Built on mAb2.0, an in-cell enzyme-linked immunosorbent assay (ELISA) w as developed to quantify fluctuations of the endogenous ZnT8 level in a multifactorial space of glucose (Glc), FFA, zinc, proinflammatory cytokines and their time- and dose-dependent profiles. This precise assay revealed a highly sensitive ZnT8 response to cytokine stimulations. Further analysis revealed a pleiotropic role of ZnT8 in ER where ZnT8 and insulin were selectively targeted as two major μ-cell autoantigens for immunoproteasome-mediated degradation. Hence, our experiments revealed a novel immunologic process of decongesting two major ER burdens to protect β-cells from proapoptotic UPR.

Materials and Methods

Antibody reagents. mAb20 was validated as described previously (33). Antibody conjugated dynabeads for biomagnetic separations were prepared using N-hydroxylsuccinimide (NHS) functionalized polyethylene glycol NHS-PEG5K-NTS (Nanocs, Cat. #PG2-NS-5k) to crosslink antibodies with surface reactive amine groups on 2.8-μm hydrophilic M-270 Amine-Dynabeads (Invitrogen, Cat. #14307D). A 50 molar excess of NHS-PEG5K-NHS over the surface primary amine groups was used for bead activation and 5 molar excess of mAb20, mouse-IgG or anti-BAP31 polyclonal antibodies (Proteintech, Cat. #11200-1-AP) yielded an antibody surface coating density of ~100 μg antibody per ml beads.

Cell cultures. EndoC-βH1 cells from Univercell-Biosolutions had a doubling time of approximately 7-10 days. Cells (passage between 40-60) were detached from culture flasks using 0.05% trypsin and 0.53 mM EDTA, and then reseeded at 75,000 cells/well at 70% confluence in a 96-well TPP plate (Sigma Cat. #Z707902) coated with Matrigel-fibronectin matrix as described (78). The cells were subcultured at 37° C. in a 5% CO2 humidified atmosphere, and grown in a serum-free culture medium containing 11 mM glucose Dulbecco's modified Eagle's medium (ThermoFisher Scientific, Cat. #11885076), 2% BSA faction V (Sigma, Cat. #10735078001), 10 mM nicotinamide (Sigma, Cat. #47865-U), 50 μM 2-mercaptoethanol (ThermoFisher Scientific, Cat. #21985-023), 5.5 μg/ml transferrin (Sigma, Cat. #T8158-100 mg), 6.7 ng/ml sodium selenite (Sigma, Cat. #S5261-25g), 100 U/ml Penicillin and 100 μg/ml streptomycin (ThermoFisher Scientific, Cat. #15140122). Flp-In, T-Rex-HEK293 cells with or without doxycycline-induced ZnT8 overexpression were generated and cultured as described preciously (34).

Stressor exposures. PA-BSA conjugation was prepared by adding PA powder to a final concentration of 8 mM in 1.6 mM FFA-free BSA (Sigma, Cat. #A7030-50G) pre-dissolved in 135 mM NaCl, 3.6 mM KCl, 0.5 mM MgCl2, and 10 mM HEPES (pH 7.4). The mixture was incubated with gentle stir at 37° C. and then filter-sterilized and stored at 4° C. as described previously (79). When added to the cell culture, the PA-BSA mixture was diluted 13.3-fold with supplement of glucose to make a 1× Glc+PA solution containing 0.6 mM PA and 48 mM Glc. A cytokine cocktail was prepared before each experiment by mixing individual stock solutions of IL-1β, IFN-γ, IL-17, TNF-β at respective concentrations used previously on human islets and EndoC-PHI cells (37). 1× cytokine cocktail in the culture medium contained 5 ng/ml IL-1β, 10 ng/ml TNF-α, 50 ng/ml IFN-γ and 100 ng/ml IL-17 All cytokines were provided by R&D Systems (Minneapolis, MN, USA). The subcultured EndoC-βH1 cells were allowed to adhere for 24 hr prior to addition of experimental media containing Glc+PA, zinc or cytokine cocktail in serial dilutions with eight replicates. After a designated exposure period, the endogenous ZnT8 level in each well was analyzed along with stress-induced cytotoxicity, GSIS and cellular insulin content. For cytokine withdrawal experiments, cells were first exposed to 1× cytokine for 24 hr, and then cultured in the cytokine-free culture medium for different recovery periods before analysis.

In-cell ELISAs. EndoC-βH1 cells in a 96-well plate with or without stressor exposures were fixed in 50 μl/well Flow Cytometry Fixation Buffer (R&D Systems, Cat. #FC004), and then permeabilized in Permeabilization/Wash Buffer I (R&D Systems, Cat. #FC005) for 1 hr with 2.5% BSA as a blocking reagent. Next, mAb20 or a rabbit anti-HLA-1 antibody (Proteintech, Cat. #15240-1-AP) was 1:600 or 1:60 diluted to Permeabilization/Wash Buffer I plus 0.5% BSA. Cells in each well were incubated with the diluted antibody solution for 2 hr at 37° C., washed once, and then exposed to a HRP-conjugated anti-mouse IgG (H+L) (Invitrogen, Cat. #62-6520) or anti-rabbit IgG (H+L) antibody (Invitrogen. Cat. #62-6120) in a 1:3000 dilution in Permeabilization/Wash Buffer I plus 0.1% BSA. After 1 hr incubation with the secondary antibody at RT, cells were washed three times to remove unbound antibodies before adding SuperSignal ELISA Femto Substrate (ThermoFisher Scientific, Cat. #37075). The HRP reaction was terminated at 5 min by transferring the reaction mixture to a 96-well opaque microplate for chemiluminescence quantification on a FlexStation-3 multi-mode microplate reader.

Cytotoxicity Assay. Cell culture and experiments were performed in a 96-well plate in culture media without phenol red (Sigma, Cat. #D4947). Cytotoxicity in cell culture after experimental manipulation was continuously monitored based on the change in the fluorescence intensity of CellTox Green Dye (Promega, Cat. #G8741) that preferentially stained dead cells with a loss of membrane integrity. The dye was 1:1000 diluted in the culture medium and delivered directly to cells at the same time of dose titrations of Glc+PA, zinc and cytokines. CellTox fluorescence signals were recorded on a FlexStation-3 multi-mode microplate reader with eight replicates at 0, 1, 2, 4, 6, 8, 20, 24, 30, and 48 hr following dye and stressor additions. Viable cells in the control cell culture medium produced no appreciable increases in CellTox fluorescence due to an excellent tolerance of EndoC-βH1 cells to the dye. At the end of experiment, all cells were lysed by adding detergent (DDM) to 0.1% in each well, and the maximum CellTox fluorescence intensity was recoded and used for normalization of the CellTox fluorescence intensity.

Immunoblotting. Cells in a 96-well plate were directly resuspended in 50 μl/well 1× Laemmli Sample Buffer (Bio-Rad cat. #1610737). An aliquot of 15 μl SDS-lysate was loaded onto a precast protein gel for SDS-PAGE and subsequent immunoblotting using the following antibodies directed to ZnT8 (mAb20), tubulin (Invitrogen, Cat. #MA1-83256), calnexin (Proteintech, Cat. #10427-2-AP), BAP31 (Proteintech, Cat. #11200-1-AP), IA2 (Proteintech, Cat. #10584-1-AP), TMED3 (Proteintech, Cat. #21902-1-AP), VAMP2 (Proteintech, Cat. #10135-1-AP), Golgin97 (Proteintech, Cat. #12640-1-AP) and HLA-I (Proteintech, Cat. #15240-1-AP). Protein band intensity was measured using ImageJ, and the numerical value for each stressor-treated protein sample was normalized to the untreated sample on the same immunoblot.

Immunofluorescence staining, imaging and colocalization analysis. EndoC-βH1 cells were grown on coverslips at 50% confluence, fixed (R&D Systems, cat. #FC004), permeabilized (R&D Systems, cat. #FC005) and co-stained with mAb20 at a 1:600 dilution from a 1 mg/ml mAb stock with one of the following antibodies at a 1:50 dilution:anti-insulin antibody APC conjugated (R&D Systems, Cat. #IC1417A), rabbit anti-BAP31, IA2, TMED3, VAMP2 and Golgin97 as described above. Secondary anti-mouse IgG (H+L) conjugated with Alexa Fluor 594 (Invitrogen, Cat. #A11032, dilution 1:1000), anti-rabbit IgG (H+L) conjugated with Alexa Fluor 647 (Life Technologies, Cat. #A21244, dilution 1:1000) and DAPI were used for fluorescence imaging on a Zeiss LSM 700 inverted confocal microscope with a 63× oil objective. ImageJ with an intensity correlation analysis plugin was used to quantify colocalization of ZnT8 IF (red channel) and an ER or ISG marker IF (green channel) (80). Confocal images were split into red and green channels without background corrections. ROIs were selected for ER or ISG regions where all pixels above an auto-threshold were used to calculate Manders' split coefficients (MSC) for red to green channel.

Liposome preparation. EndoC-βH1 cells at 90% confluence from a 10-cm culture disk with or without 1× cytokine pre-exposure were scraped and resuspended in 25 ml assay buffer (100 NaCl, 20 mM HEPES, pH 7.0) supplemented with a cOmplete mini EDTA-free protease cocktail tablet (Sigma). Cells in suspension were fragmented by 20 passages through a high-shear fluid processor at 120 psi (Microfluidics). The resultant membrane vesicles were collected by ultracentrifugation at 258,000×g for 60 min. mAb20 immunoblotting analysis indicated that all cellular ZnT8 was recovered in the pellet. The membrane pellet was then homogenized in 0.5 ml assay buffer and sonicated in an ice-chilled cup-horn sonicator until vesicle turbidity disappeared completely, indicating the formation of small unilamellar vesicles (SUVs) with diameters around 100 nm (81). Quantification of total protein amounts in SUVs indicated no significant difference with and without cytokine exposure.

Co-immunoprecipitation. The binding capacity of mAb20-PEG5K-Dynabeads or anti-BAP31-PEG5K-Dynabeads was first determined by dose titrations of SUVs to estimate the saturating SUV concentration for a given amount of antibody-conjugated bead based on mAb20 or anti-BAP31 immunoblotting analysis of SUVs eluted from the beads. 1.2-fold excess of beads were used for all experiments to ensure a ~50% depletion of ZnT8-containing SUVs and a >95% depletion of BAP31-containing SUVs by respective affinity beads. The co-immunoprecipitation experiments were performed by incubating an aliquot of SUVs and antibody-conjugated beads at RT for 2 hr with 0.5% BSA as a blocking reagent. The unbound SUVs remained in the flow-through while bound SUVs were washed three times with assay buffer plus 0.1% BSA, and then SDS-eluted by 1× Laemmli Sample Buffer. The amounts of ZnT8 in total SUVs, flow-through, and bead-elution were analysis by mAb20 immunoblotting, quantified by ImageJ as described above.

GSIS and insulin quantification. EndoC-βH1 cells with dose titrations of Glc+PA, zinc or cytokines cocktail in a 96-well plate were switched to a Krebs buffer (Alfa Aesar, cat. #J67795). After cell starvation in Krebs buffer for 1 h, EndoC-βH1 cells were replaced with fresh Krebs buffer containing 20 mM glucose plus 45 µM IBMX. After 45 min, the Krebs buffer was collected for measurement of secreted insulin. Cells were then lysed by 100 µl/well Krebs buffer with 1% DDM. Total insulin content was measured in 100-fold diluted cell lysate, A homogeneous time resolved fluorescence (HTRF) based ultra-sensitive insulin kit (Cisbio, cat. #62IN2PEG) was used to detect both secreted and total insulin as described previously (60).

RNAseq. mRNA profiles of EndoC-βH1 cells with or without 1× cytokines exposure for 24 h were generated by deep sequencing using Illumina HiSeq2500. Cells were collected, washed by PBS and lysed for total RNA extraction using RNeasy Mini Kit (QIAGEN, Cat. #74104). NEBNext Poly(A) Magnetic Isolation Module (NEB cat. #E7490) and NEBNext Ultra II Directional RNA Library Prep Kit for Illumina (Cat. #E7765) were used to generate libraries. The BioAnalyzer was used for quality control of the libraries to ensure adequate concentration and appropriate fragment size. The resulting library insert size was 200-500 bp with a median size around 300 bp, Libraries were uniquely barcoded and pooled for sequencing. Reads were demultiplexed using Illumina's bcl2fastq2. Read quality was checked for each sample using FastQC v0.10.1, and then imported into STAR version 2.5.2b for alignment into BAM files. The aligned reads were assembled with CLASS v.2.1.7, for each sample to create transcript models (transfrags). The resulted gtf files were fed to Stringtie-merge (v1.3.6) to create a non-redundant set of transcripts which was used in a later analysis of differential expression. Cuffdiff v2.2.1 was run on each sample to obtain FPKM values found in the FPKM-_matrix.xlsx file. Both Cuffdiff and DESeq were used to look for significant changes in transcript expression. DESeq output was split in 2 files, containing the transfrags that were annotated (DESeq_results_gn.csv) and the ones that could not be assigned to a known gene (DESeq_results_no_gn.csv). Cuffdiff_*_exp.diff.txt files were generated with Cuffdiff. These tab delimited files contain the feature_id, gene name, locus, sample names, test_status, FPKM values for each gene or transcript in both samples, the log fold change FPKMy/FPKMx, value of test statistics used to compute significance of the observed change in FPKM, p-value and q-values. FPKM values and the standard deviations per sample were summarized in FPKM_matrix.xlsx. The RNAseq data are available under an accession number of GSE134122 from Gene Expression Omnibus (GEO) of National Center for Biotechnology Information.

SLC30A8 knockdown. To perform gene silencing by RNA interference, a master mix of Opti-MEM reduced serum-free medium (Gibco, cat. #31985-062) was pre-mixed with 0.4% RNAiMAX transfection reagent (Invitrogen, cat. #13778-100) and 75 nM ZnT8 targeting or scrambled siRNA (OriGene cat. #SR325944). The solution was then incubated at room temperature for 10 min to form siRNA-lipid complexes before 50 µl of the master mix was added to each well in a 96-well plate. Cells resuspended in standard culturing media were added in a 1:1 volume to give $7 \times 10^4$ cells per well. After 24 h, the transfection media were replaced with complete culturing media. After additional 2 days, cells were exposed to 1× cytokine cocktail, followed by immunoblotting and cytotoxicity analysis as described above.

Results

Figure 1B:
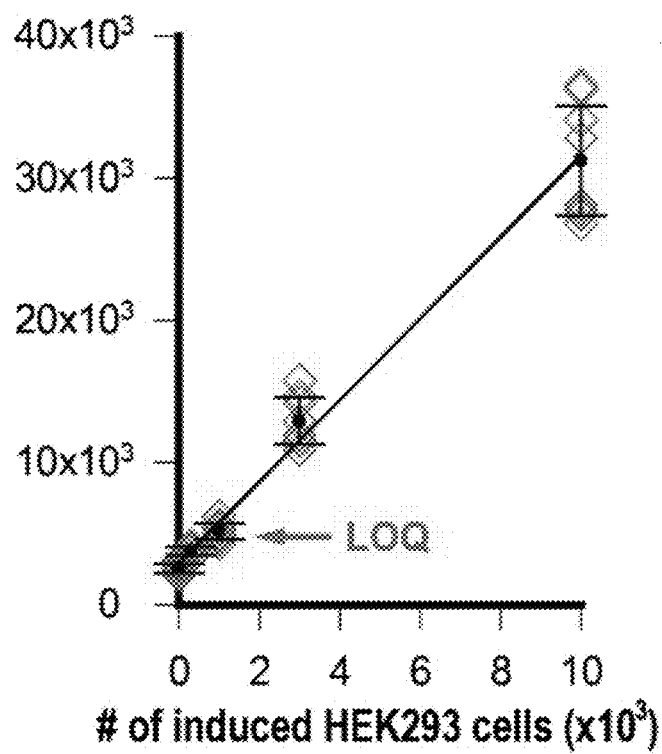
Figure 1C:
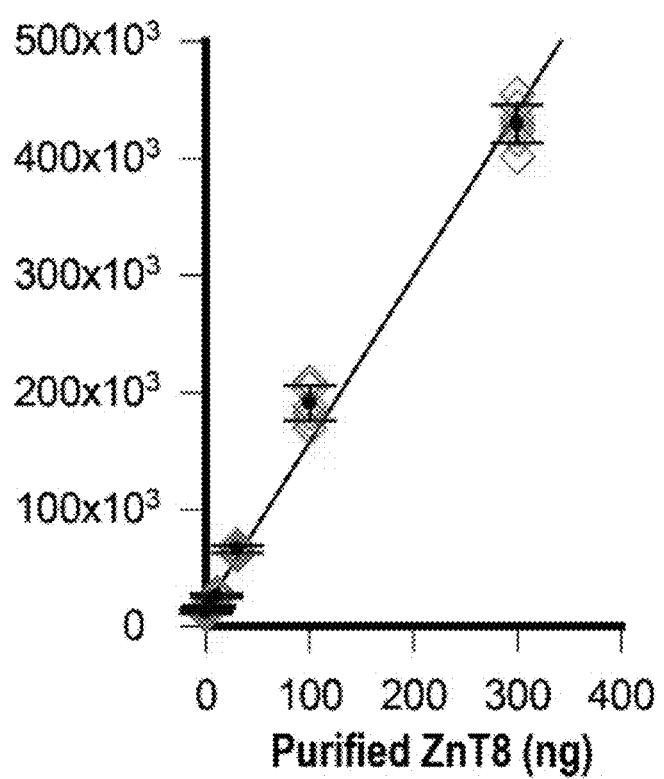

Assay validation. A ZnT8-specific ELISA was developed to track the endogenous ZnT8 level in EndoC-µH1 cells immobilized to a 96-well plate by paraformaldehyde fixation, followed by immunostaining and horseradish peroxidase (HRP) chemiluminescence. The non-specific background was estimated using rat insulinoma INS-1E and human HEK293 cells as negative controls. The present inventors tested two recently developed anti-ZnT8 mAbs (mAb20 and mAb39). Although both mAbs had a subnanomolar binding affinity (33), only mAb20 had a significant signal-to-noise ratio when endogenous ZnT8 in EndoC-βH1 cells was probed at a saturating mAb concentration (1:600 dilution). Assay calibration showed a linear increase in the HRP-readout with the cell number that was proportional to the amount of endogenous ZnT8 (FIG. 1A). The signal-to-noise ratio at $95 \times 10^3$ cells was 3.9 (Z' score=0.8) over a background detected from a same number of INS-1E cells (FIG. 1A). The non-specific background was further reduced for HEK293 cells with negative ZnT8 expression (FIG. 1A). Mixing HEK293 cells with and without heterologous ZnT8 expression showed a linear ZnT8-ELISA response extending to a limit of quantification (LOQ) (FIG. 1B), corresponding to ~1,000 HEK293 cells with doxycycline-induced ZnT8 expression under a Tet-repressor (34). Assay calibration using purified human ZnT8 immobilized to a Ni-NTA plate via a C-terminal His-tag also yielded a liner ELISA response (FIG. 1C).

ZnT8 responses to metabolic and zinc stress. The present inventors used ZnT8-ELISA to characterize endogenous ZnT8 responses to T2D-relevant stimuli. It was well established that elevated Glc/FFA levels acutely increased β-cell mass and insulin production, but continuous exposures led to glucolipotoxicity (35). Accordingly, the present inventors used a mixture of Glc and palmitic acid (PA) to mimic metabolic stress and measured the dose response of endogenous ZnT8 to serial dilutions of the mixture starting from 48 mM Glc plus 0.6 mM PA. At a fixed timepoint of 24 hr post metabolic stress, the endogenous ZnT8 level in EndoC-βH1 cells showed small fluctuations within experimental errors (FIG. 2A). By comparison, the endogenous ZnT8 level showed a biphasic change when the extracellular zinc concentration was progressively increased from a trace amount by EDTA chelation to 600 µM (FIG. 2B). The biphasic profile was peaked around 10 µM zinc, indicating that the cellular ZnT8 level was first up- and then down-regulated in response to a switch of the zinc status from deficiency to overload.

ZnT8 response to inflammatory stress. The pancreatic β-cell is a target of cytokines as inflammatory mediators of functional suppression and cell death during the development of both T1D and T2D (25,36). The present inventors used a master cytokine cocktail consisting of IL-1β (5 ng/ml), IFN-γ (50 ng/ml), IL-17 (100 ng/ml) and TNF-α (10 ng/ml) to mimic the in vivo cytokine load in islet inflammation (37). EndoC-βH1 cells were exposed to a sequence of cytokine concentrations ranging from 0.01 to 10-fold of the master concentration. After a 24-hr cytokine exposure, the endogenous ZnT8 level showed a graded reduction with increasing cytokine concentrations, reaching a steady-state at 48.6% of the untreated control (FIG. 2C). Next, the time course of cytokine actions was examined. At a fixed 1× cytokine concentration, cytokine exposure induced an exponential decay of the endogenous ZnT8 level with a time constant of 8.5±0.3 hr (FIG. 2D). Still next, the present inventors examined the reversibility of cytokine-induced ZnT8 downregulation. EndoC-βH1 cells were first exposed to 1× cytokine cocktail for 24 hr, and then recovered in a cytokine-free medium for different time periods. The endogenous ZnT8 level increased exponentially with a time constant of 3.7±0.5 hr (FIG. 2E), but the recovery only reached 75.4% of the endogenous ZnT8 level in untreated EndoC-βH1 cells. The lack of a full recovery was likely caused by the presence of residual cytokines after switching to the cytokine-free medium. As shown in FIG. 2C, the lowest cytokine concentration (0.01×) used in the experiment still induced a solid 19.3% ZnT8-downregulation, suggesting that a trace amount of residual cytokine could prevent a full recovery. Taken together, cytokines elicited an acute, graded and reversible ZnT8 downregulation over a 1,000-fold concentration range.

Adaptive cellular responses. The reversibility of cytokine-induced ZnT8 downregulation reflected an adaptive cellular response to inflammatory stress. To evaluate the extent of cell damage under different types of stress, the present inventors used a DNA binding fluorescence dye to monitor changes in the cell membrane integrity. 1× Glc+PA and modest zinc exposure (<=200 µM) did not alter the cell integrity as compared to untreated cells (FIG. 2F). Cytokines progressively compromised cell integrity with increasing concentrations. However, normalizing the cytokine-induced fluorescence increase to that of detergent-induced cell lysis indicated that less than 10% of cells was damaged following a 10× cytokine exposure for 48 hr (FIG. 2F). A 1× cytokine exposure for 24 hr increased the relative CellTox intensity to 53% from a background level of the untreated control at 4.1% (FIG. 2F). Thus, the cytotoxicity level was negligibly low, consistent with earlier findings that a similar cytokine cocktail exposure did not induced proapoptotic markers in EndoC-βH1 cells (38).

Figure 3D:
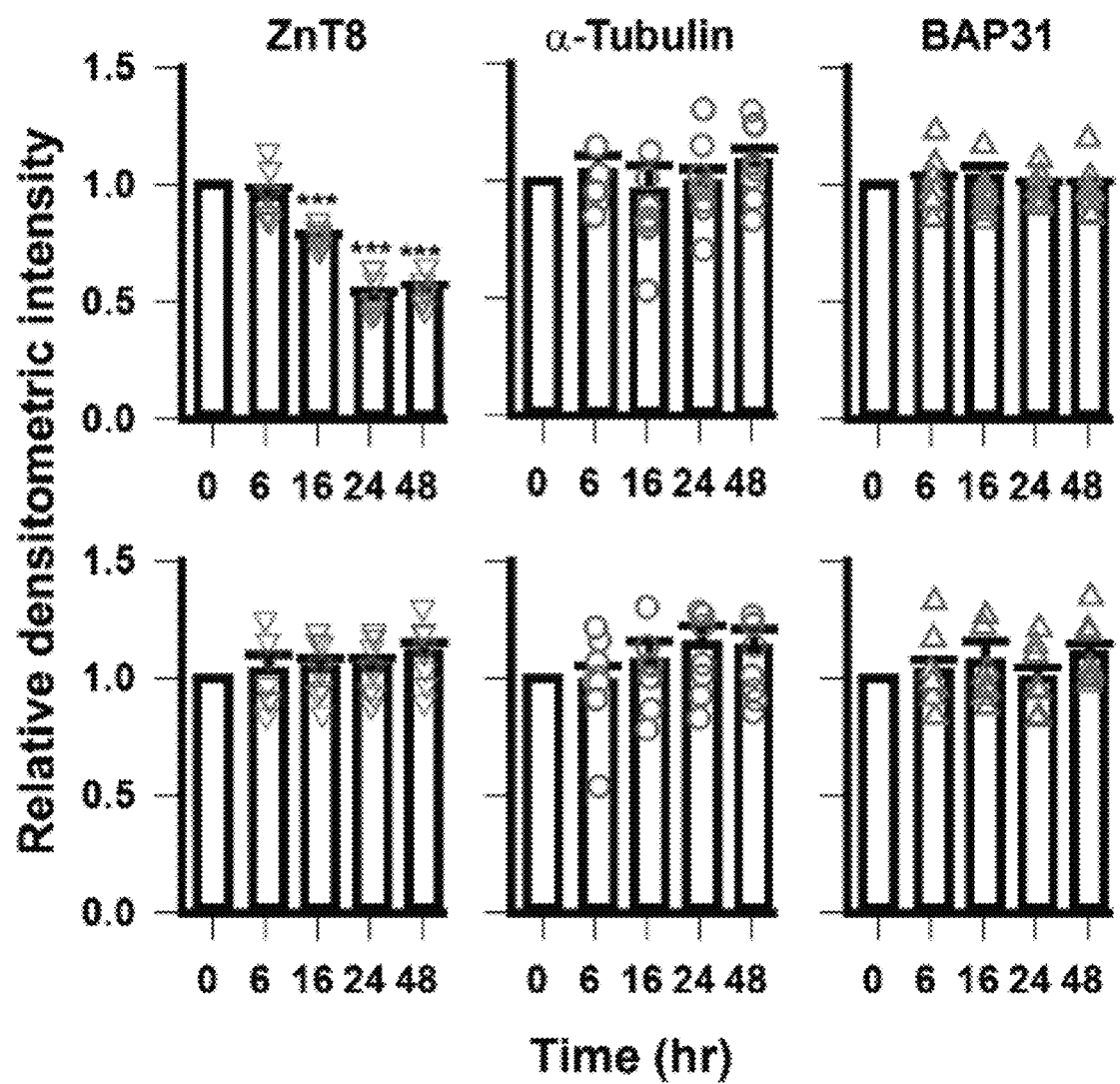

Selective ZnT8 targeting. To further evaluate the effects of metabolic and inflammatory stress on the insulin secretory pathway, the present inventors exposed EndoC-βH1 cells to 1× cytokine or 1× Glc+PA for 24 hr, and then used immunoblotting to compare protein expression levels with and without the stress exposure. Total cell lysates were probed by antibodies to ZnT8 (mAb20), two ER-resident membrane proteins (BAP31 and calnexin), two ISG-resident membrane proteins (IA2 and VAMP2), an ER/Golgi membrane protein (TMED3) (39). Three proteins outside of the insulin secretory pathway (α-tubulin, GAD65 and SCD) were analyzed in parallel. Using α-tubulin as an internal control on the same immunoblot, the present inventors observed a marked reduction of ZnT8 in cytokine-treated cells, but no change in GlcαPA treated cells (FIG. 3A). Of note, mAb20 detected two naturally occurring SLC30A8 splice variants (40), and their combined intensity was compatible to that of α-tubulin (FIG. 3A). Other tested membrane proteins except IA2 showed no change following either cytokine or metabolic stress (FIG. 3B). Cytokine exposure induced an insignificant IA2 reduction as compared to a more pronounced ZnT8 downregulation (FIG. 3C). Two additional proteins, GAD65 and SCD, showed differential responses to cytokine and metabolic stress (FIG. 3C, detailed below). Moreover, densitometric quantification at different timepoints of stress exposures showed a time-dependent decline of the endogenous ZnT8 level after cytokine exposure, but no difference following metabolic stress up to 48 hr (FIG. 3D). This immunoblotting result validated independent measurements by ZnT8-ELISA (FIG. 2C-D). The α-tubulin and BAP31 levels also remained unchanged under both cytokine and metabolic stress for 48 hr (FIG. 3D). In β-cells, BAP31, calnexin, TMED3, VAMP2, IA2 and ZnT8 are distributed along the insulin secretory pathway from ER to ISG. Among these proteins, ZnT8 showed strongest cytokine-responsiveness, acting as a selective target of cytokine-induced downregulation.

Figure 4C:
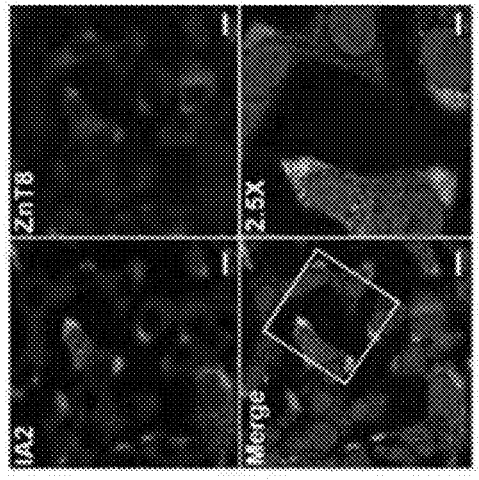
FIG. 4A-4F. Confocal microscopy imaging of ZnT8 colocalization with organelle markers in EndoC-βH1 cells. Cells were immunostained with mouse mAb20 together with a rabbit antibody to insulin (FIG. 4A), BAP31 (FIG. 4B), IA2 (FIG. 4C), VAMP2 (FIG. 4D), TEMD3 (FIG. 4E) or Golgin97 (FIG. 4F) as indicated. The mouse and rabbit primary antibody were visualized by an anti-mouse (red) and anti-rabbit (green) secondary antibody, respectively. A region of interest in the merge window was marked and shown in 2.5× magnification. Scale bars are 10 μm in 1× and 4 μm in 2.5× windows.
Figure 4F:
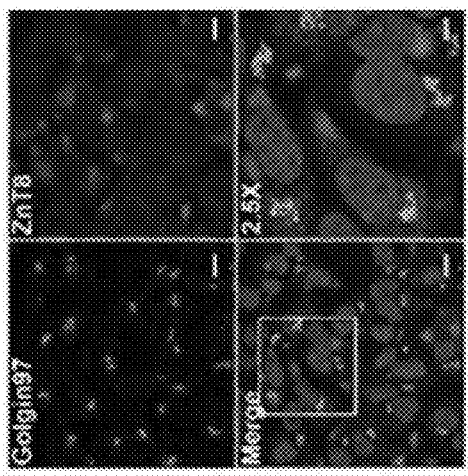
Figure 4B:
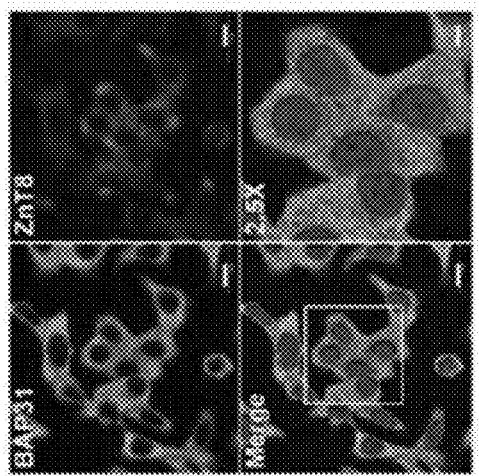
Figure 4E:
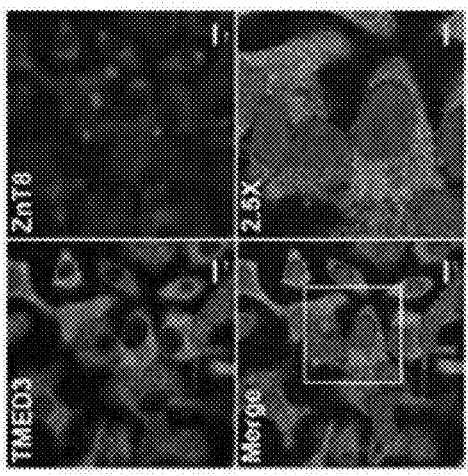
Figure 4A:
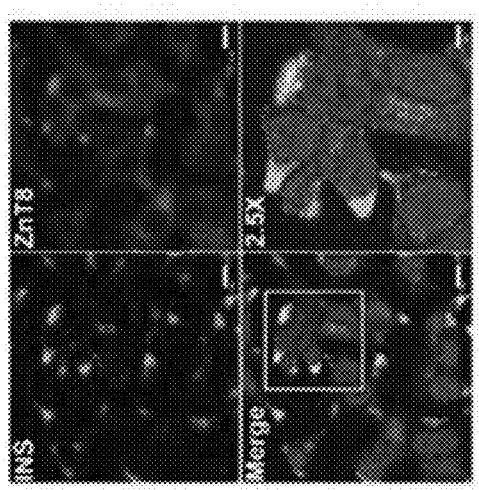
Figure 4D:
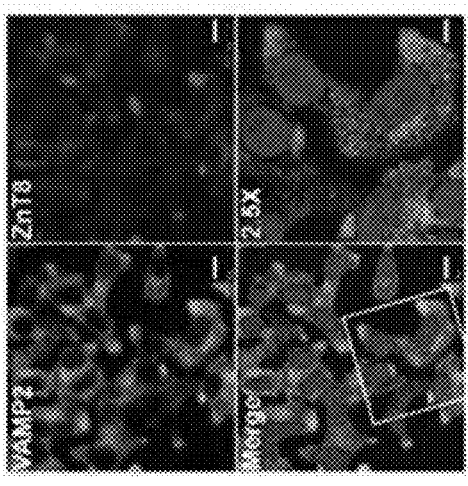

Localization of ZnT8 to the ER. Previous work established that ZnT8, IA2 and VAMP2 were localized to ISGs of pancreatic β-cells (41-43). The differentiated response of ZnT8 from that of IA2 and VAMP2 prompted a re-evaluation of ZnT8 subcellular localization. Co-immunostaining EndoC-βH1 cells with mAb20 and a rabbit polyclonal antibody to insulin, BAP31, IA2, VAMP2, TMED3 or Glogin97 revealed two distinct levels of ZnT8 immunofluorescence intensities. A lower but broadly distributed intensity appeared co-localized with BAP31, TMED3 and partly with IA2 and VAMP2 immunofluorescence while a high but confined intensity overlapped the immunofluorescence of insulin, and partly IA2 and VAMP2 (FIG. 4A-E). Co-immunostaining ZnT8 and the Golgi marker Golgin-97 suggested no immunofluorescence overlap (FIG. 4F). Quantitative analysis gave Manders' split coefficients (MSC) of 1.00 in respective regions of interest (ROIs) for the following protein pairs, ZnT8-insulin, ZnT8-BAP31 ZnT8-

TMED3, ZnT8-VAMP2 and ZnT8-IA2 whereas the MSC value for the ZnT8-Golgin97 pair was 0.20. Thus, confocal imaging suggested a broad ER localization of endogenous ZnT8 in addition to its high-density clustering associated with ISGs.

Figure 5A:
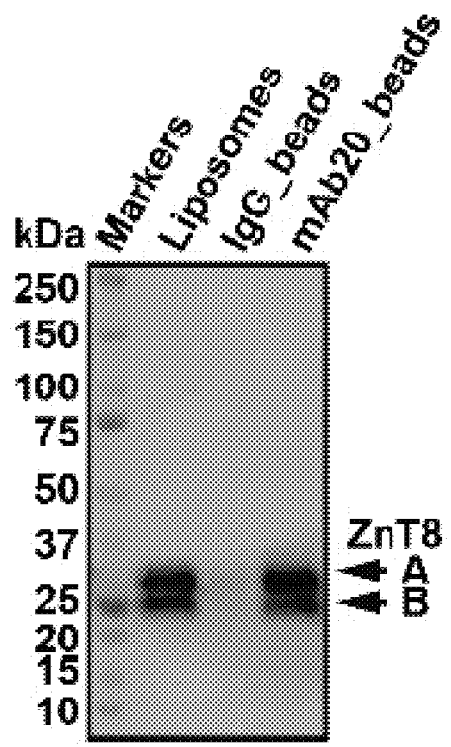
FIG. 5A-5E. Co-immunoprecipitation and quantification of ZnT8.
Figure 5B:
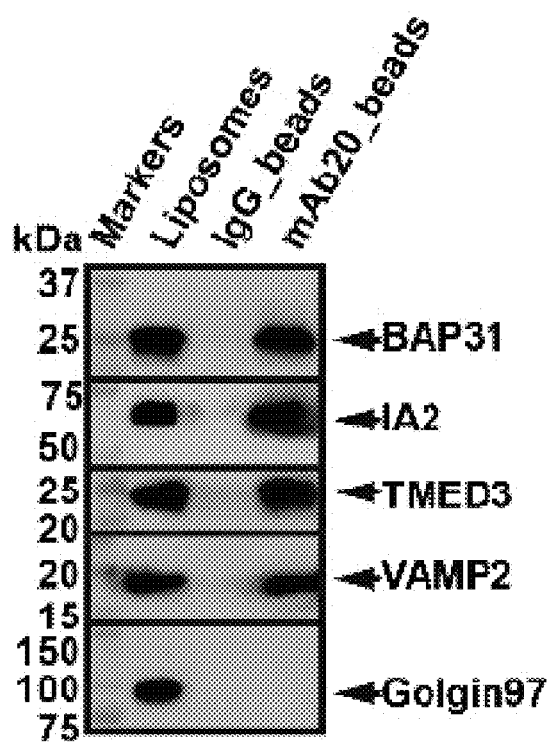

The present inventors validated the imaging observations by co-immunoprecipitation. Homogenous liposomes (~100 nm in diameter based on light scattering measurements) derived from EndoC-βH1 cells were captured by mAb20-PEG5K-Dynabeads. Proteins in proximity to ZnT8 in liposomes were probed by immunoblotting. Dynabeads conjugated with mouse IgG via the same PEG5K linker were used to assess nonspecific liposome capture. The membrane sidedness of the liposomal preparation was ~50% right-side-out and ~50% inside-out. mAb20 on magnetic beads captured right-side-out liposomes while non-specific liposome binding to IgG-PEK5k-beads was not detected (FIG. 5A). Immunoblotting analysis of captured liposomes using antibodies to BAP31, IA2, TMED3 or VAMP2 showed that each of these proteins was co-immunoprecipitated with ZnT8. In contrast, Golgin97 was not detected (FIG. 5B) in agreement with the confocal imaging results (FIG. 4).

Figure 5C:
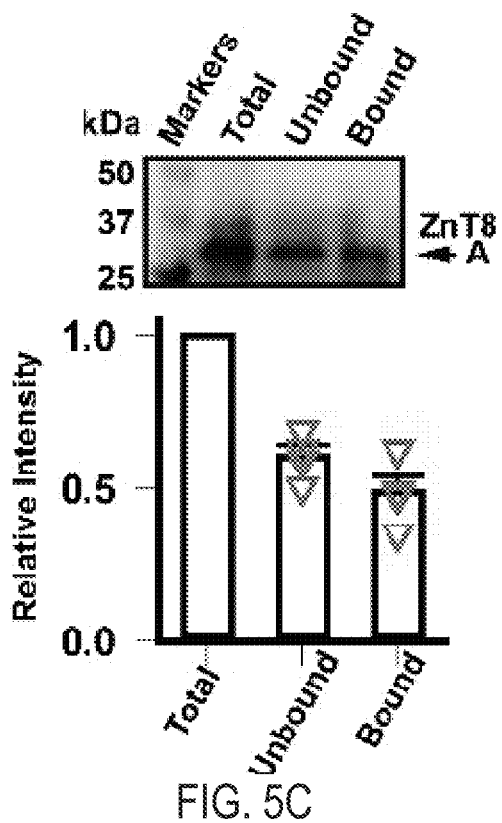
Figure 5D:
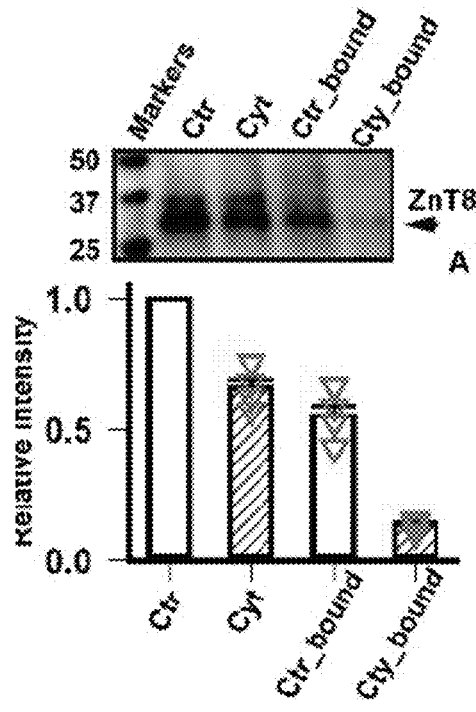
Figure 5E:
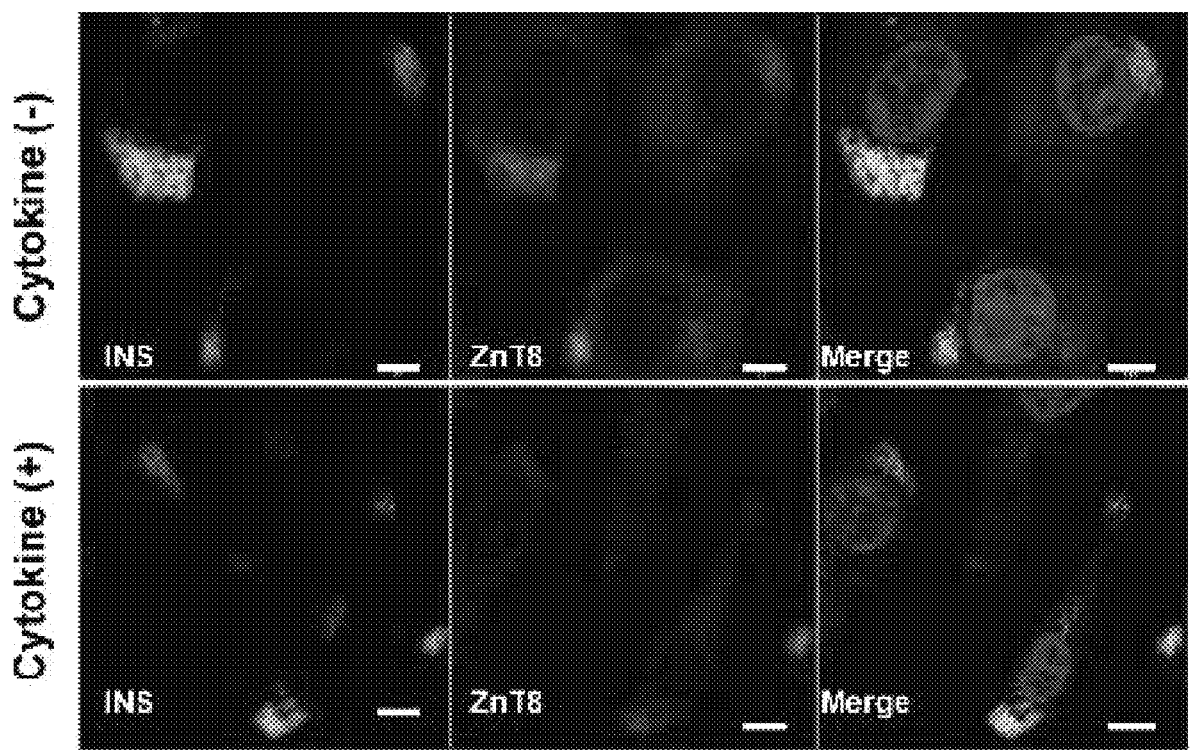

Quantification of ER-resident ZnT8. To estimate the amount of ER-associated ZnT8 relative to the total ZnT8 in EndoC-βH1 cells, the present inventors conjugated a polyclonal BAP31 antibody to Dynabeads which could capture >95% BAP31-liposomes because this polyclonal antibody recognized multiple BAP31 epitopes on both sides of the membrane. ZnT8 in the captured BAP31-liposomes was detected on immunoblots by biotinylated mAb20 followed by HRP-conjugated streptavidin. The use of biotinylated mAb20 avoided detection of a small amount of pAb light-chains that were partially co-eluted with ZnT8 and detected at a position close to that of ZnT8 on immunoblots. Each ZnT8 protein band on the immunoblot was measured and normalized to the total ZnT8 in the cell lysate. Densitometric quantification showed that 60.4±4% ZnT8 in the cell lysate were in the flow-through (unbound) while 48.7±6% ZnT8 were captured (bound) by anti-BAP31-conjugated beads (FIG. 5C), yielding an estimate of about 50% of cellular ZnT8 associated with ER. Next, the present inventors compared the cytokine effects on total and ER-associated ZnT8. Exposing EndoC-βH1 cells to 1× cytokine cocktail for ~16 hr reduced the total cellular ZnT8 to 66±3% relative to the untreated control (100%) (FIG. 5D), in agreement with the results presented in FIG. 2D and FIG. 3D. By comparison, anti-BAP31-conjugated beads captured 55.5±4% of total ZnT8 in untreated cells versus 13.8±1% of total ZnT8 in cytokine-treated cells (FIG. 5D). The ratio of 13.8/55.4 indicated that cytokine exposure reduced the ER-resident ZnT8 to 24.9% of the pre-exposure level. Compared to a 66% post-cytokine level for total cellular ZnT8, cytokines had a more pronounced effect on ER-resident ZnT8. Confocal imaging showed that 1× cytokine-exposure for 24 hr resulted in a near complete loss of ER-associated ZnT8 immunofluorescence while the ISG-associated signal remained largely unchanged (FIG. 5E), further indicating that ER was the primary site of cytokine-induced ZnT8 downregulation.

Response of HLA-I molecules. Since the endogenous levels of BAP31, calnexin, TMED3, VAMP2 and IA2 showed no or insignificant responsiveness to stress exposures, the present inventors further examined stress-induced perturbation of two additional proteins, HLA-I molecules (44) and insulin (45). Exposing EndoC-βH1 cells to 1× cytokine cocktail for 24 hr activated a marked HLA-I hyperexpression over a low background of untreated cells whereas 1× Glc+PA exposure did not affect the HLA-I expression level (FIG. 6A). The ZnT8 level on the same immunoblot reduced by ~50% concurrently with a 13.4-fold increase in HLA-I expression, demonstrating a bidirectional response of EndoC-βH1 cells to cytokine stimulation (FIG. 6A). A high signal-to-noise ratio of the HLA-I signal on the immunoblot allowed for in-cell HLA-I ELISA quantification using the commercial anti-HLA-I antibody. A marked HLA-I activation was observed for all concentrations down to 0.01× cytokines. (FIG. 6B). Comparing with ZnT8 downregulation in response to identical cytokine exposures (FIG. 2C), linear regression analysis showed a negative correlation between activation of HLA-I molecules and ZnT8 downregulation (r2=0.77, FIG. 6C), suggesting that peptides derived from ZnT8 degradation may contribute to HLA-I loading.

Figure 7A:
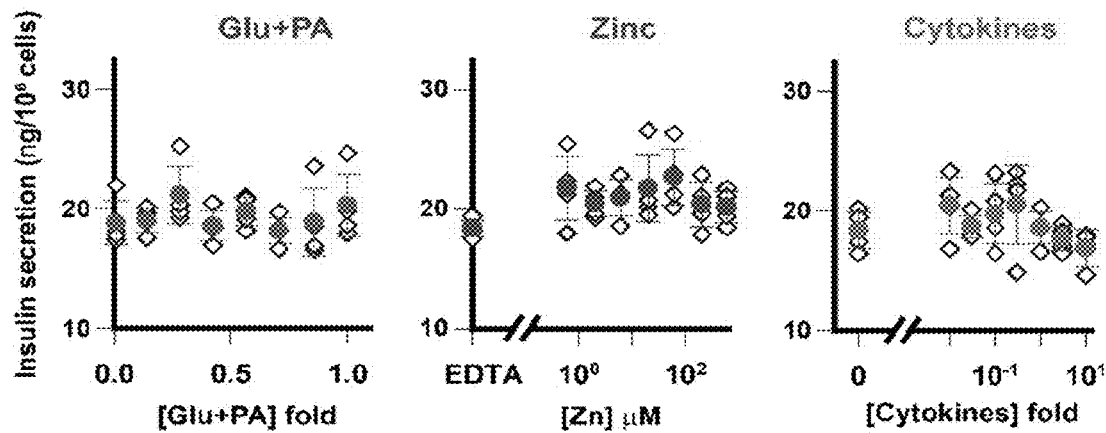
FIG. 7A-7C: Dose responses of insulin secretion, production and their correlations with ZnT8 expression under different stress conditions.
Figure 7B:
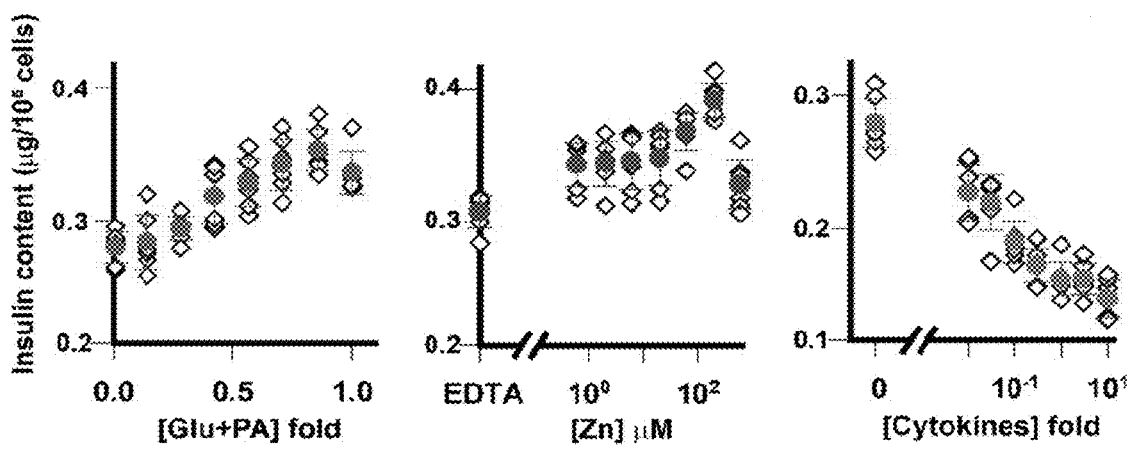

Insulin response. To measure insulin responses to metabolic, zinc and cytokine Stress, the present inventors exposed EndoC-βH1 cells to different stress conditions for 24 hr as described in FIG. 2, and then quantified insulin secretion in response to 20 mM Glc plus 45 μM IBMX (a GSIS enhancer) using a commercial insulin assay based on homogenous time-resolved fluorescence (46). None of the stressors induced a significant change in GSIS (FIG. 7A). By comparison, total insulin contents under different stress conditions exhibited distinct dose-dependent profiles (FIG. 7B). Increasing the Glc-F-PA concentration progressively increased the cellular insulin content in a quasi-linear fashion except for the highest concentration that might approach onset of glucolipotoxicity. Increasing the zinc concentration also increased the insulin content until reaching 600 μM where zinc toxicity was evident (FIG. 2F). Finally, increasing the cytokine concentration induced a monophasic decline of the insulin content to 60% of the untreated control.

Figure 7C:
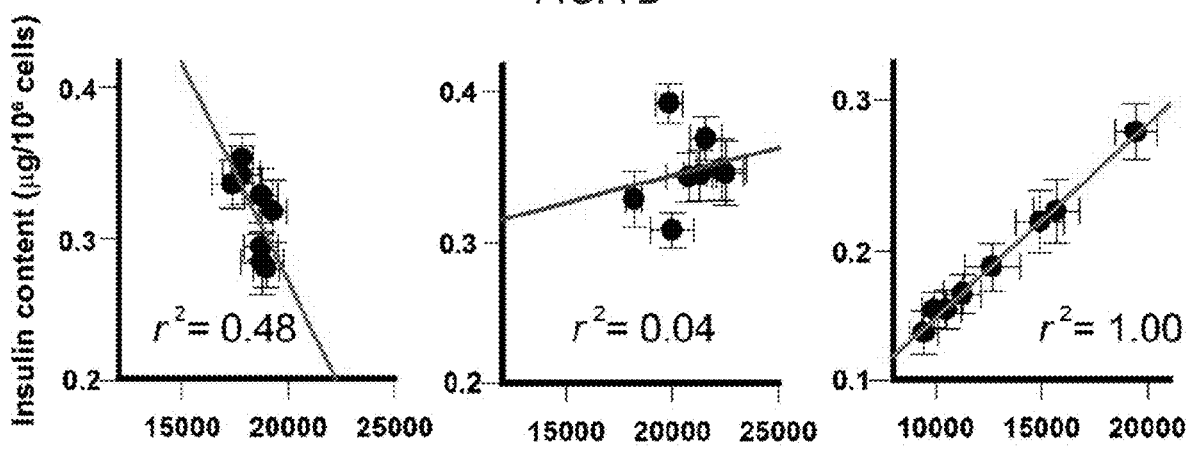

Cytokine-permissive ZnT8-insulin correlation. The distinct dose profiles of insulin responses suggested that the type and dosage of stressor may determine the relationship between ZnT8 expression and insulin production. The present inventors quantified such relationships by linear regression analysis of ZnT8 and insulin dose responses. Glc-PA exposures altered insulin production (FIG. 7B), but not ZnT8 expression (FIG. 2A), yielding a low r2 value of 0.48 (FIG. 7C). Extracellular zinc exposures altered both endogenous ZnT8 (FIG. 2B) and insulin levels (FIG. 7B), but regression analysis yielded a r2 value of 0.04 (FIG. 7lC), indicating a lack of ZnT8-insulin correlation. In contrast, cytokine exposures yielded a striking correlation between ZnT8 (FIG. 2C) and insulin (FIG. 7B) levels with a r2 value of 1.00 (FIG. 7C). Hence, our experiments identified cytokine exposure as a permissive condition for a crosstalk between downregulations of ZnT8 expression and insulin production in a highly coordinated manner.

Molecular underpinnings for differential ZnT8 responses to metabolic and cytokine stress. The lack of ZnT8-insulin correlation under metabolic stress (FIG. 7C) suggested a disconnection of ZnT8 from the regulatory pathway linking metabolic stress to insulin expression. Signaling pathways evoked by metabolic and inflammatory stress are thought to be different (47,48), namely an NF-κB independent mechanism for FFA and an NF-κB dependent mechanism for cytokines (49). Proteomic profiling of rat INS-1 cells before and after acute high PA or Glc+PA exposures revealed a global upregulation of desaturase expression (50), contributing to adaptive FFA detoxification by converting the lipotoxic FAAs to the protective unsaturated species (21,51). Accordingly, the present inventors used stearoyl-CoA desaturase (SCD) as a marker to demonstrate differential stress responses of EndoC-βH1 cells, Anti-SCD immunoblotting showed that SCD expression was upregulated by high Glc+PA exposure, but irresponsive to cytokine stress (FIG. 3C). By comparison, the ZnT8 expression was irresponsive to high Glc-+PA exposure, but downregulated by cytokine stress (FIG. 3D). The differential responses of ZnT8 and SCD validated the divergence of metabolic and cytokine signaling pathways in EndoC-βH1 cells.

Immunoproteasome-mediated co-degradations of ZnT8 and insulin. To illuminate the molecular events leading to parallel downregulations of ZnT8 and insulin in response to cytokine exposure, the present inventors performed Illumina deep sequencing of EndoC-βH1 cells with or without ix cytokine exposure for 24 hr. About 100 million (2×100 bp) paired reads per sample were obtained. Mapping these reads to the human genome (build hg38) identified about 44,000 transcripts per sample. Approximately 600 known genes showed differential expression based on the following criteria: a log fold change ≥1.5, at least one of the Fragments Per Kilobase of transcript per Million (FPKM)≥2 and p-value <0.05. Cytokine exposure did not alter the overall transcription profile (FIG. 8A). The SLC30A8 mRNA level was within top 1% of the transcriptome (FIG. 8A), and showed the largest fold change among all zinc transporters in EndoC-βH1 cells (FIG. 8B). Two ER-resident UPR sensors, inositol requiring enzyme 1 (IRE1) and PKR-like ER kinase (PERK), were upregulated by cytokine exposure. Another UPR sensor, activating transcription factor 6 (ATF6), was slightly suppressed, but the ATF6 associated CREB3 sensor was upregulated (Table 1). Thus, all three branches of the UPR were engaged in cytokine stress (52). In support of this notion, ER chaperones (BIP, CANX and CALR), protein disulfide isomerase (PDIA3, 4, and 6) and key transcription factors involved in adaptive UPR signaling (XBP1, ATF4) were all significantly upregulated (Table 1). The NF-κB inflammatory signaling pathway was activated as expected for cytokine stimulations, but key components of the apoptotic program (53), JNK, CHOP and caspases, remained either unchanged or at a low level (FPKM<60) with an apparently significant fold-increase (Table 1). In contrast, genes in the ER-associated protein degradation (ERAD) pathway were sharply activated, including LMP2, LMP7 and MECl-1 that encoded three catalytic subunits of immunoproteasomes with a 436.5, 128.1 and 9.6-fold increase, respectively (Table 1). These immunoproteasome components were distinctly positioned off-diagonal in a linear correlation of EndoC-βH1 transcriptomes with and without cytokine exposure, indicating a prominent cytokine-induced activation of ERAD (FIG. 8C).

Figure 9A:
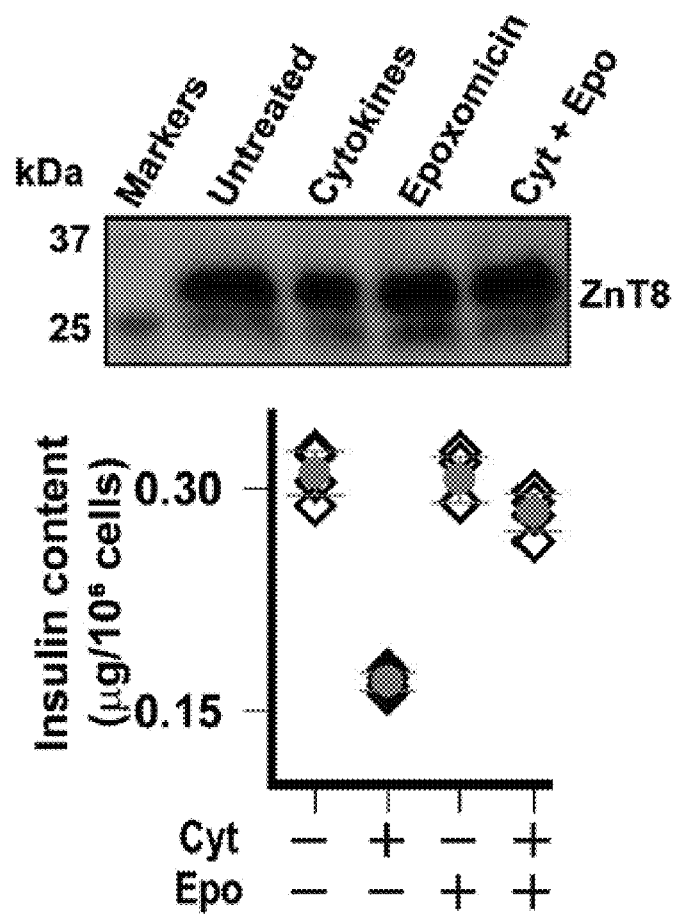
FIG. 9A-9D. Inhibition of ZnT8 and insulin degradation and cytoprotection by ZnT8 knockdown.
Figure 9B:
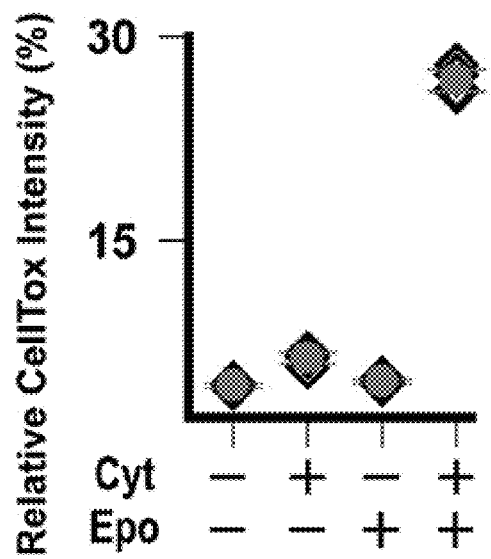

The proteolytic activities of LMP2, LMP7 and MECl-1 are essential to generating antigenic peptides with a hydrophobic C-terminus for proper HLA-I loading (54). ZnT8 and insulin are two major β-cell autoantigens susceptible to immunoproteasome digestion and HLA-I presentation on pancreatic β-cells (10,55-58). A dramatic increase of the HLA-I protein level and its negative correlation with the endogenous ZnT8 level (or positive correlation with ZnT8 degradation) (FIG. 6C) suggested that immunoproteasome may mediate cytokine-induced ZnT8 ERAD for HLA-I loading. To test this hypothesis, the present inventors used a membrane permeable natural product epoxomicin to specifically inhibit LMP7 and MECL-1 (59). Exposing EndoC-βH1 cells to epoxomicin blocked cytokine-induced downregulations of both ZnT8 and insulin (FIG. 9A), indicating a shared immunoproteasome-mediated ERAD pathway for ZnT8 and insulin degradation. Epoxomicin alone neither altered ZnT8 expression nor affected cell viability (FIG. 9A-B). However, a combination of epoxomicin and Ix cytokine triggered apoptosis, resulting in 26.8% of damaged cells following a 24 hr exposure (FIG. 9B).

Figure 9C:
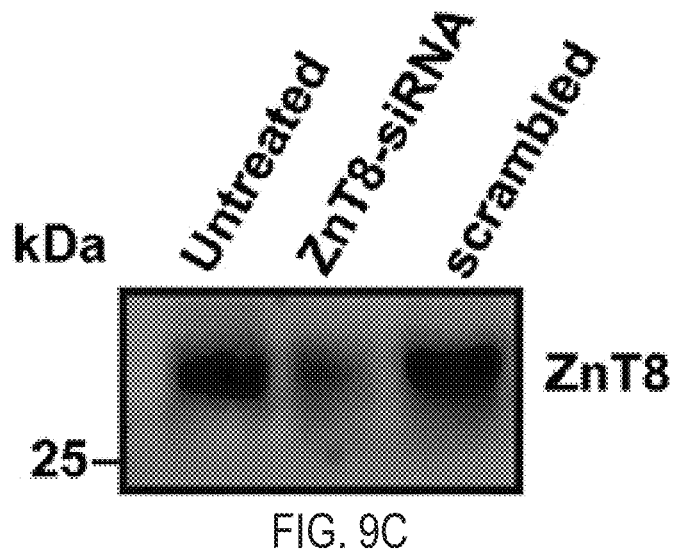

ZnT8 knockdown reduced cytokine-induced cell damage. The proapoptotic effect of the combined actions of epoxomicin and cytokine suggested that a blockade of immunoproteasome-mediated ZnT8 degradation triggered a transition from adaptive to proapoptotic UPR under cytokine stress. This finding raised the possibility that reducing the ZnT8 ER burden may promote adaptive UPR response. To test this hypothesis, the present inventors used small interference RNA (siRNA) to reduce the cellular ZnT8 level and monitored cytokine-induced loss of cell integrity by the CellTox fluorescence assay. Transfection of EndoC-βH1 cells with ZnT8-targeting siRNAs caused a ~70% reduction in the ZnT8 protein level whereas scrambled siRNA had no effect (FIG. 9C). ZnT8-knockdown markedly reduced cell damage induced by 15× cytokine exposures for 24 hr (FIG. 9D), demonstrating that ZnT8 knockdown significantly attenuated cytokine cytotoxicity.

DISCUSSION

ZnT8 is generally thought to be a simple zinc transporter performing a zinc enrichment role in ISGs. Our results indicate that ZnT8 is temporally and spatially regulated to modulate zinc, ER and insulin homeostasis. Our recent findings also showed that GSIS promotes ZnT8 trafficking to the surface membrane (60) where ZnT8 becomes a surface autoantigen recognized by autoantibodies arose front autoimmunity in T1D (33,61). Hence, emerging evidence suggests crosstalks among multiple regulatory pathways intersecting at ZnT8 to shape the unique cell biology of pancreatic β-cells with exceptionally high zinc content. The current research paradigm based on SLC30A8 deletion/overexpression carries a significant liability for experimental artifacts due to drastic perturbation of a multitude of signaling pathways. The mAb20-based in-cell ZnT8-assay allows for tracking fluctuations of endogenous ZnT8 levels, establishing ZnT8 as a major cytokine-responsive UPR client protein in ER.

Figure 9D:
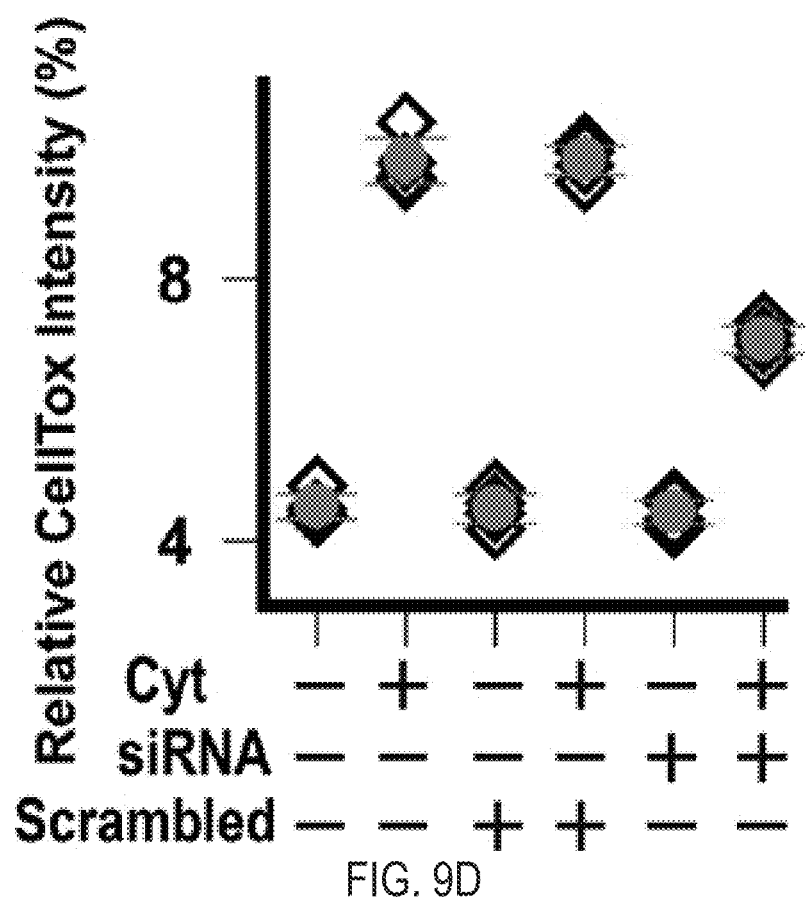

SLC30A8 is highly expressed in human pancreatic β-cells (FIGS. 3A and 8A), imposing a significant ER burden which is also under pressure of high demand on insulin production and secretion. Cytokine exposure may further render μ-cells susceptible to accumulation of misfolded proteins, exacerbating ER stress (45). Our experiments showed that human β-cells responded to acute cytokine exposure with a rapid, graded and reversible downregulation of the cellular ZnT8 level. These findings are consistent with earlier studies of cytokine-regulated SLC30A8 expression in rodent β-cells with some differences in the effects on GSIS and the cellular insulin content (62-64). The present inventors found that cytokine-induced ZnT8 downregulation did not affect GSIS in human insulinoma cells, but strongly correlated with the insulin content. The coupled downregulations of ZnT8 and insulin provide direct evidence for UPR converging on two major ER burdens, highlighting the importance of ZnT8 and insulin decongestion in restoring ER homeostasis under inflammatory insult. In support of this notion, blocking ZnT8 degradation by an immunoproteasome inhibitor accelerated cell death whereas facilitating ZnT8 downregulation by siRNA knockdown protected cells against cytokine cytotoxicity (FIGS. 9B and 9D). These results are in line with a previous finding that SLC3018 overexpression potentiated IL-1β induced apoptosis of rat pancreatic μ-cells (63).

Human genetics data and functional studies of ZnT8 polymorphic variants provided further support for a pathogenic effect of ZnT8 upregulation. A nonsynonymous polymorphic variant of ZnT8 (R325) has a higher zinc transport activity (34,65) and thermostability (66), and this polymorphism is associated with a higher T2D risk (11). This causal relationship is further validated by a recent exome sequencing analysis of human populations with and without T2D (67).

The responsiveness of ER-resident ZnT8 to cytokine stimulations may also contribute to restoring zinc homeostasis in ER, which has an enriched luminal concentration (≥5 nM) over a low cytosolic zinc level (0.1-1 nM) (68). Among all zinc transporters in EndoC-βH1 cells, SLC39A7 is the second highest transcribed gene after SLC30A8 and also has a significant cytokine response at the mRNA level (FIG. 81B). SLC39A7 encodes a major zinc-release transporter ZIP7 in ER (69,70). The reduction of SLC30A8 transcript appears functionally synergetic with an increase of SLC39A7 because ZnT8 and ZIP7 transport zinc in opposite directions across the ER membrane (5,6). ZIP7 upregulations were found to attenuate ER stress in MG-63 osteosarcoma cells, intestinal epithelial cells and embryonic rat heart-derived cells (H9c2) (71-73). Likewise, cytokine-induced ZnT8 downregulation may attenuate ER-stress by reducing the ER zinc content, which may be tuned to a reduced demand on zinc for proinsulin loading. Hence, a coupling between ZnT8 expression and insulin production may be of physiological significance for the zinc-dependent process of proinsulin folding and processing (74).

Understanding how cellular ZnT8 responds to disease-driving stress is the first step toward understanding the role of ZnT8 in T2D pathogenesis. Our experiments reveal differential ZnT8 responses to metabolic and inflammatory stress, and establish a novel immunologic connection between cytokine-induced ZnT8 downregulation and β-cell adaptive UPR through immunoproteasome-mediated co-degradation of two major β-cell autoantigens. Autoantibodies to ZnT8 or insulin, together to two additional autoantigens IA2 and GAD65, were found in approximately 94% of patients with T1D (75). While these autoantigens are believed not to activate cytotoxic T-cells in T2D, our results revealed selective cytokine susceptibilities of ZnT8 and insulin over IA2 and GAD65 (FIG. 3). A robust cytokine-induced ZnT8 and insulin downregulations at a concentration 1000-fold below the cytotoxicity level (FIGS. 2C and 7B) suggests a functional relevance to chronic activation of the innate immune system associated with obesity (25).

Besides being a possible player in obesity-driven low-grade inflammation that predisposes individuals to develop T2D, ZnT8 as a major autoantigen elicits both humoral and cellular autoimmunity in the development of T1D (9,10,76, 77). Hence, the pathogenesis of T1D and T2D appears to intersect at ZnT8 that confer on β-cells the immune susceptibility. The identification of ZnT8 as a cytokine-responsive ER burden links β-cell inflammation to ER stress while the protective effect of ZnT8 downregulation for inflamed β-cells suggests a potential therapeutic strategy to mimic the natural protection of SLC30A8 haploinsufficiency found in humans with lower T2D risk (12). A caveat to increasing β-cell resilience by ZnT8 downregulation is a parallel downregulation of insulin production (FIG. 7C), potentially leading to a loss of insulin secretory capacity under prolonged and severe inflammatory exposure. Further research is needed to inform on a strategy to modulate the ZnT8 level to balance β-cell survival and insulin production in inflamed pancreatic islets.

TABLE 1

Cytokine-induced differential gene expression as determined by RNA-seq

| Gene | Control (FKPM) | Cytokine (FKPM) | Fold change | Protein Function |
| --- | --- | --- | --- | --- |
| SLC30A8 | 287.2 ± 10.4 | 169.1 ± 3.0 | 0.6 | ZnT8, ISG/ER zinc sequestration |
| SLC39A7 | 113.0 ± 2.4 | 129.3 ± 4.1 | 1.1 | ZIP7, ER/Golgi zinc release |
| INS + read-throughs | 30768.8 ± 1367.6 | 24920.6 ± 688.2 | 0.8 | Insulin, ISG |
| IRE1 | 4.3 ± 0.2 | 9.9 ± 0.2 | 2.3 | UPR sensor |
| PERK | 7.9 ± 0.5 | 12.1 ± 1.3 | 1.5 | UPR sensor |
| ATF6 | 9.3 ± 0.4 | 8.2 ± 0.1 | 0.9 | UPR sensor |
| CREB3 | 19.9 ± 0.2 | 29.7 ± 0.9 | 1.5 | ATF6-assocated UPR sensor |
| BIP (GRP78) | 186.3 ± 5.0 | 466.8 ± 8.1 | 2.5 | ER chaperon protein |
| CANX | 321.6 ± 13.4 | 469.9 ± 27.1 | 1.5 | ER chaperon protein |
| CALR | 647.1 ± 12.9 | 1201.0 ± 14.5 | 1.9 | ER chaperon protein |
| PDIA3 | 438.2 ± 8.4 | 882.3 ± 1.8 | 2.0 | Protein disulfide isomerase |
| PDIA4 | 130.5 ± 2.5 | 353.9 ± 6.7 | 2.7 | Protein disulfide isomerase |
| PGIA6 | 208.2 ± 1.9 | 403.2 ± 1.8 | 1.9 | Protein disulfide isomerase |
| XBP1 | 119.4 ± 1.0 | 203.2 ± 1.5 | 1.7 | Adaptive UPR kinase |
| ATF4 | 178.8 ± 5.2 | 214.4 ± 0.1 | 1.2 | Adaptive UPR kinase |
| NFKB1 | 10.1 ± 0.4 | 17.5 ± 0.5 | 1.7 | Proinflammatory signaling kinase |
| NFKB2 | 8.7 ± 0.5 | 34.9 ± 0.2 | 4.0 | Proinflammatory signaling kinase |
| MAPK8(JNK1) | 26.6 ± 0.9 | 20.9 ± 0.5 | 0.8 | Proapoptotic UPR kinase |
| MAPK9(JNK2) | 22.6 ± 0.6 | 17.2 ± 0.4 | 0.8 | Proapoptotic UPR kinase |
| MAPK10(NK3) | 24.6 ± 0.8 | 27.3 ± 0.9 | 1.1 | Proapoptotic UPR kinase |
| CHOP(DDIT3) | 12.6 ± 0.6 | 36.7 ± 1.9 | 2.9 | Proapoptotic UPR kinase |
| CASP2 | 40.3 ± 0.18 | 23.2 ± 0.6 | 0.6 | Proapoptotic caspase cascade |
| CASP3 | 25.5 ± 0.5 | 40.8 ± 0.5 | 1.6 | Proapoptotic caspase cascade |
| CASP4 | 4.8 ± 0.4 | 58.6 ± 3.2 | 12.2 | Proapoptotic caspase cascade |
| CASP9 | 8.3 ± 0.4 | 6.5 ± 0.6 | 0.8 | Proapoptotic caspase cascade |

TABLE 1-continued

Cytokine-induced differential gene expression as determined by RNA-seq

| Gene | Control (FKPM) | Cytokine (FKPM) | Fold change | Protein Function |
|---|---|---|---|---|
| PSMB8 | 10.7 ± 0.3 | 1371.2 ± 16.6 | 128.1 | ERADE, Immunoproteasomes, LMP7 |
| PSMB9 | 1.7 ± 0.2 | 742.1 ± 7.9 | 436.5 | ERADE, Immunoproteasomes, LMP2 |
| PSMB10 | 21.4 ± 1.4 | 205.8 ± 2.1 | 9.6 | ERADE, Immunoproteasomes, MEC1-1 |

REFERENCES

1. Schuit, F. C., In't Veld, P. A., and Pipeleers, D. G. (1988) Glucose stimulates proinsulin biosynthesis by a dose-dependent recruitment of pancreatic beta cells. *Proc Natl Acad Sci USA* 85, 3865-386.
2. Dodson, G., and Steiner, D. (1998) The role of assembly in insulin's biosynthesis. *Curr Opin Struct Biol.* 8, 189-194.
3. Foster, M. C., Leapman, R. D., Li, M. X., and Atwater, I. (1993) Elemental composition of secretory granules in pancreatic islets of Langerhans. *Biophys J* 64, 525-532.
4. Vinkenborg, J. L., Nicolson, T. J., Bellomo, E. A., Koay, M. S., Rutter, G. A., and Merkx, M. (2009) Genetically encoded FRET sensors to monitor intracellular Zn2+ homeostasis. *Nat Methods* 6, 737-740.
5. Huang, L. (2014) Zinc and its transporters, pancreatic beta-cells, and insulin metabolism. *Vitam Horm* 95, 365-390.
6. Kambe, T., Hashimoto, A., and Fujimoto, S. (2014) Current understanding of ZIP and ZnT zinc transporters in human health and diseases. *Cell Mol Life Sci* 71, 3281-3295.
7. Lemaire, K., Chimaienti, F., and Schuit, F. (2012) Zinc transporters and their role in the pancreatic beta-cell. *J Diabetes Investig* 3, 202-211.
8. Segerstolpe, A., Palasantza, A., Eliasson, P., Andersson, E. M. Andreasson. A C., Sun, X., Picelli, S., Sabirsh, A., Clausen. M., Bjursell, M. K., Smith., D. M., Kasper, M., Ammala, C., and Sandberg, R. (2016) Single-Cell Transcriptome Profiling of Human Pancreatic Islets in Health and Type 2 Diabetes. *Cell Metab* 24, 593-607.
9. Wenzlau, J. M., Juhl, K., Yu, L., Moua, O., Sarkar, S. A., Gottlieb, P. Rewers, M., Eisenbarth, G. S., Jensen, J., Davidson, H. W., and Hutton. J. C. (2007) The cation efflux transporter ZnT8 (Slc30A8) is a major autoantigen in human type 1 diabetes. *Proc Natl Acad Sci USA.* 104, 17040-17045.
10. Enee, E., Kratzer, R., Arnoux, J. B., Barilleau, E., Hamel, Y., Marchi, C., Beltrand, J., Michaud, B., Chatenoud, L., Robert, J. J., and van Endert, P. (2012) ZnT8 is a major CD8+ T cell-recognized autoantigen in pediatric type 1 diabetes. *Diabetes* 61, 1779-1784.
11. Sladek, R., Rocheleau, G., Rung. J., Dina, C., Shen, L., Serre, D., Boutin, P., Vincent, D., Belisle, A., Hadjadj, S., Balkau, B., Heude, B., Charpentier, G., Hudson, T, J., Monitpetit, A, Pshezhetsky, A. V. Prentki, M., Posner, B. I., Balding, D. J., Meyre, D., Polychronakos, C., and Froguel, P. (2007) A genome-wide association study identifies novel risk loci for type 2 diabetes. *Nature.* 445, 881-885.
12. Flannick, J., Thorleifsson, G., Beer, N. L., Jacobs, S. B., Garup, N., Burt, N. P., Mahajan, A., Fuchsberger, C., Atzmon, G., Benediktsson, R, Blangero, J., Bowden, D. W., Brandslund, I., Brosnan, J., Burslem, F., Chambers, J., Cho, Y. S., Christensen, C., Douglas, D. A., Duggirala, R., Dymek, Z., Farjoun, Y., Fennell, T., Fontanillas, P., Forsen, T., Gabriel, S., Glaser, B., Gudbjartsson, D. F., Hanis, C., Hansen, T., Hreidarsson, A. B., Hveem, K., Ingelsson, E., Isomaa, B., Johansson, S., Jorgensen, T., Jorgensen, M. E., Kathiresan, S., Kong, A., Kooner, J., Kravic, J., Laakso, M., Lee, J. Y., Lind, L., Lindgren, C. M., Linneberg, A., Masson, G., Meitinger, T., Mohlke, K. L., Molven, A., Morris, A. P., Potluri, S., Rauramaa, R., Ribel-Madsen, R., Richard, A. M., Rolph, T., Salomaa, V., Segre, A. V., Skarstrand, H., Steinthorsdottir, V., Stringham, H. M., Sulem, P., Tai, E. S., Teo, Y. Y., Teslovich, T., Thorsteinsdottir, U., Trimmer. J. K., Tuomi, T., Tuomilehto, J., Vaziri-Sani, F., Voight, B. F., Wilson, J. G., Boehnke, M., McCarthy, M. I., Njolstad, P. R., Pedersen, O., Groop, L., Cox, D. R., Stefansson, K., and Altshuler, D. (2014) Loss-of-function mutations in SLC30A8 protect against type 2 diabetes. *Nat Genet* 46, 357-363.
13. Nicolson, T. J., Bellomo, E. A., Wijesekara, N., Loder, M. K., Baldwin, J. M., Gyulkhandanyan, A. V., Koshkin, V., Tarasov, A. I., Carzaniga, R., Kronenberger K., Taneja, T. K., da Silva Xavier, G., Libert, S., Froguel, P., Scharfmann, R., Stetsyuk, V., Ravassard, P., Parker, H., Gribble, F. M., Reimann, F., Sladek, R., Hughes, S. J., Johnson, P. R., Masseboeuf, M., Burcelin, R., Baldwin, S. A., Liu, M., Lara-Lemus, R., Arvan, P., Schuit, F. C., Wheeler, M. B., Chimienti, F., and Rutter, G. A (2009) Insulin storage and glucose homeostasis in mice null for the granule zinc transporter ZnT8 and studies of the type 2 diabetes-associated variants. *Diabetes* 58, 2070-2083.
14. Wijesekara, N., Dai, F. F., Hardy, A. B., Giglou, P. R., Bhattacharjee, A., Koshkin, V., Chimienti, F., Gaisano, H. Y, Rutter, G. A., and Wheeler, M. B. (2010) Beta cell-specific Znt8 deletion in mice causes marked defects in insulin processing, crystallisation and secretion. *Diabetologia* 53, 1656-1668.
15. Pound, L. D., Sarkar, S. A., Benninger, R. K., Wang, Y., Suwanichkul, A., Shadoan, M. K., Printz, R. L., Oeser, J. K., Lee, C. E, Piston, D. W., McGuinness, O. P., Hutton. J. C., Powell, D. R., and O'Brien, R. M. (2009) Deletion of the mouse Slc30a8 gene encoding zinc transporter-8 results in impaired insulin secretion. *Biochem J.* 421, 371-376.
16. Lemaire, K., Ravier, M, A., Schraenen, A., Creemers, J. W., Van de Plas, R., Granvik, M., Van Lommel, L., Waelkens, E., Chimienti. F., Rutter, G. A., Gilon, P., in't Veld, P. A., and Schuit, F. C. (2009) Insulin crystallization depends on zinc transporter ZnT8 expression, but is not required for normal glucose homeostasis in mice. *Proc Natl Acad Sci USA* 106, 14872-14877.
17. Pound, L. D., Sarkar, S. A., Ustione, A., Dadi, P. K., Shadoan, M. K., Lee, C. E., Walters, J. A., Shiota, M., McGuinness, O. P., Jacobson, D. A., Piston, D. W., Hutton, J. C., Powell, D. R., and O'Brien, R. M. (2012) The physiological effects of deleting the mouse SLC30A8 gene encoding zinc transporter-8 are influenced by gender and genetic background. *PLoS One* 7, e40972.
18. Chabosseau, P., and Rutter, G. A. (2016) Zinc and diabetes. *Arch Biochem Biophys*.
19. Saltiel, A. R., and Olefsky, J. M. (2017) Inflammatory mechanisms linking obesity and metabolic disease. *J Clin Invest* 127, 1-4,
20. Leahy, J. L., Cooper, H. E., Deal, D. A., and Weir, G. C. (1986) Chronic hyperglycemia is associated with impaired glucose influence on insulin secretion. A study in normal rats using chronic in vivo glucose infusions. *J Clin Invest* 77, 908-915.
21. Maedler, K., Spinas, G. A., Dyntar, D., Moritz, W., Kaiser, N., and Donath, M. Y. (2001) Distinct effects of saturated and monounsaturated fatty acids on beta-cell turnover and function. *Diabetes* 50, 69-76.
22. Poitout, V., and Robertson, R. P. (2008) Glucolipotoxicity: fuel excess and beta-cell dysfunction. *Endocr Rev* 29, 351-366.
23. Butcher, M. J., Hallinger, D., Garcia, E., Machida, Y., Chakrabarti, S., Nadler, J., Galkina, E. V., and Imai, Y. (2014) Association of proinflammatory cytokines and islet resident leucocytes with islet dysfunction in type 2 diabetes. *Diabetologia* 57, 491-501.
24. Hotamisligil, G. S. (2017) Inflammation, metaflammation and immunometabolic disorders. *Nature* 542, 177-185.
25. Donath, M. Y., and Shoelson, S. E. (2011) Type 2 diabetes as an inflammatory disease. *Nat Rev Immunol* 11, 98-107.
26. Tsai, S., Clemente-Casares, X., Revelo, X. S., Winer, S., and Winer, D. A, (2015) Are obesity-related insulin resistance and type 2 diabetes autoimmune diseases?*Diabetes* 64, 1886-1897.
27. Zumsteg, U., Frigerio, S., and Hollander, G. A. (2000) Nitric oxide production and Fas surface expression mediate two independent pathways of cytokine-induced murine beta-cell damage. *Diabetes* 49, 39-47.
28. Robertson, R. P., Harmon, J., Tran, P. O., and Poitout, V. (2004) Beta-cell glucose toxicity, lipotoxicity, and chronic oxidative stress in type 2 diabetes. *Diabetes* 53 Suppl 1, S119-124.
29. Eide, D. J. (2011) The oxidative stress of zinc deficiency. *Metallomics* 3, 1124-1129.
30. Homma. K., Fujisawa, T., Tsuburaya, N., Yamaguchi, N., Kadowaki, H., Takeda, K., Nishitoh, H., Matsuzawa, A., Naguro, I., and Ichijo, H. (2013) SOD1 as a molecular switch for initiating the homeostatic ER stress response under zinc deficiency. *Mol Cell* 52, 75-86.
31. Fonseca, S. C., Burcin, M., Gromada, J., and Urano, F. (2009) Endoplasmic reticulum stress in beta-cells and development of diabetes. *Curr Opin Pharmacol* 9, 763-770.
32. Merriman, C., Li, H., Li, H., and Fu, D. (2018) Highly specific monoclonal antibodies for allosteric inhibition and immunodetection of the human pancreatic zinc transporter ZnT8. *J Biol Chem* 293, 16206-16216.
33. Merriman, C., Huang, Q., Gu, W., Yu, L., and Fu, D. (2018) A subclass of serum anti-ZnT8 antibodies directed to the surface of live pancreatic beta-cells. *J Biol Chem* 293, 579-587.
34. Merriman, C., Huang, Q., Rutter, G. A., and Fu, D. (2016) Lipid-tuned Zinc Transport Activity of Human ZnT8 Protein Correlates with Risk for Type-2 Diabetes. *J Biol Chem* 291, 26950-26957.
35. Poitout, V., Amyot, J., Semache, M., Zarrouki, B., Hagman, D., and Fontes, G. (2010) Glucolipotoxicity of the pancreatic beta cell. *Biochim Biophys Acta* 1801, 289-298.
36. Eizirik, D. L., Colli, M. L., and Ortis, F. (2009) The role of inflammation in insulitis and beta-cell loss in type 1 diabetes. *Nat Rev Endocrinol* 5, 219-226.
37. Hakonen, E., Chandra, V., Fogarty, C. L., Yu, N. Y., Ustinov, J., Katayama, S., Galli, E., Danilova, T., Lindholm, P., Vartiainen, A., Einarsdottir, E., Krjutskov, K., Kere, J., Saarma, M., Lindahl, M., and Otonkoski, T. (2018) MANF protects human pancreatic beta cells against stress-induced cell death *Diabetologia* 61, 2202-2214.
38. Gurgul-Convey, E., Mehmeti, I., Plotz, T., Jorns, A., and Lenzen, S. (2016) Sensitivity profile of the human EndoC-betaH1 beta cell line to proinflammatory cytokines. *Diabetologia* 59, 2125-2133.
39. Thul, P. J., Akesson, L., Wiking, M., Mahdessian, D., Geladaki, A., Ait Blal, H., Alm, T., Asplund, A., Bjork, L., Breckels, L. M., Backstrom, A., Danielsson, F., Fagerberg, L., Fall, J., Gatto, L., Gnann, C., Hober, S., Hjeimare, M., Johansson, F., Lee, S., Lindskog, C., Mulder, J., Mulvey, C. M., Nilsson, P., Oksvold, P., Rockberg, J., Schutten, R., Schwenk, J. M., Sivertsson, A., Sjostedt, E., Skogs, M., Stadler, C., Sullivan, D. P., Tegel, H., Winsnes, C., Zhang, C., Zwahlen, M., Mardinoglu, A., Ponten, F., von Feilitzen, K., Lilley, K. S., Uhlen, M., and Lundberg, E. (2017) A subcellular map of the human proteome. *Science* 356.
40. Davidson, H, W., Wenzlau, J. M., and O'Brien, R. M. (2014) Zinc transporter 8 (ZnT8) and beta cell function. *Trends Endocrinol Metab* 25, 415-424.
41. Chimienti, F., Devergnas, S., Favier, A., and Seve, M. (2004) Identification and cloning of a beta-cell-specific zinc transporter, ZnT-8, localized into insulin secretory granules. *Diabetes* 53, 2330-2337.
42. Solimena, M., Dirkx, R., Jr., Hermel, J. M., Pleasic-Williams, S., Shapiro, J. A., Caron, L., and Rabin, D. U. (1996) ICA 512, an autoantigen of type I diabetes, is an intrinsic membrane protein of neurosecretory granules. *EMBO J* 15, 2102-2114.
43. Regazzi, R., Wollheim, C. B., Lang, J., Theler, J M., Rossetto, O., Montecucco, C., Sadoul, K., Weller, U., Palmer, M., and Thorens, B. (1995) VAMP-2 and cellubrevin are expressed in pancreatic beta-cells and are essential for Ca(2+)-but not for GTP gamma S-induced insulin secretion. *EMBO J* 14, 2723-2730.
44. Kay, T. W., Campbell I. L., Oxbrow, L., and Harrison, L. C. (1991) Overexpression of class I major histocompatibility complex accompanies insulitis in the non-obese diabetic mouse and is prevented by anti-interferon-gamma antibody. *Diabetologia* 34, 779-785.
45. Scheuner, D., and Kaufman, R. J. (2008) The unfolded protein response: a pathway that links insulin demand with beta-cell failure and diabetes. *Endocr Rev* 29, 317-333.
46. Farino, Z. J., Morgenstern, T. J., Vallaghe, J., Gregor, N., Donthamsetti, P., Harris, P. E., Pierre, N., Freyberg, R., Charrier-Savournin, F., Javitch, J. A., and Freyberg, Z. (2016) Development of a Rapid Insulin Assay by Homogenous Time-Resolved Fluorescence. *PLoS One* 11, e0148684.
47. Kharroubi, I., Ladriere, L., Cardozo, A. K., Dogusan, Z., Cnop, M., and Eizirik, D. L. (2004) Free fatty acids and cytokines induce pancreatic beta-cell apoptosis by different mechanisms: role of nuclear factor-kappaB and endoplasmic reticulum stress. *Endocrinology,* 145, 5087-5096.
48. Akerfeldt, M. C., Howes, J., Chan, J. Y., Stevens, V. A., Boubeuna, N., McGuire, H. M., King, C., Biden, T. J., and Laybutt, D. R. (2008) Cytokine-induced beta-cell death is independent of endoplasmic reticulum stress signaling. *Diabetes* 57, 3034-3044.
49. Cnop, M., Welsh, N., Jonas. J. C., Jorns. A., Lenzen, S., and Eizirik, D. L. (2005) Mechanisms of pancreatic beta-cell death in type 1 and type 2 diabetes: many differences, few similarities. *Diabetes* 54 Suppl 2, S97-107.
50. Li, Z., Liu, H., Niu, Z., Zhong, W., Xue, M., Wang, J., Yang, F. Zhou, Y., Zhou, Y., Xu, T., and Hou, J. (2018) Temporal Proteomic Analysis of Pancreatic beta-Cells in Response to Lipotoxicity and Glucolipotoxicity. *Mol Cell Proteomics* 17, 2119-2131.
51. Busch, A. K., Gurisik, E., Cordery, D. V., Sudlow, M., Denver, G. S., Laybutt, D. R., Hughes, W. E., and Biden, T. J. (2005) Increased fatty acid desaturation and enhanced expression of stearoyl coenzyme A desaturase protects pancreatic beta-cells from lipoapoptosis, *Diabetes* 54, 2917-2924.
52. Rojas, J., Bermudez, V., Palmar, J., Martinez, M. S., Olivar, L. C., Nava, M., Tomey, D., Rojas, M., Salazar, J., Garicano, C., and Velasco, M. (2018) Pancreatic Beta Cell Death: Novel Potential Mechanisms in Diabetes Therapy. *J Diabetes Res* 2018, 9601801.
53. Fabregat, A., Jupe, S., Matthews, L., Sidiropoulos, K., Gillespie, M., Garapati, P., Haw, R., Jassal, B., Korninger, F., May, B., Milacic, M., Roca, C. D., Rothfels, K., Sevilla, C., Shamovsky, V., Shorser, S., Varusai, T., Viteri, G., Weiser, J., Wu, G., Stein, L., Hermjakob H., and D'Eustachio, P. (2018) The Reactome Pathway Knowledgebase. *Nucleic Acids Res* 46, D649-D655.
54. Murata, S., Takahama, Y., Kasahara, M., and Tanaka, K. (2018) The immunoproteasome and thymoproteasome: functions, evolution and human disease. *Nat Immunol* 19, 923-931.
55. Arvan, P., Pietropaolo, M., Ostrov, D., and Rhodes, C. J. (2012) Islet autoantigens: structure, function, localization, and regulation. *Cold Spring Harb Perspect Med* 2.
56. Dudek, N. L., Tan, C. T., Gorasia, D. G., Croft, N. P., Illing, P. T., and Purcell, A, W. (2012) Constitutive and inflammatory immunopeptidome of pancreatic beta-cells. *Diabetes* 61, 3018-3025.
57. Jarchum, I., Baker, J. C., Yamada, T., Takaki, T., Marron, M. P., Serreze, D. V., and DiLorenzo, T. P. (2007) In vivo cytotoxicity of insulin-specific CD8+ T-cells in HLA-A*0201 transgenic NOD mice. *Diabetes* 56, 2551-2560.
58. Scotto, M., Afonso, G., Larger, E., Raverdy, C., Lemonnier, F. A., Carel, J. C., Dubois-Laforgue, D., Baz, B., Levy, D., Gautier, J. F., Launay, O., Bruno, G., Boitard, C., Sechi, L. A., Hutton, J. C., Davidson, H. W., and Mallone, R. (2012) Zinc transporter (ZnT)8(186-194) is an immunodominant CD8+ T cell epitope in HLA-A2+ type 1 diabetic patients. *Diabetologia* 55, 2026-2031.
59. Meng, L., Mohan, R., Kwok, B. H., Elofsson, M., Sin, N., and Crews, C. M. (1999) Epoxomicin, a potent and selective proteasome inhibitor, exhibits in vivo antiinflammatory activity. *Proc Natl Acad Sci USA* 96, 10403-10408.
60. Huang, Q., Merriman, C., Zhang, H., and Fu, D. (2017) Coupling of Insulin Secretion and Display of a Granule-resident Zinc Transporter ZnT8 on the Surface of Pancreatic Beta Cells. *J Biol Chem* 292, 4034-4043.
61. Wan, H., Merriman, C., Atkinson, M. A., Wasserfall, C. H., McGrail, K. M., Liang, Y., Fu, D., and Dai, H. (2017) Proteoliposome-based full-length ZnT8 self-antigen for type 1 diabetes diagnosis on a plasmonic platform. *Proc Natl Acad Sci USA* 114, 10196-10201.
62. El Muayed, M., Billings, L. K., Raja, M. R., Zhang, X., Park, P J., Newman, M. V., Kaufman, D. B., O'Halloran, T. V, and Lowe, W. L. Jr. (2010) Acute cytokine-mediated downregulation of the zinc transporter ZnT8 alters pancreatic beta-cell function. *J Endocrinol* 206, 159-169.
63. Egefjord, L., Jensen, J. L., Bang-Berthelsen, C. H., Petersen, A. B., Smidt, K., Schmitz, O., Karlsen, A. E., Pociot, F., Chimienti, F., Rungby, J., and Magnusson, N. E. (2009) Zinc transporter gene expression is regulated by pro-inflammatory cytokines: a potential role for zinc transporters in beta-cell apoptosis? *BMC Endocr Disord* 9, 7.
64. Cheng, L., Zhang, D., and Chen, B. (2016) Tumor necrosis factor alpha-induced protein-3 protects zinc transporter 8 against proinflammatory cytokine-induced downregulation. *Exp Ther Med* 12, 1509-1514.
65. Wong, W. P., Allen, N. B., Meyers, M. S., Link, E. O., Zhang, X., MacRenaris, K. W., and El Muayed, M. (2017) Exploring the Association Between Demographics. SLC30A8 Genotype, and Human Islet Content of Zinc, Cadmium, Copper, Iron, Manganese and Nickel. *Sci Rep* 7, 473.
66. Parsons, D. S., Hogstrand, C., and Maret, W. (2018) The C-terminal cytosolic domain of the human zinc transporter ZnT8 and its diabetes risk variant. *FEBS J* 285, 1237-1250.
67. Flannick, J., Mercader, J. M., Fuchsberger, C., Udler, M. S., Mahajan, A., Wessel, J., Teslovich, T. M., Caulkins, L., Koesterer, R., Barajas-Olmos, F., Blackwell, T. W., Boerwinkle, E., Brody, J. A., Centeno-Cruz. F., Chen, L., Chen, S., Contreras-Cubas, C., Cordova, E., Correa, A., Cortes, M., DeFronzo, R. A., Dolan, L., Drews, K. L., Elliott, A., Floyd, J. S., Gabriel, S., Garay-Sevilla, M. E., Garcia-Ortiz, H., Gross, M., Han, S., Heard-Costa, N. L., Jackson, A. U., Jorgensen, M. E., Kang, H. M., Kelsey, M., Kim, B. J., Koistinen, H. A., Kuusisto, J., Leader, J. B., Linneberg, A., Liu, C. T., Liu, J., Lyssenko, V., Manning, A. K., Marcketta, A., Malacara-Hernandez, J. M., Martinez-Hernandez, A., Matsuo, K., Mayer-Davis, E., Mendoza-Caamal, E., Mohlke, K. L., Morrison, A. C., Ndungu, A., Ng, M. C. Y., O'Dushlaine, C., Payne, A. J., Pihoker, C., Broad Genomics, P., Post, W. S., Preuss, M., Psaty, B. M., Vasan, R. S., Rayner, N. W. Reiner, A. P., Revilla-Monsalve, C., Robertson, N. R., Santoro, N., Schurmann, C., So, W. Y., Soberon, X., Stringham, H. M., Strom, T. M., Tam, C. H. T., Thameem, F., Tomlinson, B., Torres, J. M., Tracy, R. P., van Dam, R. M., Vujkovic, M., Wang, S., Welch, R. P., Witte, D. R., Wong, T. Y., Atzmon, G., Barzilai, N., Blangero, J., Bonnycastle, L. L., Bowden, D. W., Chambers, J. C., Chan, E., Cheng, C. Y., Cho, Y. S., Collins., F. S., de Vries, P. S., Duggirala, R., Glaser, B., Gonzalez, C., Gonzalez, M. E., Groop, L., Kooner, J. S., Kwak, S. H., Laakso, M., Lehman, D, M., Nilsson, P., Spector, T. D., Tai, E. S., Tuomi, T., Tuomilehto, J., Wilson, J. C., Aguilar-Salinas, C. A., Bottinger, E., Burke, B., Carey, D. J., Chan, J. C. N., Dupuis, J., Frossard, P., Heckbert, S. R., Hwang, M, Y., Kim, Y. J., Kirchner, H. L., Lee, J. Y., Lee, J., Loos, R. J. F., Ma, R. C. W., Morris, A. D., O'Donnell, C. J., Palmer, C. N. A., Pankow, J., Park, K. S., Rasheed, A., Saleheen, D., Sim, X., Small, K. S., Teo, Y. Y, Haiman, C., Hanis, C. L., Henderson, B. E., Orozco, L., Tusie-Luna, T., Dewey, F. E., Baras, A., Gieger, C., Meitinger, T., Strauch, K., Lange, L., Grarup, N., Hansen, T., Pedersen, O., Zeiller, P., Dabelea, D., Abecasis, G., Bell, G. I., Cox, N. J., Seielstad, M., Sladek, R., Meigs, J. B., Rich, S. S., Rotter, J. I., Discov, E. H. R. C., Charge, LuCamp, ProDiGy, GoT2D, Esp, Sigma, T. D., T2D, G., Amp T2D, C., Altshuler, D., Burnt, N. P., Scott, L. J., Morris, A. P., Florez, J. C., McCarthy, M. I., and Boehnke, M. (2019) Exome sequencing of 20,791 cases of type 2 diabetes and 24,440 controls. *Nature* 570, 71-76.

68. Chabosseau, P., Tuncay, E., Meur, G., Bellomo, E. A., Hessels, A., Hughes, S., Johnson, P. R., Bugliani, M., Marchetti, P., Turan, B., Lyon, A. R., Merkx, M. and Rutter, G. A. (2014) Mitochondrial and ER-targeted eCALWY probes reveal high levels of free Zn2+. *ACS Chem Bio* 9, 2111-2120.

69. Liu, Y., Batchuluun, B., Ho, L., Zhu, D., Prentice, K. J., Bhattacharjee, A., Zhang, M., Pourasgari, F., Hardy, A. B., Taylor, K. M., Gaisano, H., Dai, F. F., and Wheeler, M. B. (2015) Characterization of Zinc Influx Transporters (ZIPs) in Pancreatic beta Cells: ROLES IN REGULATING CYTOSOLIC ZINC HOMEOSTASIS AND INSULIN SECRETION. *J Bio Chem* 290, 18757-18769.

70. Taylor, K. M., Hiscox, S., Nicholson, R. I., Hogstrand, C., and Kille, P. (2012) Protein kinase CK2 triggers cytosolic zinc signaling pathways by phosphorylation of zinc channel ZIP7. *Sci Signal* 5, ra11.

71. Woodruff G., Bouwkamp, C. G., de Vrij, F. M., Lovenberg, T., Bonaventure, P., Kushner, S. A., and Harrington, A. W. (2018) The Zinc Transporter SLC39A7 (ZIP7) Is Essential for Regulation of Cytosolic Zinc Levels, *Mol Pharmacol* 94, 1092-1100.

72. Ohashi, W., Kimura, S., Iwanaga, T., Furusawa Y., Irie, T., Izumi, H., Watanabe, T., Hijikata, A., Hara, T., Ohara, O., Koseki, H., Sato, T., Robine, S., Mori, H., Hattori, Y., Watarai, H., Mishima, K., Ohno, H., Hase, K., and Fukada, T. (2016) Zinc Transporter SLC39A7/ZIP7 Promotes Intestinal Epithelial Self-Renewal by Resolving ER Stress. *PLoS Genet* 12, e1006349.

73. Tuncay, E., Bitirim, V. C., Durak, A., Carrat, G. R. J., Taylor, K. M., Rutter, G. A., and Turan, B. (2017) Hyperglycemia-Induced Changes in ZIP7 and ZnT7 Expression Cause Zn(2+) Release From the Sarco(endo) plasmic Reticulum and Mediate ER Stress in the Heart. *Diabetes* 66, 1346-1358.

74. Liu, M., Hodish, I., Rhodes, C. J., and Arvan, P. (2007) Proinsulin maturation, misfolding, and proteotoxicity. *Proc Natl Acad Sci USA* 104, 15841-15846.

75. Wenzlau, J. M., and Hutton, J. C. (2013) Novel diabetes autoantibodies and prediction of type 1 diabetes. *Curr Diab Rep* 13, 608-615.

76. Li, S., Li, H., Chen, B., Lu, D., Deng, W., Jiang, Y., Zhou, Z., and Yang, Z. (2013) Identification of novel HLA-A 0201-restricted cytotoxic T lymphocyte epitopes from Zinc Transporter 8. *Vaccine* 31, 1610-1615.

77. Yu, C., Burns, J. C., Robinson, W. H., Utz, P. J., Ho, P. P., Steinman, L., and Frey, A. B. (2016) Identification of Candidate Tolerogenic CD8(+) T Cell Epitopes for Therapy of Type 1 Diabetes in the NOD Mouse Model. *J Diabetes Res* 2016, 9083103.

78. Ravassard, P., Hazhouz, Y., Pechberty, S., Bricout-Neveu, E., Armanet, M., Czemichow, P., and Scharfmann, R. (2011) A genetically engineered human pancreatic beta cell line exhibiting glucose-inducible insulin secretion. 1 *Clin Invest* 121, 3589-3597.

79. Barlow, J., and Affourtit, C. (2013) Novel insights into pancreatic beta-cell glucolipotoxicity from real-time functional analysis of mitochondrial energy metabolism in INS-1E insulinoma cells. *Biochem J* 456, 417-426.

80. Li, Q., Lau A., Morris, T. J., Guo, L., Fordyce, C. B., and Stanley, E. F. (2004) A syntaxin 1, Galpha(o), and N-type calcium channel complex at a presynaptic nerve terminal: analysis by quantitative immunocolocalization. *J Neurosci* 24, 4070-4081.

81. Szoka, F., Jr., and Papahadjopoulos, D. (1980) Comparative properties and methods of preparation of lipid vesicles (liposomes). *Annu Rev Biophys Bioeng* 9, 467-508.

82. Fred, R. G., Kappe, C., Ameur, A., Cen. J., Bergsten, P., Ravassard, P., Scharfmann, R., and Welsh, N. (2015) Role of the AMP kinase in cytokine-induced human EndoC-betaH1 cell death. *Mol Cell Endocrinol* 414, 53-63.

---

We claim:

1. A method comprising:
   (a) permeabilizing human beta cells present in a substrate;
   (b) contacting the cells with a test agent; and
   (c) measuring the amount of zinc transporter 8 (ZnT8) using at least one anti-ZnT8 antibody or antigen-binding fragment thereof, and
   wherein the at least one anti-ZnT8 antibody or antigen-binding fragment thereof comprises a Fab, and
   wherein the Fab comprises SEQ ID NO:32 and SEQ ID NO:37.

2. A method comprising:
   (a) permeabilizing human beta cells present in a substrate;
   (b) contacting the cells with a test agent; and
   (c) measuring the amount of zinc transporter 8 (ZnT8) using at least one anti-ZnT8 antibody or antigen-binding fragment thereof, and
   wherein the at least one anti-ZnT8 antibody or antigen-binding fragment thereof comprises a Fab, and
   wherein the Fab comprises:
   (a) heavy chain complementary determining regions (CDRs) 1, 2, and 3, wherein the heavy chain CDR1 comprises SEQ ID NO:33, the heavy chain CDR2 comprises SEQ ID NO:34, and the heavy chain CDR3 comprises SEQ ID NO:35; and
   (b) light chain CDRs 1, 2, and 3, wherein the light chain CDR1 comprises SEQ ID NO:38, the light chain CDR2 comprises SEQ ID NO:39, and the light chain CDR3 comprises SEQ ID NO:40.

3. A method comprising:
   (a) permeabilizing human beta cells present in a substrate;
   (b) contacting the cells with a test agent; and
   (c) measuring the amount of zinc transporter 8 (ZnT8) using at least one anti-ZnT8 antibody or antigen-binding fragment thereof, and
   wherein the at least one anti-ZnT8 antibody or antigen-binding fragment thereof comprises (a) a first Fab comprising SEQ ID NO:32 and SEQ ID NO:37; and a second Fab comprising SEQ ID NO:52 and SEQ ID NO:57.

4. A method comprising:
   (a) permeabilizing human beta cells present in a substrate;
   (b) contacting the cells with a test agent; and
   (c) measuring the amount of zinc transporter 8 (ZnT8) using at least one anti-ZnT8 antibody or antigen-binding fragment thereof, and
   wherein the at least one detectably labeled anti-ZnT8 antibody or antigen-binding fragment thereof comprises:
   (a) a first Fab comprising:
     (i) heavy chain complementary determining regions (CDRs) 1, 2, and 3, wherein the heavy chain CDR1 comprises SEQ ID NO:33, the heavy chain CDR2 comprises SEQ ID NO:34, and the heavy chain CDR3 comprises SEQ ID NO:35, and
     (ii) light chain CDRs 1, 2, and 3, wherein the light chain CDR1 comprises SEQ ID NO:38, the light chain CDR2 comprises SEQ ID NO:39, nd the light chain CDR3 comprises SEQ ID NO:40; and
   (b) a second Fab comprising:
     (i) heavy chain complementary determining regions (CDRs) 1, 2, and 3, wherein the heavy chain CDR1 comprises SEQ ID NO:53, the heavy chain CDR2 comprises SEQ ID NO:54, and the heavy chain CDR3 comprises SEQ ID NO:55, and
     (ii) light chain CDRs 1, 2, and 3, wherein the light chain CDR1 comprises SEQ ID NO:58, the light chain CDR2 comprises SEQ ID NO:59, and the light chain CDR3 comprises SEQ ID NO:60.

5. A method comprising:
   (a) permeabilizing human beta cells present in a substrate;
   (b) contacting the cells with a test agent; and
   (c) measuring the amount of zinc transporter 8 (ZnT8) using at least one anti-ZnT8 antibody or antigen-binding fragment thereof, and
   wherein the at least one anti-ZnT8 antibody or antigen-binding fragment thereof comprises SEQ ID NO:2 and SEQ ID NO:7; SEQ ID NO:12 and SEQ ID NO:17; SEQ ID NO:22 and SEQ ID NO:27; SEQ ID NO:32 and SEQ ID NO:37; SEQ ID NO:42 and SEQ ID NO:47; or SEQ ID NO:52 and SEQ ID NO:57.

6. A method of identifying a modulator of ZnT8 comprising the steps of:
   (a) contacting human beta cells with a test agent; and
   (b) detecting a change in the amount of ZnT8 in the cell as compared to the amount of ZnT8 in a cell not contacted with the test agent, wherein the detecting step utilizes at least one anti-ZnT8 antibody or antigen-binding fragment thereof,
   wherein the at least one anti-ZnT8 antibody or antigen-binding fragment thereof comprises SEQ ID NO:2 and SEQ ID NO:7; SEQ ID NO:12 and SEQ ID NO:17; SEQ ID NO:22 and SEQ ID NO:27; SEQ ID NO:32 and SEQ ID NO:37; SEQ ID NO:42 and SEQ ID NO:47; or SEQ ID NO:52 and SEQ ID NO:57.

7. A method of identifying a modulator of ZnT8 comprising the steps of:
   (a) contacting human beta cells with a metabolic or cytokine stressor;
   (b) contacting the cells with a test agent; and
   detecting a change in the amount of ZnT8 in the cell as compared to the amount of ZnT8 in a cell contacted with the stressor but not contacted with the test agent, wherein the detecting step utilizes at least one anti-ZnT8 antibody or antigen-binding fragment thereof,
   wherein the at least one anti-ZnT8 antibody or antigen-binding fragment thereof comprises SEQ ID NO:2 and SEQ ID NO:7; SEQ ID NO:12 and SEQ ID NO:17; SEQ ID NO:22 and SEQ ID NO:27; SEQ ID NO:32 and SEQ ID NO:37; SEQ ID NO:42 and SEQ ID NO:47; or SEQ ID NO:52 and SEQ ID NO:57.

8. The method of claim 7, wherein the metabolic stressor comprises glucose and palmitic acid.

9. The method of claim 7, where in the cytokine stressor comprises one or more of IL-1β, TNF-α, IFN-γ, and IL-17.

10. A method comprising:
   (a) permeabilizing human beta cells present in a substrate;
   (b) contacting the cells with a test agent; and
   (c) measuring the amount of zinc transporter 8 (ZnT8) using at least one anti-ZnT8 antibody or antigen-binding fragment thereof, and
   wherein the at least one anti-ZnT8 antibody or antigen-binding fragment thereof comprises:
   (a) (i) heavy chain CDRs 1, 2, and 3, wherein the heavy chain CDR1 comprises SEQ ID NO:3, the heavy chain CDR2 comprises SEQ ID NO:4, and the heavy chain CDR3 comprises SEQ ID NO:5, and
   (a) (ii) light chain CDRs 1, 2, and 3, wherein the light chain CDR1 comprises SEQ ID NO:8, the light chain CDR2 comprises SEQ ID NO:9, and the light chain CDR3 comprises SEQ ID NO:10; or
   (b) (i) heavy chain CDRs 1, 2, and 3, wherein the heavy chain CDR1 comprises SEQ ID NO:13, the heavy chain CDR2 comprises SEQ ID NO:14, and the heavy chain CDR3 comprises SEQ ID NO:15, and
   (b) (ii) light chain CDRs 1, 2, and 3, wherein the light chain CDR1 comprises SEQ ID NO:18, the light chain CDR2 comprises SEQ ID NO:19, and the light chain CDR3 comprises SEQ ID NO:20; or
   (c) (i) heavy chain CDRs 1, 2, and 3, wherein the heavy chain CDR1 comprises SEQ ID NO:23, the heavy chain CDR2 comprises SEQ ID NO:24, and the heavy chain CDR3 comprises SEQ ID NO:25, and
   (c) (ii) light chain CDRs 1, 2, and 3, wherein the light chain CDR1 comprises SEQ ID NO:28, the light chain CDR2 comprises SEQ ID NO:29, and the light chain CDR3 comprises SEQ ID NO:30; or
   (d) (i) heavy chain CDRs 1, 2, and 3, wherein the heavy chain CDR1 comprises SEQ ID NO:33, the heavy chain CDR2 comprises SEQ ID NO:34, and the heavy chain CDR3 comprises SEQ ID NO:35, and
   (d) (ii) light chain CDRs 1, 2, and 3, wherein the light chain CDR1 comprises SEQ ID NO:38, the light chain CDR2 comprises SEQ ID NO:39, and the light chain CDR3 comprises SEQ ID NO:40; or
   (e) (i) heavy chain CDRs 1, 2, and 3, wherein the heavy chain CDR1 comprises SEQ ID NO:43, the heavy chain CDR2 comprises SEQ ID NO:44, and the heavy chain CDR3 comprises SEQ ID NO:45, and
   (e) (ii) light chain CDRs 1, 2, and 3, wherein the light chain CDR1 comprises SEQ ID NO:48, the light chain CDR2 comprises SEQ ID NO:49, and the light chain CDR3 comprises SEQ ID NO:50; or
   (f) (i) heavy chain CDRs 1, 2, and 3, wherein the heavy chain CDR1 comprises SEQ ID NO:53, the heavy chain CDR2 comprises SEQ ID NO:54, and the heavy chain CDR3 comprises SEQ ID NO:55, and
   (f) (ii) light chain CDRs 1, 2, and 3, wherein the light chain CDR1 comprises SEQ ID NO:58, the light chain CDR2 comprises SEQ ID NO:59, and the light chain CDR3 comprises SEQ ID NO:60.

11. The method of claim 10, wherein the at least one anti-ZnT8 antibody or antigen-binding fragment thereof specifically binds the cytoplasmic domain of ZnT8.

12. The method of claim 10, wherein the human beta cells comprise the cell line EndoC-βH1.

13. The method of claim 10, wherein the human beta cells are differentiated from human pluripotent stem cells (hPSCs).

14. The method of claim 10, wherein the human beta cells are primary pancreatic islets or pseudoislets.

15. The method of claim 10, wherein the at least one anti-ZnT8 antibody specifically binds ZnT8 antibody with a high signal-to-noise ratio as compared to other ZnT paralogs and high-abundant cellular proteins present in the human beta cells.

16. The method of claim 10, wherein the at least one anti-ZnT8 antibody or antigen-binding fragment thereof comprises a Fab.

17. The method of claim 10, wherein the detecting step comprises a proximity ligation assay.

18. A method of identifying a modulator of ZnT8 comprising the steps of:
   (a) contacting human beta cells with a test agent; and
   (b) detecting a change in the amount of ZnT8 in the cell as compared to the amount of ZnT8 in a cell not contacted with the test agent, wherein the detecting step utilizes at least one anti-ZnT8 antibody or antigen-binding fragment thereof, and
   wherein the at least one anti-ZnT8 antibody or antigen-binding fragment thereof comprises:
   (a) (i) heavy chain CDRs 1, 2, and 3, wherein the heavy chain CDR1 comprises SEQ ID NO:3, the heavy chain CDR2 comprises SEQ ID NO:4, and the heavy chain CDR3 comprises SEQ ID NO:5, and
   (a) (ii) light chain CDRs 1, 2, and 3, wherein the light chain CDR1 comprises SEQ ID NO:8, the light chain CDR2 comprises SEQ ID NO:9, and the light chain CDR3 comprises SEQ ID NO:10; or
   (b) (i) heavy chain CDRs 1, 2, and 3, wherein the heavy chain CDR1 comprises SEQ ID NO:13, the heavy chain CDR2 comprises SEQ ID NO:14, and the heavy chain CDR3 comprises SEQ ID NO:15, and (b) (ii) light chain CDRs 1, 2, and 3, wherein the light chain CDR1 comprises SEQ ID NO:18, the light chain CDR2 comprises SEQ ID NO:19, and the light chain CDR3 comprises SEQ ID NO:20; or (c) (i) heavy chain CDRs 1, 2, and 3, wherein the heavy chain CDR1 comprises SEQ ID NO:23, the heavy chain CDR2 comprises SEQ ID NO:24, and the heavy chain CDR3 comprises SEQ ID NO:25, and (c) (ii) light chain CDRs 1, 2, and 3, wherein the light chain CDR1 comprises SEQ ID NO:28, the light chain CDR2 comprises SEQ ID NO:29, and the light chain CDR3 comprises SEQ ID NO:30; or (d) (i) heavy chain CDRs 1, 2, and 3, wherein the heavy chain CDR1 comprises SEQ ID NO:33, the heavy chain CDR2 comprises SEQ ID NO:34, and the heavy chain CDR3 comprises SEQ ID NO:35, and (d) (ii) light chain CDRs 1, 2, and 3, wherein the light chain CDR1 comprises SEQ ID NO:38, the light chain CDR2 comprises SEQ ID NO:39, and the light chain CDR3 comprises SEQ ID NO:40; or (e) (i) heavy chain CDRs 1, 2, and 3, wherein the heavy chain CDR1 comprises SEQ ID NO:43, the heavy chain CDR2 comprises SEQ ID NO:44, and the heavy chain CDR3 comprises SEQ ID NO:45, and (e) (ii) light chain CDRs 1, 2, and 3, wherein the light chain CDR1 comprises SEQ ID NO:48, the light chain CDR2 comprises SEQ ID NO:49, and the light chain CDR3 comprises SEQ ID NO:50; or (f) (i) heavy chain CDRs 1, 2, and 3, wherein the heavy chain CDR1 comprises SEQ ID NO:53, the heavy chain CDR2 comprises SEQ ID NO:54, and the heavy chain CDR3 comprises SEQ ID NO:55, and (f) (ii) light chain CDRs 1, 2, and 3, wherein the light chain CDR1 comprises SEQ ID NO:58, the light chain CDR2 comprises SEQ ID NO:59, and the light chain CDR3 comprises SEQ ID NO:60.

19. A method of identifying a modulator of ZnT8 comprising the steps of:

(a) contacting human beta cells with a metabolic or cytokine stressor;

(b) contacting the cells with a test agent; and (c) detecting a change in the amount of ZnT8 in the cell as compared to the amount of ZnT8 in a cell contacted with the stressor but not contacted with the test agent, wherein the detecting step utilizes at least one anti-ZnT8 antibody or antigen-binding fragment thereof, and wherein the at least one anti-ZnT8 antibody or antigen-binding fragment thereof comprises:

(a) (i) heavy chain CDRs 1, 2, and 3, wherein the heavy chain CDR1 comprises SEQ ID NO:3, the heavy chain CDR2 comprises SEQ ID NO:4, and the heavy chain CDR3 comprises SEQ ID NO:5, and (a) (ii) light chain CDRs 1, 2, and 3, wherein the light chain CDR1 comprises SEQ ID NO:8, the light chain CDR2 comprises SEQ ID NO:9, and the light chain CDR3 comprises SEQ ID NO:10; or (b) (i) heavy chain CDRs 1, 2, and 3, wherein the heavy chain CDR1 comprises SEQ ID NO:13, the heavy chain CDR2 comprises SEQ ID NO:14, and the heavy chain CDR3 comprises SEQ ID NO:15, and (b) (ii) light chain CDRs 1, 2, and 3, wherein the light chain CDR1 comprises SEQ ID NO:18, the light chain CDR2 comprises SEQ ID NO:19, and the light chain CDR3 comprises SEQ ID NO:20; or (c) (i) heavy chain CDRs 1, 2, and 3, wherein the heavy chain CDR1 comprises SEQ ID NO:23, the heavy chain CDR2 comprises SEQ ID NO:24, and the heavy chain CDR3 comprises SEQ ID NO:25, and (c) (ii) light chain CDRs 1, 2, and 3, wherein the light chain CDR1 comprises SEQ ID NO:28, the light chain CDR2 comprises SEQ ID NO:29, and the light chain CDR3 comprises SEQ ID NO:30; or (d) (i) heavy chain CDRs 1, 2, and 3, wherein the heavy chain CDR1 comprises SEQ ID NO:33, the heavy chain CDR2 comprises SEQ ID NO:34, and the heavy chain CDR3 comprises SEQ ID NO:35, and (d) (ii) light chain CDRs 1, 2, and 3, wherein the light chain CDR1 comprises SEQ ID NO:38, the light chain CDR2 comprises SEQ ID NO:39, and the light chain CDR3 comprises SEQ ID NO:40; or (e) (i) heavy chain CDRs 1, 2, and 3, wherein the heavy chain CDR1 comprises SEQ ID NO:43, the heavy chain CDR2 comprises SEQ ID NO:44, and the heavy chain CDR3 comprises SEQ ID NO:45, and (e) (ii) light chain CDRs 1, 2, and 3, wherein the light chain CDR1 comprises SEQ ID NO:48, the light chain CDR2 comprises SEQ ID NO:49, and the light chain CDR3 comprises SEQ ID NO:50; or (f) (i) heavy chain CDRs 1, 2, and 3, wherein the heavy chain CDR1 comprises SEQ ID NO:53, the heavy chain CDR2 comprises SEQ ID NO:54, and the heavy chain CDR3 comprises SEQ ID NO:55, and (f) (ii) light chain CDRs 1, 2, and 3, wherein the light chain CDR1 comprises SEQ ID NO:58, the light chain CDR2 comprises SEQ ID NO:59, and the light chain CDR3 comprises SEQ ID NO:60.

\* \* \* \* \*